US008536180B2

(12) United States Patent
Clark et al.

(10) Patent No.: US 8,536,180 B2
(45) Date of Patent: Sep. 17, 2013

(54) PYRIMIDINE INHIBITORS OF KINASE ACTIVITY

(75) Inventors: Richard F. Clark, Gurnee, IL (US); Nwe Y. Ba-maung, Niles, IL (US); Scott A. Erickson, Zion, IL (US); Steve D. Fidanze, Grayslake, IL (US); Robert A. Mantei, Franklin, WI (US); George S. Sheppard, Wilmette, IL (US); Bryan K. Sorensen, Antioch, IL (US); Gary T. Wang, Libertyville, IL (US); Jieyi Wang, Lake Bluff, IL (US); Randy L. Bell, Lindenhurst, IL (US)

(73) Assignee: AbbVie Inc., North Chicago, IL (US)

( * ) Notice: Subject to any disclaimer, the term of this patent is extended or adjusted under 35 U.S.C. 154(b) by 382 days.

(21) Appl. No.: 12/787,915

(22) Filed: May 26, 2010

(65) Prior Publication Data

US 2010/0305118 A1 Dec. 2, 2010

Related U.S. Application Data

(60) Provisional application No. 61/181,555, filed on May 27, 2009.

(51) Int. Cl.
*A61K 31/497* (2006.01)
*A61K 31/535* (2006.01)
*A61K 31/505* (2006.01)
*C07D 413/14* (2006.01)
*C07D 403/14* (2006.01)

(52) U.S. Cl.
USPC ................ 514/252.18; 544/122; 544/331

(58) Field of Classification Search
USPC ............... 514/252.18, 233.2, 275; 544/122, 544/331
See application file for complete search history.

(56) References Cited

U.S. PATENT DOCUMENTS 8,354,422 B2 * 1/2013 Clark et al. ............. 514/275

FOREIGN PATENT DOCUMENTS

| WO | WO2005068452 A1 | 7/2005 |
| WO | WO2006074057 A2 | 7/2006 |
| WO | WO2006074057 A3 | 10/2006 |
| WO | WO2007099326 A1 | 9/2007 |

OTHER PUBLICATIONS

Adams T.E., et al., "Structure and Function of the Type 1 Insulin-Like Growth Factor Receptor," Cellular and Molecular Life Sciences, 2000, vol. 57 (7), pp. 1050-1093.
Alexia C., et al., "An Evaluation of the Role of Insulin-Like Growth Factors (IGF) and of Type-I IGF Receptor Signalling in Hepatocarcinogenesis and in the Resistance of Hepatocarcinoma Cells against Drug-Induced Apoptosis," Biochemical Pharmacology, 2004, vol. 68 (6), pp. 1003-1015.
Arteaga C.L., et al., "Growth Inhibition of Human Breast Cancer Cells in Vitro with an Antibody Against the Type I Somatomedin Receptor," Cancer Research, 1989, vol. 49 (22), pp. 6237-6241.
Bateman J.M., et al., "Insulin/IGF Signalling in Neurogenesis," Cellular and Molecular Life Sciences, 2006, vol. 63 (15), pp. 1701-1705.
Benito M., et al., "IGF-I: A Mitogen also Involved in Differentiation Processes in Mammalian Cells," The International Journal of Biochemistry & Cell Biology, 1996, vol. 28 (5), pp. 499-510.
Berge, S. M. et al., "Pharmaceutical Salts," Journal of Pharmaceutical Sciences, 1977, vol. 66 (1), pp. 1-19.
Bergmann U., et al., "Insulin-Like Growth Factor I Overexpression in Human Pancreatic Cancer: Evidence for Autocrine and Paracrine Roles," Cancer Research , 1995, vol. 55 (10), pp. 2007-2011.
Bohula E.A., et al., "Targeting the Type 1 Insulin-Like Growth Factor Receptor as Anti-Cancer Treatment," Anti-cancer Drugs, 2003, vol. 14 (9), pp. 669-682.
Brady G., et al., "Serum Levels of Insulin-Like Growth Factors (IGFS) and their Binding Proteins (IGFPBS), -1, -2, -3, in Oral Cancer," International Journal of Oral and Maxillofacial Surgery, 2007, vol. 36 (3), pp. 259-262.
Brown G.C., "Control of Respiration and Atp Synthesis in Mammalian Mitochondria and Cells," Biochemical, 1992, vol. 248, pp. 1-13.
Bruning J.C., et al., "A Muscle-Specific Insulin Receptor Knockout Exhibits Features of the Metabolic Syndrome of NIDDM without Altering Glucose Tolerance," Molecular Cell, 1998, vol. 2 (5), pp. 559-569.
Burfeind P., et al., "Antisense RNA to the Type I Insulin-Like Growth Factor Receptor Suppresses Tumor Growth and Prevents Invasion by Rat Prostate Cancer Cells in Vivo," Proceedings of the National Academy of Sciences of the USA, 1996, vol. 93 (14), pp. 7263-7268.

(Continued)

*Primary Examiner* — James O Wilson
*Assistant Examiner* — Ebenezer O Sackey
(74) *Attorney, Agent, or Firm* — Glen Gesicki

(57) ABSTRACT

Described herein are compounds of formula (I) or pharmaceutical acceptable salts or solvates thereof,

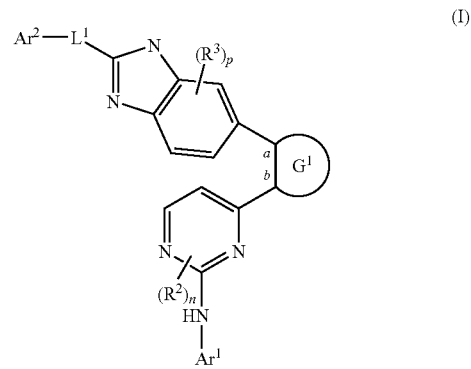

(I)

wherein $G^1$, $L^1$, $R^2$, $R^3$, n, p, $Ar^1$, and $Ar^2$ are defined in the description. Methods of making said compounds, and compositions comprising said compounds which are useful for inhibiting kinases such as IGF-1R are also disclosed.

25 Claims, No Drawings

(56) References Cited

OTHER PUBLICATIONS

Coppola D., et al., "A Functional Insulin-Like Growth Factor I Receptor is Required for the Mitogenic and Transforming Activities of the Epidermal Growth Factor Receptor," Molecular and Cellular Biology, 1994, vol. 14 (7), pp. 4588-4595.

Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Dandekar A.A., et al., "Comparison of the Signaling Abilities of the Cytoplasmic Domains of the Insulin Receptor and the Insulin Receptor-Related Receptor in 3T3-L1 Adipocytes," Endocrinology, 1998, vol. 139 (8), pp. 3578-3584.

Deangelis T., et al., "Insulin-Like Growth Factor I Receptor is Required for the Mitogenic and Transforming Activities of the Platelet-Derived Growth Factor Receptor," Journal of Cellular Physiology, 1995, vol. 164 (1), pp. 214-221.

Del Valle L., et al., "Insulin-Like Growth Factor I Receptor Activity in Human Medulloblastomas," Clinical Cancer Research, 2002, vol. 8 (6), pp. 1822-1830.

Djavan B., et al., "Insulin-Like Growth Factors and Prostate Cancer," World Journal of Urology, 2001, vol. 19 (4), pp. 225-233.

Durai R., et al., "The Role of the Insulin-Like Growth Factor System in Colorectal Cancer: Review of Current Knowledge," International Journal Colorectal Diseases., 2005, vol. 20 (3), pp. 203-220.

Greene, T.W., et al., Protective Groups in Organic Synthesis, 3rd Edition, John Wiley and Sons, Inc., 1999, Table of Contents.

Guo Y.S., et al., "Characterization of Insulinlike Growth Factor I Receptors in Human Colon Cancer," Gastroenterology, 1992, vol. 102 (4 pt 1), pp. 1101-1108.

Harrington E.A., et al., "C-Myc-Induced Apoptosis in Fibroblasts is Inhibited by Specific Cytokines," The EMBO Journal, 1994, vol. 13 (14), pp. 3286-3295.

Jiang Y., et al., "A High Expression Level of Insulin-Like Growth Factor I Receptor is Associated with Increased Expression of Transcription Factor SP1 and Regional Lymph Node Metastasis of Human Gastric Cancer," Clinical & Experimental Metastasis, 2004, vol. 21 (8), pp. 755-764.

Jiang Y., et al., "Induction of Tumor Suppression and Glandular Differentiation of A549 Lung Carcinoma Cells by Dominant-Negative IGF-I Receptor," Oncogene, 1999, vol. 18, pp. 6071-6077.

Kaleko M., et al., "Overexpression of the Human Insulinlike Growth Factor I Receptor Promotes Ligand-Dependent Neoplastic Transformation," Molecular and Cellular Biology, 1990, vol. 10 (2), pp. 464-473.

Kellerer M., et al., "Insulin- and Insulin-Like Growth-Factor-I Receptor Tyrosine-Kinase Activities in Human Renal Carcinoma," International Journal of Cancer, 1995, vol. 62 (5), pp. 501-507.

Kurmasheva R.T., et al., "IGF-I Mediated Survival Pathways in Normal and Malignant Cells," Biochimica et Biophysica Acta, 2006, vol. 1766 (1), pp. 1-22.

Leroith D., et al., "The Insulin-Like Growth Factor System and Cancer," Cancer Letters, 2003, vol. 195 (2), pp. 127-137.

Li S.L., et al., "Two New Monoclonal Antibodies against the ? Subunit of the Human Insulin-Like Growth Factor-I Receptor," Biochemical and Biophysical Research Communications, 1993, vol. 196 (1), pp. 92-98.

Li W., et al., "Role of the Activation Loop Tyrosines in Regulation of the Insulin-Like Growth Factor I Receptor-Tyrosine Kinase," The Journal of Biological Chemistry, 2006, vol. 281 (33), pp. 23785-23791.

Mathis G., "HTRF(R) Technology," Journal of Biomolecular Screening, 1999, vol. 4 (6), pp. 309-314.

Morrione A., et al., "Failure of the Bovine Papillomavirus to Transform Mouse Embryo Fibroblasts with a Targeted Disruption of the Insulin-Like Growth Factor I Receptor Genes," Journal of Virology, 1995, vol. 69 (9), pp. 5300-5303.

Neuvians T.P., et al., "Differential Expression of IGF Components and Insulin Receptor Isoforms in Human Seminoma Versus Normal Testicular Tissue," Neoplasia, 2005, vol. 7 (5), pp. 446-456.

O'Brien M.F., et al., "Insulin-Like Growth Factor I and Prostate Cancer," Urology, 2001, vol. 58 (1), pp. 1-7.

Pollak M.N., et al., "Insulin and Insulin-Like Growth Factor Signalling in Neoplasia," Nature Reviews Cancer, 2008, vol. 8 (12), pp. 915-928.

Pollak M.N., et al., "Insulin-Like Growth Factors and Neoplasia," Nature Reviews Cancer, 2004, vol. 4 (7), pp. 505-518.

Poste G. et al., "Lipid Vesicles as Carriers for Introducing Biologically Active Materials into Cells," Methods in Cell Biology, 1976, vol. 14, pp. 33-71.

Qi H., et al., "Expression of Type 1 Insulin-Like Growth Factor Receptor in Marrow Nucleated Cells in Malignant Hematological Disorders: Correlation with Apoptosis," Annals of Hematology, 2006, vol. 85 (2), pp. 95-101.

Samani A.A., et al., "The Role of the IGF System in Cancer Growth and Metastasis: Overview and Recent Insights," Endocrine Reviews, 2007, vol. 28 (1), pp. 20-47.

Sciacca L., et al., "In IGF-I Receptor-Deficient Leiomyosarcoma Cells Autocrine IGF-II Induces Cell Invasion and Protection from Apoptosis Via the Insulin Receptor Isoform A," Oncogene, 2002, vol. 21 (54), pp. 8240-8250.

Scotlandi K., et al., "Blockage of Insulin-like Growth Factor-I Receptor Inhibits the Growth of Ewing's Sarcoma in Athymic Mice," Cancer Research, 1998, vol. 58 (18), pp. 4127-4131.

Sell C., et al., "Effect of a Null Mutation of the Insulin-Like Growth Factor I Receptor Gene on Growth and Transformation of Mouse Embryo Fibroblasts," Molecular and Cellular Biology, 1994, vol. 14 (6), pp. 3604-3612.

Sell C., et al., "Simian Virus 40 Large Tumor Antigen is Unable to Transform Mouse Embryonic Fibroblasts Lacking Type 1 Insulin-Like Growth Factor Receptor," Proceedings of the National Academy of Sciences of the USA, 1993, vol. 90 (23), pp. 11217-11221.

Sohda M., et al., "The Role of Insulin-Like Growth Factor 1 and Insulin-Like Growth Factor Binding Protein 3 in Human Esophageal Cancer," Anticancer Research, 2004, vol. 24 (5A), pp. 3029-3034.

Surmacz E., "Function of the IGF-I Receptor in Breast Cancer," Journal of Mammary Gland Biology and Neoplasia, 2000, vol. 5 (1), pp. 95-105.

Trent J.C., et al., "Early Effects of Imatinib Mesylate on the Expression of Insulin-Like Growth Factor Binding Protein-3 and Positron Emission Tomography in Patients with Gastrointestinal Stromal Tumor," Cancer, 2006, vol. 107 (8), pp. 1898-1908.

Trojan J., et al., "Loss of Tumorigenicity of Rat Glioblastoma Directed by Episome-Based Antisense CDNA Transcription of Insulin-Like Growth Factor I," Proceedings of the National Academy of Sciences of the USA, 1992, vol. 89 (11), pp. 4874-4878.

Van Nimwegen M.J., et al., "Focal Adhesion Kinase: A Potential Target in Cancer Therapy," Biochemical Pharmacology, 2007, vol. 73 (5), pp. 597-609.

Vella V., et al., "A Novel Autocrine Loop Involving IGF-II and the Insulin Receptor Isoform-A Stimulates Growth of Thyroid Cancer," The Journal of Clinical Endocrinology and Metabolism, 2002, vol. 87 (1), pp. 245-254.

Vella V., et al., "The IGF System in Thyroid Cancer: New Concepts," Molecular Pathology, 2001, vol. 54 (3), pp. 121-124.

Walenkamp M.J., et al., "Genetic Disorders in the Growth Hormone—Insulin-Like Growth Factor-I Axis," Hormone Research, 2006, vol. 66 (5), pp. 221-230.

Wu X., et al., "Serum Levels of Insulin Growth Factor (IGF-I) and IGF-Binding Protein Predict Risk of Second Primary Tumors in Patients with Head and Neck Cancer," Clinical Cancer Research, 2004, vol. 10 (12 pt 1), pp. 3988-3995.

Yeh A.H., et al., "Human Melanoma Cells Expressing V600e B-RAF are Susceptible to IGF1R Targeting by Small Interfering RNAs," Oncogene, 2006, vol. 25 (50), pp. 6574-6581.

Zhao H., et al., "Plasma Levels of Insulin-Like Growth Factor-1 snd Binding Protein-3, and their Association with Bladder Cancer Risk," The Journal of urology, 2003, vol. 169 (2), pp. 714-717.

Zumkeller W., et al., "Insulin-Like Growth Factor System in Neuroblastoma Tumorigenesis and Apoptosis: Potential Diagnostic and Therapeutic Perspectives," Hormone & Metabolic Research, 1999, vol. 31 (2-3), pp. 138-141.

Zumkeller W., "The IGF/IGFBP System in CNS Malignancy," Moloclonal Pathology, 2001, vol. 54 (4), pp. 227-229.

Zumkeller W., "The Insulin-Like Growth Factor System in Hematopoietic Cells," Leukemia & Lymphoma, 2002, vol. 43 (3), pp. 487-491.

* cited by examiner

PYRIMIDINE INHIBITORS OF KINASE ACTIVITY

This application claims priority to U.S. Provisional Patent Application Ser. No. 61/181,555, which was filed on May 27, 2009 and is incorporated herein by reference.

TECHNICAL FIELD

Provided herein are compounds that inhibit protein kinases such as IGF-1R, compositions comprising the compounds, and methods of treating diseases using the compounds and said compositions.

BACKGROUND

Receptor tyrosine kinases (RTKs) have been implicated in cellular signaling pathways that control various cellular functions, including cell division, growth, metabolism, differentiation and survival, through reversible phosphorylation of the hydroxyl groups of tyrosine residues in proteins. Extracellular signals are transduced via activation of the cell surface receptors, with amplification and propagation using a complex choreography of cascades of protein phosphorylation and protein dephosphorylation events to avoid uncontrolled signaling. These signaling pathways are highly regulated, often by complex and intermeshed kinase pathways where each kinase may itself be regulated by one or more other kinases and protein phosphatases. The biological importance of these finely tuned systems is such that a variety of cell proliferative disorders have been linked to defects in one or more of the various cell signaling pathways mediated by tyrosine or serine/threonine kinases.

Receptor tyrosine kinases (RTKs) catalyze phosphorylation of certain tyrosyl amino acid residues in various proteins, including themselves, which govern cell growth, proliferation and differentiation. Insulin-like growth factor-1 receptor (IGF-1R) is a transmembrane tyrosine kinase ubiquitous among fetal and post-natal cell types. The IGF signaling axis is made up of multiple ligands (IGF-1, IGF-2 and Insulin), at least six high affinity ligand binding proteins and proteases, multiple receptors (IGF-1R & IGF-2R, IR and IRR), and many other down stream signaling proteins (Pollak, M N et al., Nature Reviews Cancer (2004) 4(7):505-518). The structure and function of the IGF-1R has been reviewed by Adams et al., Cell. Mol. Life Sci. (2000) 57:1050-1093 and Benito, M et al., Int J Biochem Cell Biol (1996) 28(5):499-510. The receptor is activated by the ligands IGF-1 and IGF-2, which are mitogenic proteins that signal through the IGF-1R and IR in an endocrine, paracrine or autocrine manner. Activation of the IGF-1 receptor tyrosine kinase elicits cellular responses which include cellular proliferation and protection of cells from apoptosis. (Id.) Over expression of IGF-1R leads to malignant transformation of cultured cells, while down regulation can reverse the transformed phenotype of tumor cells and potentially render them susceptible to apoptosis. (Id.) There are two splice variants of the IR gene, the IR-β isoform which regulates glucose uptake and is expressed in liver, muscle and adipose tissue, and the exon 11 variant human insulin receptor isoform A (IR-A) binds IGF-2 with high affinity and promotes proliferation and protection from apoptosis (Sciacca L. Oncogene (2002) 21(54):8240-8250). IR-A is predominantly expressed in fetal tissue and malignancies and at this receptor, IGF-2 is more potent than insulin in stimulating cancer cell migration. (Sciacca, Oncogene (2002) supra). Insulin receptor-related receptor tyrosine kinase (IRR) has 79% homology with the kinase domain of IR and is expressed only in a few limited cell types (Dandekar, A A et al., Endocrinology (1998) 139(8):3578-3584).

IGF-1R is a hetero-tetrameric, transmembrane, cell surface receptor tyrosine kinase. (Benito, Int J Biochem Cell Biol (1996)) An IGF-1 binding domain is part of the extracellular alpha-chain of IGF-1R, whereas the intracellular beta-chain contains the tyrosine kinase domain. Three tyrosine residues represent autophosphorylation sites, specifically $Tyr^{1131}$, $Tyr^{1135}$, and $Tyr^{1136}$ within the activation loop of the IGF-1R beta catalytic domain (Li, W et al., J. Biol. Chem. (2006) 281(33):23785-23791). Phosphorylation of all three is required for full receptor activation, and precedes phosphorylation of juxtamembrane tyrosines and carboxy terminus serines. The insulin receptor has three similar autophosphorylation sites on the activation loop and juxtamembrane region. Activation and autophosphorylation results in the recruitment of multiple docking proteins and the generation of intracellular signaling (Benito, Int J Biochem Cell Biol (1996)). Once activated, IGF-1R and IR can phosphorylate or interact directly with a number of intracellular protein substrates, including IRS-1, IRS-2, Grb2, Grb10, Grb14, Shc, SOC, 14.3.3, FAK, or indirectly with other proteins like PI3K and MAPK (Benito, M et al. Int J Biochem Cell Biol (1996) 28(5):499-510) (Brown, G C et al., Biochem. J (1992) 284: 1-13; Bruning, J C et al., Mol. Cell (1998) 2(5):559-569). Focal adhesion kinase (FAK) is of particular interest because of its role as a regulator of cell survival, proliferation, migration and invasion. FAK is activated by growth factor receptors such as IGF-1R, by binding through its N-terminal domain and autophosphorylation at $Tyr^{397}$. Activated or over expressed FAK is common in a wide variety of cancers, and may play a role in human carcinogenesis (van Nimwegen, M J et al., Biochem. Pharmacol. (2007) 73(5):597-609).

In addition to its role in cancers, the IGF receptor plays important and diverse roles in growth and development (Benito, M et al. Int J Biochem Cell Biol (1996) 28(5):499-510). IGF-1R has been implicated in several metabolic, and immunological diseases (Walenkamp, M J et al., Horm. Res. (2006) 66(5):221-230; Kurmasheva, R. T et al., Biochim. Biophys. Acta—Rev on Cancer (2006) 1766(1):1-22; Bateman, J M et al., Cell. Mol. Life Sci. (2006) 63(15):1701-1705, LeRoith, D, et al., Can. Lett. (2003) 195:127-137 and Samani A, et al., Endocrine Reviews 28(1):20-47.)

The role of the IGF/IGF-1R signaling system in cancer has been thoroughly examined over the last 15 years. In particular, the implication of IGF-1R in human cancer stems from its roles in stimulating mitogenesis, mobility and metastasis and in protecting against apoptosis. (Kurmasheva, Biochim. Biophys. Acta (2006).) Interest has grown with the understanding that in addition to its antiapoptotic and mitogenic roles, IGF/IGF-1R signaling seems to be necessary for the establishment and continuation of a transformed phenotype. It has been well established that constitutive activation or over expression, often results in non-adherent cell growth, even under serum depleted conditions in vitro, and is associated with the formation of tumors in nude mice. (Kaleko M et al, Mol Cell Biol. (1990) 10(2): 464-473). Perhaps even more importantly, it has been firmly established that cells, in which the gene encoding for IGF-1R has been deactivated, are totally resistant to transformation by agents which are normally capable of immortalizing normal cells, such as over expression of PDGFR or EGFR, the T antigen of the SV40 virus, the ES protein of bovine papilloma virus, and activated ras. (DeAngelis T et al., Cell. Physiol. (1995) 1640:214-221; Coppola D et al., Mol. Cell. Biol. (1994) 14(7):4588-4595; Morrione A J, Virol. 1995 695300-5303; Sell C et al., Mol. Cell. Biol. (1994) 14(6):3604-3612; Sell C et al., Proc. Natl. Acad. Sci.

USA (1993) 90(23):11217-11221). Thus, IGF-1R has been identified as the major survival factor that protects from oncogene induced cell death (Harrington et al., EMBO J. (1994) 13( ):3286-3295). IGF-1R is expressed in a large number and variety of tumors and the IGFs amplify the tumor growth through their interaction with the receptor. Evidence supporting the role of IGF-1R in carcinogenesis can be found in studies using monoclonal antibodies directed towards the receptor which inhibit the proliferation of numerous cell lines in culture and in vivo (Arteaga C et al., Cancer Res. (1989) 49(22):6237-6241; Li et al., Biochem. Biophys. Res. Com. (1993) 196(1):92-98; Scotlandi K et al., Cancer Res. (1998) 58(18):4127-4131). Dominant negative IGF-1R is capable of inhibiting tumor proliferation (Jiang et al., Oncogene (1999) 18(44):6071-6077). The IGF signaling axis is implicated in various tumor types including:

breast cancer (Surmacz, J. Mammary Gland Bio. Neoplasia (2000) 5(1):95-105, LeRoith, Can. Lett. (2003) and Artega, Cancer Res. (1989)), sarcoma including soft-tissue sarcoma (e.g., cartilage sarcoma, connective tissue (chondrosarcoma) and fibrous matrix (fibrosarcoma)) and hard bony sarcomas (e.g., Ewing's sarcoma, osteosarcoma and giant cell tumor of bone) (Scotlandi, Cancer Res. (1998), lung cancer, including non-small cell and small cell lung carcinomas and mesotheliomas (Jiang, Y et al., Oncogene (1999) 18:6071-6077 and LeRoith, Can. Lett. (2003), prostate cancer (Djavan et al., World J Urol. (2001) 19(4): 225-233; O'Brien et al., Urology (2001) 58(1):1-7 and LeRoith, Can. Lett. (2003)), colorectal cancer (Guo et al., Gastroenterology, 1992, 102, 1101-1108; Durai, R et al., Int. J Colorectal Dis. (2005) 20(3):203-220 and LeRoith, Can. Lett. (2003)), renal cancer (Kellerer M. et al., Int. J. Cancer (1995) 62(5): 501-507), pancreatic cancer (Bergmann, U et al., Cancer Res. (1995) 55(10):2007-2011), hematologic cancers, including lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, acute megakaryocytic leukemia, promyelocytic leukemia, erythroleukemia, malignant lymphoma, Hodgkins lymphoma, non-Hodgkins lymphoma, lymphoblastic T cell lymphoma, Burkitt's lymphoma, follicular lymphoma, myelodysplastic syndromes, (Zumkeller W et al., Leuk. Lymph (2002) 43(3): 487-491; and Qi, Ann Hematol. (2006) 85:95-101.), neuroblastomas (Zumkeller, W et al., Horm. Metab. Res. 1999, 31, 138-141), primary CNS tumors including: astrocytomas (also known as "gliomas") including glioblastoma multiforme; meningiomas and medulloblastomas (Zumkeller, W et al., Mol. Pathol. (2001) 54(4):227-229, Del Valle L, et al., Clin. Cancer Res. (2002) 8:1822-1830 and Trojan et al., Proc. Natl. Acad. Sci. USA (1992) 89:4874-4878.), secondary CNS tumors, i.e., metastases in the central nervous system (e.g., the brain), of a tumor originating outside of the central nervous system (Burfeind P, et al, PNAS (1996) 93:7263-7268), head and neck cancer (Wu X., et al, Clin. Cancer Res. (2004) 10:3988-95), thyroid cancer (Vella V et al., J. Clin. Endocrinol. Metab. (2002) 87:245-254; Vella V et al., Mol. Pathol. (2001) 54(3): 121-124), hepatocarcinoma (Alexia, C et al., Biochem. Pharmacol. (2004) 68:1003-1015), ovarian cancer, vulval cancer, cervical cancer, endometrial cancer, testicular cancer (Neuvians T P, et al, Neoplasia (2005) 7:446-56), bladder cancer (Zhao H., et al, J. Urology (2003) 169:714-717), esophageal cancer (Sohda M, et al, Anticancer Research. (2004) 24:3029-3034), gastric cancer (Jiang, Y, et al, Clinical & Experimental Metastasis (2004) 21:755-64), buccal cancer, cancer of the mouth, (Brady G et al., Int. J. of Oral & Maxillofacial Surg. (2007) 36:259-62).

GIST (gastrointestinal stromal tumor) (Trent J C, et al, Cancer. (2006) 107:1898-908), and skin cancer including melanoma (Yeh A H, et al, Oncogene. (2006) 25:6574-81).

Thus, in virtually all types of human cancers there is a strong association between dysregulation of IGF signaling and carcinogenesis (Bohula E A et al., Anticancer Drugs (2003) 14(9):669-682). Inhibition of IGF-1R and/or IR expression or function has been shown to block tumor growth and metastasis and also enhance sensitivity to other antineoplastic therapies, including cytotoxic drugs and radiation. (Bohula, Anticancer Drugs (2003).

The identification of effective small compounds which specifically inhibit signal transduction and cellular proliferation by modulating the activity of tyrosine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, and macromolecular extravasation and matrix deposition as well as associated disorders would be beneficial.

SUMMARY

One embodiment pertains to compounds that have formula (I)

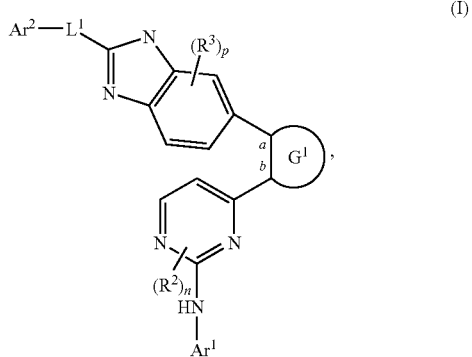

or pharmaceutically acceptable salts, solvates, prodrugs, salts of prodrugs, or combinations thereof, wherein
$G^1$ is formula (i), (ii), (iii), or (iv)

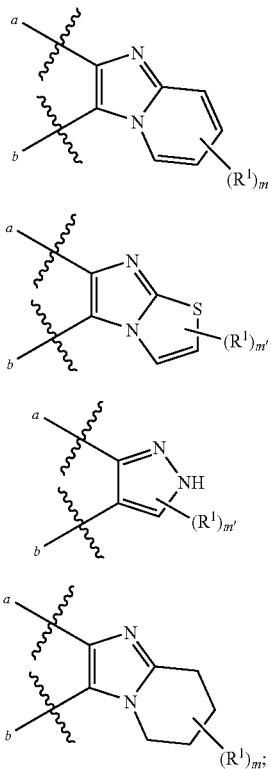

m is 0, 1, 2, 3, or 4;
m' is 0, 1, or 2;
n is 0, 1, or 2;
p is 0, 1, 2, or 3;
$R^1$, $R^2$, and $R^3$ are optional substituents, and when present, are each independently alkyl, halogen, —O(alkyl), —O(haloalkyl), or haloalkyl;
a and b designate the points of attachment at which formula (i), (ii), (iii), and (iv) are bound to formula (I);
$L^1$ is a bond, O, N(H), or $(CR^4R^5)_q$;
$R^4$ and $R^5$, at each occurrence, are each independently hydrogen, alkyl, halogen, or haloalkyl;
q is 1, 2, 3, or 4;
$Ar^1$ is aryl or heteroaryl; each of which is independently unsubstituted or substituted with 1, 2, 3, 4, or 5 substituents as represented by T, wherein each T is selected from the group consisting of alkyl, alkenyl, alkynyl, halogen, haloalkyl, oxo, CN, $NO_2$, $G^2$, —$OR^6$, —$OC(O)R^7$, —$SR^6$, —$S(O)R^7$, —$S(O)_2R^7$, —$S(O)_2N(R^8)(R^9)$, —$N(R^8)(R^9)$, —$N(R^8)C(O)R^7$, —$N(R^8)C(O)OR^7$, —$N(R^8)S(O)_2R^7$, —$N(R^8)C(O)N(R^8)(R^9)$, —$N(R^8)C(O)$—$(C_{1-6}$ alkylenyl)-$N(R^8)(R^9)$, —$N(R^8)S(O)_2N(R^8)(R^9)$, —$C(O)R^6$, —$C(O)OR^6$, —$C(O)N(R^8)(R^9)$, —$(C_{1-6}$ alkylenyl)-$G^2$, —$(C_{1-6}$ alkylenyl)-$OR^6$, —$(C_{1-6}$ alkylenyl)-$OC(O)R^7$, —$(C_{1-6}$ alkylenyl)-$SR^6$, —$(C_{1-6}$ alkylenyl)-$S(O)R^7$, —$(C_{1-6}$ alkylenyl)-$S(O)_2R^7$, —$(C_{1-6}$ alkylenyl)-$S(O)_2N(R^8)(R^9)$, —$(C_{1-6}$ alkylenyl)-$N(R^8)(R^9)$, —$(C_{1-6}$ alkylenyl)-$N(R^8)C(O)R^7$, —$(C_{1-6}$ alkylenyl)-$N(R^8)C(O)OR^7$, —$(C_{1-6}$ alkylenyl)-$N(R^8)S(O)_2R^7$, —$(C_{1-6}$ alkylenyl)-$N(R^8)C(O)N(R^8)(R^9)$, —$(C_{1-6}$ alkylenyl)-$N(R^8)S(O)_2N(R^8)(R^9)$, —$(C_{1-6}$ alkylenyl)-$C(O)R^6$, —$(C_{1-6}$ alkylenyl)-$C(O)OR^6$, and —$(C_{1-6}$ alkylenyl)-$C(O)N(R^8)(R^9)$;

two substituents on the vicinal carbon atoms of $Ar^1$, together with the carbon atoms to which they are attached, optionally form a monocyclic 5- or 6-membered heterocycle containing one or two heteroatoms selected from N(H), O, S, S(O), or $S(O)_2$, wherein each of the monocyclic heterocycle is optionally substituted with 1, 2, 3, or 4 alkyl groups;
each occurrence of $R^6$ and $R^9$ are each independently hydrogen, alkyl, haloalkyl, —$(C_{1-6}$ alkylenyl)-CN, —$(C_{1-6}$ alkylenyl)-OH, —$(C_{1-6}$ alkylenyl)-C(O)OH, $G^3$, or —$(C_{1-6}$ alkylenyl)-$G^3$;
each occurrence of $R^7$ is independently alkyl, haloalkyl, —$(C_{1-6}$ alkylenyl)-CN, —$(C_{1-6}$ alkylenyl)-OH, $G^3$, or —$(C_{1-6}$ alkylenyl)-$G^3$;
each occurrence of $R^8$ is independently hydrogen, alkyl, or haloalkyl;
each occurrence of $G^2$ is independently aryl, heteroaryl, heterocycle, cycloalkyl, or cycloalkenyl, each of which is independently unsubstituted or substituted with 1, 2, 3, 4, or 5 substituents selected from the group consisting of $G^3$, —$(C_{1-6}$ alkylenyl)-$G^3$, and $R^{10}$;
each occurrence of $G^3$ is independently aryl, heteroaryl, heterocycle, cycloalkyl, or cycloalkenyl, each of which is independently unsubstituted or substituted with 1, 2, 3, 4, or 5 $R^{10}$ groups;
$Ar^2$ is aryl or heteroaryl, each of which is independently unsubstituted or substituted with 1, 2, 3, 4, or 5 $R^{10}$ groups;
each occurrence of $R^{10}$ is independently alkyl, alkenyl, alkynyl, halogen, haloalkyl, oxo, CN, $NO_2$, —$OR^{Z1}$, —$OC(O)R^{Z2}$, —$SR^{Z1}$, —$S(O)R^{Z2}$, —$S(O)_2R^{Z2}$, —$S(O)_2N(R^{Z3})(R^{Z4})$, —$N(R^{Z3})(R^{Z4})$, —$N(R^{Z3})C(O)R^{Z2}$, —$N(R^{Z3})C(O)OR^{Z2}$, —$N(R^{Z3})S(O)_2R^{Z2}$, —$N(R^{Z3})C(O)N(R^{Z3})(R^{Z4})$, —$N(R^{Z3})S(O)_2N(R^{Z3})(R^{Z4})$, —$C(O)R^{Z1}$, —$C(O)OR^{Z1}$, —$C(O)N(R^{Z3})(R^{Z4})$, —$(C_{1-6}$ alkylenyl)-$OR^{Z1}$, —$(C_{1-6}$ alkylenyl)-$OC(O)R^{Z2}$, —$(C_{1-6}$ alkylenyl)-$SR^{Z1}$, —$(C_{1-6}$ alkylenyl)-$S(O)R^{Z2}$, —$(C_{1-6}$ alkylenyl)-$S(O)_2R^{Z2}$, —$(C_{1-6}$ alkylenyl)-$S(O)_2N(R^{Z3})(R^{Z4})$, —$(C_{1-6}$ alkylenyl)-$N(R^{Z3})(R^{Z4})$, —$(C_{1-6}$ alkylenyl)-$N(R^{Z3})C(O)R^{Z2}$, —$(C_{1-6}$ alkylenyl)-$N(R^{Z3})C(O)OR^{Z2}$, —$(C_{1-6}$ alkylenyl)-$N(R^{Z3})S(O)_2R^{Z2}$, —$(C_{1-6}$ alkylenyl)-$N(R^{Z3})C(O)N(R^{Z3})(R^{Z4})$, —$(C_{1-6}$ alkylenyl)-$N(R^{Z3})S(O)_2N(R^{Z3})(R^{Z4})$, —$(C_{1-6}$ alkylenyl)-$C(O)R^{Z1}$, —$(C_{1-6}$ alkylenyl)-$C(O)OR^{Z1}$, or —$(C_{1-6}$ alkylenyl)-$C(O)N(R^{Z3})(R^{Z4})$;
each occurrence of $R^{Z1}$, $R^{Z3}$, and $R^{Z4}$, are each independently hydrogen, alkyl, or haloalkyl; and
each occurrence of $R^{Z2}$ is independently alkyl or haloalkyl.

Also provided are pharmaceutical compositions comprising therapeutically effective amounts of one or more compounds of formula (I) or pharmaceutically acceptable salts or solvates thereof, in combination with one or more pharmaceutically acceptable carriers. These pharmaceutical compositions are useful for the treatment of diseases or conditions described herein.

One embodiment is directed to methods for treating cancers in mammals comprising administering thereto therapeutically effective amounts of one or more compounds described herein, or pharmaceutically acceptable salts or solvates thereof, alone or in combination with one or more pharmaceutically acceptable carriers.

Yet another embodiment pertains to methods of decreasing tumor volume in mammals comprising administering thereto therapeutically effective amounts of one or more compounds described herein, or pharmaceutically acceptable salts or solvates thereof, alone or in combination with one or more pharmaceutically acceptable carriers.

Still another embodiment pertains to methods of treating bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer or thyroid cancer in mammals, or combinations thereof; the methods comprising administering thereto therapeutically effective amounts of one or more compounds described herein or pharmaceutically acceptable salts or solvates thereof, with or without also administering radiotherapy thereto, and alone or in combination with one or more pharmaceutically acceptable carriers.

Provided herein are also the use of one or more compounds described herein, or pharmaceutically acceptable salts or solvates thereof for the preparation of medicaments for use in the treatment of diseases or conditions described herein, particularly, for use in the treatment of bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer, or thyroid cancer, or combinations thereof, in mammals (e.g., human) in need thereof.

The compounds, compositions comprising the compounds, and methods for treating or preventing conditions and disorders by administering the compounds and pharmaceutical compositions thereof are further described herein.

These and other objectives of the invention are described in the following paragraphs. These objectives should not be deemed to narrow the scope of the invention.

DETAILED DESCRIPTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Provided are compounds of formula (I)

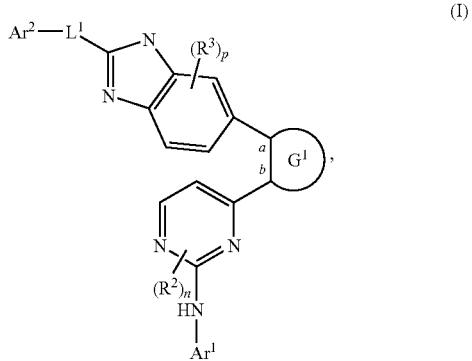

wherein $Ar^1$, $Ar^2$, $R^2$, $R^3$, $G^1$, n, p, and $L^1$ are as disclosed above in the Summary and below in the Detailed Description. Compositions comprising such compounds and methods for treating conditions and disorders using such compounds and compositions are also disclosed.

In various embodiments, there may be variables that occur more than one time in any substituent or in the compound or any other formulae herein. Definition of a variable on each occurrence is independent of its definition at another occurrence. Further, combinations of variables are permissible only if such combinations result in stable compounds. Stable compounds are compounds that can be isolated from a reaction mixture.

a. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to, ethenyl, 3-methylbut-2-enyl, prop-1-enyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a saturated, straight or branched hydrocarbon chain containing from 1 to 10 carbon atoms. The term "$C_{1-6}$ alkyl" as used herein, means a saturated, straight or branched hydrocarbon chain containing from 1 to 6 carbon atoms. Representative examples of alkyl include, but are not limited to, methyl, ethyl, n-propyl, iso-propyl, n-butyl, sec-butyl, iso-butyl, tert-butyl, n-pentyl, iso-pentyl, neopentyl, n-hexyl, 1-methylbutyl, 2-methylbutyl, 3-methylbutyl, 1,1-dimethylpropyl, 1,2-dimethylpropyl, 2,2-dimethylpropyl, 1-methylpropyl, 1-ethylpropyl, 1,2,2-trimethylpropyl, 2-ethylhexyl, 3-methylhexyl, 2,2-dimethylpentyl, 2,3-dimethylpentyl, n-heptyl, n-octyl, n-nonyl, and n-decyl.

The term "alkylene" or "alkylenyl" means a divalent group derived from a saturated, straight or branched hydrocarbon chain of from 1 to 10 carbon atoms. The term "$C_{1-6}$ alkylenyl" means a divalent group derived from a saturated, straight or branched chain hydrocarbon of from 1 to 6 carbon atoms. Representative examples of alkylene include, but are not limited to, —CH$_2$—, —CH(CH$_3$)—, —CH$_2$C(CH$_3$)$_2$—, —CH(C$_2$H$_5$), —CH(CH(CH$_3$)(C$_2$H$_5$))—, —C(H)(CH$_3$)CH$_2$CH$_2$—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkynyl" as used herein, means a straight or branched hydrocarbon chain containing from 2 to 10 carbon atoms and containing at least one carbon-carbon triple bond. Representative examples of alkynyl include, but are not limited, to acetylenyl, 1-propynyl, 2-propynyl, 1,1-dimethylprop-2-ynyl, 1-propyl-pent-3-ynyl, 3-butynyl, 2-pentynyl, and 1-butynyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl, dihydronaphthalenyl, and tetrahydronaphthalenyl. The phenyl and the bicyclic aryls, with the exception of the bicyclic aryls represented by $Ar^1$ and $Ar^2$, are attached to the parent molecular moiety through any carbon atom contained within the phenyl and the bicyclic aryls respectively. The bicyclic aryls represented by $Ar^1$ and $Ar^2$ are attached to the parent moiety through any substitutable carbon atoms within the phenyl moiety of the bicyclic aryls.

The term "cycloalkenyl" as used herein, means a monocyclic or bicyclic ring system containing zero heteroatoms in the ring. The monocyclic cycloalkenyl has three-, four-, five-, six-, seven- or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic cycloalkenyls include, but are not limited to, 2-cyclohexen-1-yl, 3-cyclohexen-1-yl, 2,4-cyclohexadien-1-yl and 3-cyclopenten-1-yl. Bicyclic cycloalkenyls are exemplified by a monocyclic cycloalkenyl fused to a monocyclic cycloalkyl, or a monocyclic cycloalkenyl fused to a monocyclic cycloalkenyl. Representative examples of bicyclic ring systems include, but are not limited to 3a, 4, 5, 6, 7,7a-hexahydro-1H-indenyl, 4,5,6,7-tetrahydro-3aH-indene, and octahydronaphthalenyl. The cycloalkenyl groups are appended to the parent molecular moiety through any substitutable carbon atom within the groups, and may contain one or two alkylene bridges of 1, 2, 3, or 4 carbon atoms, wherein each bridge links two non-adjacent atoms within the groups.

The term "cycloalkyl" as used herein, means a monocyclic, or a bicyclic cycloalkyl, or a spirocyclic cycloalkyl. The monocyclic cycloalkyl is a carbocyclic ring system containing 3, 4, 5, 6, 7, or 8 carbon atoms and zero heteroatoms as ring atoms, and zero double bonds. Examples of monocyclic cycloalkyls include cyclopropyl, cyclobutyl, cyclopentyl, cyclohexyl, cycloheptyl, and cyclooctyl. Bicyclic cycloalkyl is exemplified by a monocyclic cycloalkyl fused to a monocyclic cycloalkyl. Representative examples of bicyclic cycloalkyls include, but are not limited to, bicyclo[4.1.0]heptane, bicyclo[6.1.0]nonane, octahydroindene, and decahydronaphthalene. The monocyclic and the bicyclic cycloalkyl groups may contain one or two alkylene bridges of 1, 2, 3, or 4 carbon atoms, wherein each bridge links two non-adjacent atoms within the groups. Examples of such bridged cycloalkyls include, but are not limited to, bicyclo[2.2.1]heptyl, bicyclo[3.1.1]heptyl, bicyclo[2.2.2]octyl, bicyclo[3.3.1]nonyl, adamantyl (tricyclo[3.3.1.1$^{3,7}$]decane), and noradamantyl (octahydro-2,5-methanopentalene). Spirocyclic cycloalkyl is exemplified by a monocyclic or a bicyclic cycloalkyl, wherein two of the substituents on the same carbon atom of the ring, together with said carbon atom, form a 3-, 4-, 5-, or 6-membered monocyclic cycloalkyl. An example of a spirocyclic cycloalkyl is spiro[2.5]octane. The monocyclic, bicyclic, and spirocyclic cycloalkyl groups can be appended to the parent molecular moiety through any substitutable carbon atom of the groups.

The term "$C_{3-6}$ cycloalkyl" as used herein, means a 3-, 4-, 5-, or 6-membered monocyclic cycloalkyl as defined herein.

The term "halo" or "halogen" as used herein, means —Cl, —Br, —I, or —F.

The term "haloalkyl" as used herein, means an alkyl group, as defined herein, in which one, two, three, four, five, six, or seven hydrogen atoms are replaced by halogen. Representative examples of haloalkyl include, but are not limited to, chloromethyl, 2-fluoroethyl, 2-fluoropropyl, 2-fluoro-1-methylethyl, 2,2-difluoroethyl, trifluoromethyl, 2,2,2-trifluoroethyl, 2,2,2-trifluoro-1,1-dimethylethyl, difluoromethyl, 3-fluoro-3-methylbutyl, 3,3,3-trifluoropropyl, pentafluoroethyl, 2-chloro-3-fluoropentyl, and 2-iodoethyl.

The term "$C_{1-6}$ haloalkyl" as used herein, means a $C_{1-6}$ alkyl group, as defined herein, in which one, two, three, four, five, six, or seven hydrogen atoms are replaced by halogen.

The term "heteroaryl," as used herein, means a monocyclic heteroaryl or a bicyclic heteroaryl. The monocyclic heteroaryl is a 5- or 6-membered ring containing at least one heteroatom independently selected from the group consisting of O, N, and S. The 5-membered ring contains two double bonds and one, two, three, or four heteroatoms. The 6-membered ring contains three double bonds and one, two, three, or four heteroatoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Non-limiting examples of bicyclic heteroaryls include, but are not limited to, benzofuranyl, benzoxadiazolyl, 1,3-benzothiazolyl, benzimidazolyl, benzodioxolyl, benzothienyl, chromenyl, cinnolinyl, furopyridine, indolyl, indazolyl, isoindolyl, isoquinolinyl, naphthyridinyl, oxazolopyridine, quinolinyl, and thienopyridinyl. The monocyclic and the bicyclic heteroaryl groups, with the exception of the bicyclic heteroaryls represented by $Ar^1$ and $Ar^2$, are connected to the parent molecular moiety through any substitutable carbon atom or any substitutable nitrogen atom contained within the groups. The bicyclic heteroaryls represented by $Ar^1$ and $Ar^2$ are connected to the parent molecular moiety through any substitutable carbon atoms of the monocyclic heteroaryl moiety of the group. The nitrogen and sulfur heteroatoms of the heteroaryl rings of present compounds may optionally be oxidized, and are contemplated within the scope of the invention.

The term "heterocycle" or "heterocyclic" as used herein, means a monocyclic or a bicyclic, or a spirocyclic ring system containing at least one heteroatom. The monocyclic heterocycle is a 3-, 4- 5-, 6-, 7-, or 8-membered monocyclic ring containing at least one heteroatom independently selected from the group consisting of O, N, and S. The 3- or 4-membered ring contains 1 heteroatom selected from the group consisting of O, N and S, and optionally one double bond. The 5-membered ring contains zero or one double bond, and one, two or three heteroatoms in the ring selected from the group consisting of O, N and S. The 6-, 7-, or 8-membered ring contains zero, one, or two double bonds, and one, two, or three heteroatoms in the ring selected from the group consisting of O, N and S. Non-limiting examples of monocyclic heterocycles include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, thiopyranyl, and trithianyl. The bicyclic heterocycle is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Non-limiting examples of bicyclic heterocycle include, but are not limited to, 1,3-benzodioxol-4-yl, 1,3-benzodithiolyl, 2,3-dihydro-1,4-benzodioxinyl, dihydrobenzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 3-, 4-, 5-, or 6-membered monocyclic cycloalkyl or monocyclic heterocycle. One example of a spiroheterocycle is 5-oxaspiro[3,4]octane. The monocyclic, bicyclic and spirocyclic heterocycle groups are connected to the parent molecular moiety through any substitutable carbon atom or any substitutable nitrogen atom contained within the group. The monocyclic or bicyclic heterocycle groups may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$] decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane. The nitrogen and sulfur heteroatoms in the heterocycle rings may optionally be oxidized (e.g. 1,1-dioxidothiomorpholinyl (thiomorpholine sulfone)), and the nitrogen atoms may optionally be quarternized.

If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 5 non-hydrogen radicals, then any heteroaryl with less than 5 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical.

The term "oxo" as used herein, means =O.

The terms "treat", "treating," and "treatment" refer to a method of alleviating or abrogating a disease and/or its attendant symptoms.

The terms "prevent", "preventing," and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

b. Compounds

IGF-1R inhibitors have formula (I) as described in the Summary.

Particular values of variable groups in compounds of formula (I) are as follows. Such values may be used where appropriate with any of the other values, definitions, claims or embodiments defined hereinbefore or hereinafter.

In compounds of formula (I), ring $G^1$ has values as disclosed in the Summary.

In certain embodiments, ring $G^1$ is formula (i). Thus, examples of compounds include herein, but not limited to, are those of formula (I-i)

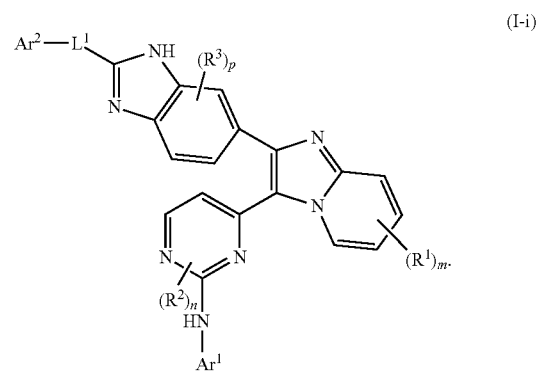

Other embodiments provide compounds of formula (I) wherein $G^1$ is formula (ii). Examples include, but not limited to, are those having formula (I-ii)

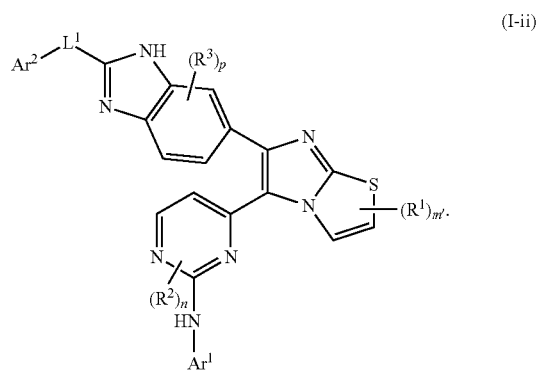

Yet other embodiments include those wherein ring $G^1$ is formula (iii) such as those of formula (I-iii)

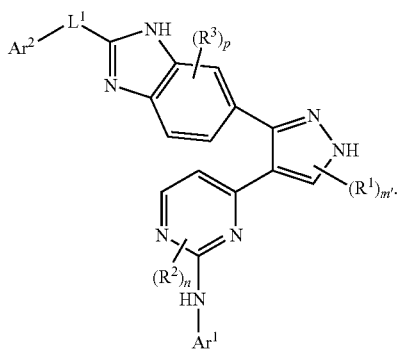

(I-iii)

Still another class of compounds of formula (I) include those wherein $G^1$ is formula (Iv), such as those of formula (I-iv)

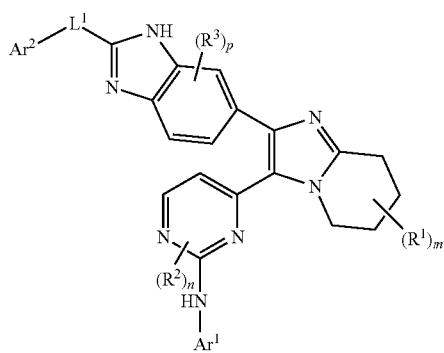

(I-iv)

Variables $Ar^1$, $Ar^2$, $R^1$, $R^2$, $R^3$, m, m' n, p, and $L^1$ for compounds of formula (I-i), (I-ii), (I-iii), and (I-iv) are as disclosed above in the Summary and below in the Detailed Description sections.

$R^1$, $R^2$, and $R^3$ are optional substituents on any substitutable atoms within the rings unless noted otherwise.

In conjunction with any above or below embodiments, the variable m for compounds of formula (I), (I-i), and (I-iv) has meanings as provided for in the Summary section. For example, one embodiment pertains to compounds of formula (I), (I-i), or (I-iv) wherein m is 0. In one embodiment of compounds of formula (I), (I-i), or (I-iii), m is 1 or 2.

In conjunction with any above or below embodiments, m' for compounds of formula (I), (I-ii), and (I-iii) has meanings as provided for in the Summary section. For example, one class of compounds of formula (I), (I-ii), and (I-iii) include those defined wherein m' is 0 or 1.

One class of compounds of formula (I), (I-i), (I-ii), (I-iii), or (I-iv) includes those defined wherein each of the optional substituent, $R^1$, when present, is independently $C_{1-6}$ alkyl, halogen, or $C_{1-6}$ haloalkyl. In one embodiment, each of the optional substituent, $R^1$, when present, is $C_{1-6}$ alkyl. For example, $R^1$, when present, is methyl or ethyl.

In conjunction with any above or below embodiments, the variable 'n' for compounds of formula (I), (I-i), (I-ii), (I-iii), or (I-iv) has meanings as disclosed in the Summary, for example, n is 0. In certain class of compounds of formula (I), (I-i), (I-ii), (I-iii), or (I-iv), n is 1 or 2.

In the class of compounds of formula (I), (I-i), (I-ii), (I-iii), or (I-iv) wherein n is 1 or 2, $R^2$ is as defined in the Summary.

In certain embodiments, each $R^2$, when present, is independently $C_{1-6}$ alkyl, halogen, or $C_{1-6}$ haloalkyl. In one embodiment, the optional substituent $R^2$, when present, is $C_{1-6}$ alkyl. For example, $R^2$ is methyl.

In one class of compounds of formula (I), (I-i), (I-ii), (I-iii), or (I-iv), p is 0. In another class of compounds, p is 1 or 2.

In the class of compounds of formula (I), (I-i), (I-ii), (I-iii), or (I-iv) wherein p is 1 or 2, $R^3$ is substituted on the phenyl ring of the benzimidazoyly moiety and has meanings as defined in the Summary. For example, in certain embodiments, each of the optional substituents $R^3$, when present, is independently selected from the group consisting of $C_{1-6}$ alkyl, halogen, $-O(C_{1-6}$ alkyl), $-O(C_{1-6}$ haloalkyl), and $C_{1-6}$ haloalkyl. For example, when present, each $R^3$ is independently selected from the group consisting of methyl, ethyl, F, Cl, —O(methyl), —O(trifluoromethyl), and trifluoromethyl.

$L^1$ for compounds of formula (I), (I-i), (I-ii), (I-iii), or (I-iv) has meanings as set forth in the Summary. In one class of compounds of formula (I), (I-i), (I-ii), (I-iii), or (I-iv), $L^1$ is a bond. In certain embodiments, $L^1$ is N(H). In other embodiments, $L^1$ is $(CR^4R^5)_q$ wherein $R^4$, $R^5$, and q are as described in the Summary and embodiments herein.

One class of compounds of formula (I), (I-i), (I-ii), (I-iii), or (I-iv) includes those wherein q is 1 or 2. In certain embodiments, q is 1.

$R^4$ and $R^5$ have values as disclosed in the Summary. In conjunction with any above or below embodiments of compounds of formula (I), (I-i), (I-ii), (I-iii), or (I-iv), $R^4$ and $R^5$ are the same or different, and are each independently selected from the group consisting of hydrogen and alkyl (for example, $C_{1-6}$ alkyl such as, but not limited to, methyl). In one embodiment, $R^4$ and $R^5$ are both hydrogen. In another embodiment, one of $R^4$ and $R^5$ is hydrogen, and the other is $C_{1-6}$ alkyl such as, but not limited to, methyl.

$Ar^2$ has values as described in the Summary. In one embodiment, $Ar^2$ is optionally substituted aryl. In another embodiment, $Ar^2$ is optionally substituted heteroaryl. In yet another embodiment, $Ar^2$ is optionally substituted phenyl. In a further embodiment, $Ar^2$ is optionally substituted monocyclic heteroaryl.

The optional substituents of $Ar^2$ are as defined in the Summary. In conjunction with any above or below embodiments of compounds of formula (I), (I-i), (I-ii), (I-iii), or (I-iv), each of these optional substituents of $Ar^2$ can be the same or different and are, for example, independently alkyl (e.g. $C_{1-6}$ alkyl such as but not limited to, methyl), halogen (e.g. Cl, F, and the like), haloalkyl (e.g. $C_{1-6}$ haloalkyl such as but not limited to, trifluoromethyl), or $-OR^{Z1}$, wherein $R^{Z1}$ is as disclosed in the Summary. In certain embodiments, $R^{Z1}$ is $C_{1-6}$ alkyl such as but not limited to, methyl.

$Ar^1$ has values as described in the Summary. For example, in conjunction with any above or below embodiments of compounds of formula (I), (I-i), (I-ii), (I-iii), or (1-iv), $Ar^1$ is phenyl or monocyclic heteroaryl, each of which is optionally substituted as described in the Summary and Detailed Description sections. In one embodiment, $Ar^1$ is optionally substituted aryl. In another embodiment, $Ar^1$ is an optionally substituted heteroaryl, for example, an optionally substituted monocyclic heteroaryl. In yet another embodiment, $Ar^1$ is optionally substituted phenyl. In still another embodiment, $Ar^1$ is optionally substituted pyrazolyl or pyridinyl.

The optional substituents of $Ar^1$ are as defined in the Summary. For example, in conjunction with any above or below embodiments of compounds of formula (I), (I-i), (I-ii), (I-iii), or (I-iv), each of the optional substituents of $Ar^1$ are the same or different, and when present are each independently alkyl (e.g. $C_{1-6}$ alkyl such as, but not limited to, methyl), halogen (e.g. F, Cl, and the like), haloalkyl (e.g. $C_{1-6}$ haloalkyl such as, but not limited to, trifluoromethyl), $G^2$ (e.g. heterocycle such as, but not limited to, morpholinyl, piperazinyl, pyrrolidinyl, thiomorpholinyl, piperidinyl, and the like; and $C_{3-6}$ monocyclic cycloalkyl such as, but not limited to, cyclopropyl; each of these rings is optionally substituted as described in the Summary), $-OR^6$, $-S(O)_2R^7$, $-S(O)_2N(R^8)(R^9)$, $-N(R^8)(R^9)$, $-N(R^8)C(O)-(C_{1-6}$ alkylenyl)-$N(R^8)(R^9)$, $-(C_{1-6}$ alkylenyl)-$G^2$ ($G^2$, for example, is heterocycle such as, but not limited to, morpholinyl, piperazinyl, pyrrolidinyl, thiomorpholinyl, piperidinyl, each of which is optionally substituted as described in the Summary), $-(C_{1-6}$ alkylenyl)-$OR^6$, or $-(C_{1-6}$ alkylenyl)-$N(R^8)(R^9)$ wherein $R^6$, $R^7$, $R^8$, and $R^9$ are as described in the Summary. When $Ar^1$ is phenyl, two substituents on the vicinal carbon atoms of $Ar^1$, together with the carbon atoms to which they are attached, may form a monocyclic heterocycle ring as described in the Summary, for example, they may form a monocyclic heterocycle such as

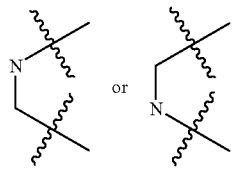

wherein each of these rings is optionally substituted as described in the Summary.

It is appreciated that compounds of formula (I), (I-i), (I-ii), (I-iii), and (I-iv) with combinations of the above embodiments and subsets of the particular groups defined, including particular, more particular and preferred embodiments are contemplated.

Accordingly, one aspect relates to a group of compounds of formula (I), (I-i), (I-ii), (I-iii), or (I-iv) wherein $L^1$ is a bond, and $Ar^2$ is optionally substituted aryl.

Another aspect relates to a group of compounds of formula (I), (I-i), (I-ii), (I-iii), or (I-iv) wherein $L^1$ is N(H), and $Ar^2$ is optionally substituted aryl.

Yet another aspect relates to a group of compounds of formula (I), (I-i), (I-ii), (I-iii), or (I-iv) wherein $L^1$ is $(CR^4R^5)_q$, and $Ar^2$ is optionally substituted aryl.

Still another aspect relates to a group of compounds of formula (I), (I-i), (I-ii), (I-iii), or (I-iv) wherein $L^1$ is a bond, and $Ar^2$ is optionally substituted heteroaryl.

Another aspect relates to a group of compounds of formula (I), (I-i), (I-ii), (I-iii), or (I-iv) wherein $L^1$ is N(H), and $Ar^2$ is optionally substituted heteroaryl.

Yet another aspect relates to a group of compounds of formula (I), (I-i), (I-ii), (I-iii), or (I-iv) wherein $L^1$ is $(CR^4R^5)_q$, and $Ar^2$ is optionally substituted heteroaryl.

Still another aspect relates to a group of compounds of formula (I), (I-i), (I-ii), (I-iii), or (I-iv) wherein $L^1$ is a bond, and $Ar^2$ is optionally substituted phenyl.

Another aspect relates to a group of compounds of formula (I), (I-i), (I-ii), (I-iii), or (I-iv) wherein $L^1$ is N(H), and $Ar^2$ is optionally substituted phenyl.

Yet another aspect relates to a group of compounds of formula (I), (I-i), (I-ii), (I-iii), or (I-iv) wherein $L^1$ is $(CR^4R^5)_q$, and $Ar^2$ is optionally substituted phenyl.

Within each group of compounds of formula (I), (I-i), (I-ii), (I-iii), or (I-iv) as described in the preceding paragraphs, $Ar^1$, $R^1$, $R^2$, $R^3$, $R^4$, $R^5$, m, m', n, p, q, and the optional substituents of $Ar^1$ and $Ar^2$, are as described in the Summary and Detailed Description.

Thus, of each group of compounds of formula (I), (I-i), (I-ii), (I-iii), or (I-iv) as described in the preceding paragraphs, examples of a subgroup include those wherein $Ar^1$ is phenyl or monocyclic heteroaryl, each of which is optionally substituted.

Examples of another subgroup of compounds of formula (I), (I-i), (I-ii), (I-iii), or (I-iv) include those wherein $Ar^1$ is optionally substituted aryl.

Examples of another subgroup of compounds of formula (I), (I-i), (I-ii), (I-iii), or (I-iv) include those wherein $Ar^1$ is optionally substituted phenyl.

Yet other examples of a subgroup of compounds of formula (I), (I-i), (I-ii), (I-iii), or (I-iv) include those wherein $Ar^1$ is optionally substituted heteroaryl.

Further examples of a subgroup of compounds of formula (I), (I-i), (I-ii), (I-iii), or (I-iv) include those wherein $Ar^1$ is optionally substituted monocyclic heteroaryl (for example, but not limited thereto, pyrazolyl, pyridinyl, each of which is optionally substituted).

For each of the groups and subgroups of compounds of formula (I), (I-i), (I-ii), (I-iii), or (I-iv) described above, $R^1$, $R^2$, $R^3$, $R^4$, $R^5$, m, m', n, p, q, and the optional substituents of $Ar^1$ and $Ar^2$, are as described in the Summary and Detailed Description. For example, in one embodiment, n, m, and p are 0, and m' is 0 or 1. In other embodiments, examples include, but are not limited to, those wherein m and n are 0, p is 1 or 2, m' is 0 or 1; $R^3$ is selected from the group consisting of $C_{1-6}$ alkyl, halogen, $-O(C_{1-6}$ alkyl), $-O(C_{1-6}$ haloalkyl), and $C_{1-6}$ haloalkyl. For example, $R^3$ is selected from the group consisting of methyl, ethyl, F, Cl, $-O$(methyl), $-O$(trifluoromethyl), and trifluoromethyl. Yet other examples include, but are not limited to, those wherein m and n are 0, p is 1, m' is 0 or 1; and $R^3$ is $-O(C_{1-6}$ alkyl) (e.g. $-O$(methyl)).

For each of the groups and subgroups of compounds of formula (I), (I-i), (I-ii), (I-iii), or (I-iv) described above, $R^4$, $R^5$, and q are as described in the Summary and Detailed description. For example, q is 1 or 2. In certain embodiments, q is 1. For example, $R^4$ and $R^5$ are the same or different, and are each independently selected from the group consisting of hydrogen and alkyl (for example, $C_{1-6}$ alkyl such as, but not limited to, methyl). In other embodiment, $R^4$ and $R^5$ are both hydrogen. In another embodiment, one of $R^4$ and $R^5$ is hydrogen, and the other is $C_{1-6}$ alkyl such as, but not limited to, methyl.

Non limiting examples of compounds of formula (I), (I-i), (I-ii), (I-iii), and (I-iv) include, but are not limited to, 1-[3-({4-[2-(2-benzyl-1H-benzimidazol-5-yl)imidazo[1,2-a]pyridin-3-yl]pyrimidin-2-yl}amino)phenyl]pyrrolidin-2-one;

4-[2-(2-benzyl-1H-benzimidazol-6-yl)imidazo[1,2-a]pyridin-3-yl]-N-{3-[2-(dimethylamino)ethyl]phenyl}pyrimidin-2-amine;

N-{3-[2-(dimethylamino)ethyl]phenyl}-4-{2-[2-(2-methoxybenzyl)-1H-benzimidazol-5-yl]imidazo[1,2-a]pyridin-3-yl}pyrimidin-2-amine;

4-[2-(2-benzyl-1H-benzimidazol-5-yl)imidazo[1,2-a]pyridin-3-yl]-N-phenylpyrimidin-2-amine;

4-{2-[2-(2-chlorobenzyl)-1H-benzimidazol-5-yl]imidazo[1,2-a]pyridin-3-yl}-N-{3-[2-(dimethylamino)ethyl]phenyl}pyrimidin-2-amine;

N-{3-[2-(dimethylamino)ethyl]phenyl}-4-(2-{2-[2-(trifluoromethyl)benzyl]-1H-benzimidazol-5-yl}imidazo[1,2-a]pyridin-3-yl)pyrimidin-2-amine;

4-[6-(2-benzyl-1H-benzimidazol-6-yl)imidazo[2,1-b][1,3]
thiazol-5-yl]-N-{3-[2-(dimethylamino)ethyl]
phenyl}pyrimidin-2-amine;
N-{3-[2-(dimethylamino)ethyl]phenyl}-4-{6-[2-(2-methoxybenzyl)-1H-benzimidazol-6-yl]imidazo[2,1-b][1,3]
thiazol-5-yl}pyrimidin-2-amine;
4-{6-[2-(2-chlorobenzyl)-1H-benzimidazol-6-yl]imidazo[2,1-b][1,3]thiazol-5-yl}-N-{3-[2-(dimethylamino)ethyl]
phenyl}pyrimidin-2-amine;
N-{3-[2-(dimethylamino)ethyl]phenyl}-4-{2-[2-(2-phenylethyl)-1H-benzimidazol-6-yl]imidazo[1,2-a]pyridin-3-yl}pyrimidin-2-amine;
N-phenyl-4-[2-(2-phenyl-1H-benzimidazol-6-yl)imidazo[1,2-a]pyridin-3-yl]pyrimidin-2-amine;
6-{3-[2-({3-[2-(dimethylamino)ethyl]phenyl}amino)pyrimidin-4-yl]imidazo[1,2-a]pyridin-2-yl}-N-phenyl-1H-benzimidazol-2-amine;
N-{3-[2-(dimethylamino)ethyl]phenyl}-4-[2-(2-phenyl-1H-benzimidazol-6-yl)imidazo[1,2-a]pyridin-3-yl]pyrimidin-2-amine;
4-[2-(2-benzyl-1H-benzimidazol-6-yl)imidazo[1,2-a]pyridin-3-yl]-N-(2-methoxy-4-morpholin-4-ylphenyl)pyrimidin-2-amine;
4-[2-(2-benzyl-1H-benzimidazol-6-yl)imidazo[1,2-a]pyridin-3-yl]-N-(2-methoxyphenyl)pyrimidin-2-amine;
4-[2-(2-benzyl-1H-benzimidazol-6-yl)imidazo[1,2-a]pyridin-3-yl]-N-[3-(methylsulfonyl)phenyl]pyrimidin-2-amine;
3-({4-[2-(2-benzyl-1H-benzimidazol-6-yl)imidazo[1,2-a]pyridin-3-yl]pyrimidin-2-yl}amino)-N,N-dimethylbenzenesulfonamide;
4-[2-(2-benzyl-1H-benzimidazol-6-yl)imidazo[1,2-a]pyridin-3-yl]-N-[4-(methylsulfonyl)phenyl]pyrimidin-2-amine;
6-[3-(2-anilinopyrimidin-4-yl)imidazo[1,2-a]pyridin-2-yl]-N-phenyl-1H-benzimidazol-2-amine;
4-{2-[2-(2-methoxybenzyl)-1H-benzimidazol-6-yl]imidazo[1,2-a]pyridin-3-yl}-N-(2-methoxy-4-morpholin-4-ylphenyl)pyrimidin-2-amine;
4-{2-[2-(2,6-difluorobenzyl)-1H-benzimidazol-6-yl]imidazo[1,2-a]pyridin-3-yl}-N-(2-methoxy-4-morpholin-4-ylphenyl)pyrimidin-2-amine;
4-[2-(2-benzyl-1H-benzimidazol-5-yl)imidazo[1,2-a]pyridin-3-yl]-N-{2-methoxy-4-[4-(4-methylpiperazin-1-yl)piperidin-1-yl]phenyl}pyrimidin-2-amine;
4-[6-(2-benzyl-1H-benzimidazol-6-yl)imidazo[2,1-b][1,3]thiazol-5-yl]-N-phenylpyrimidin-2-amine;
4-[6-(2-benzyl-1H-benzimidazol-6-yl)imidazo[2,1-b][1,3]thiazol-5-yl]-N-(2-methoxyphenyl)pyrimidin-2-amine;
4-[2-(2-benzyl-1H-benzimidazol-6-yl)imidazo[1,2-a]pyridin-3-yl]-N-(5-methyl-1H-pyrazol-3-yl)pyrimidin-2-amine;
4-[2-(2-benzyl-1H-benzimidazol-6-yl)imidazo[1,2-a]pyridin-3-yl]-N-(3-cyclopropyl-1H-pyrazol-5-yl)pyrimidin-2-amine;
N-(2-methoxy-4-morpholin-4-ylphenyl)-4-[2-(2-phenyl-1H-benzimidazol-6-yl)imidazo[1,2-a]pyridin-3-yl]pyrimidin-2-amine;
4-[2-(2-benzyl-1H-benzimidazol-5-yl)-5,6,7,8-tetrahydroimidazo[1,2-a]pyridin-3-yl]-N-phenylpyrimidin-2-amine;
3-({4-[2-(2-benzyl-1H-benzimidazol-5-yl)imidazo[1,2-a]pyridin-3-yl]pyrimidin-2-yl}amino)pyridin-2(1H)-one;
4-[6-(2-benzyl-1H-benzimidazol-6-yl)imidazo[2,1-b][1,3]thiazol-5-yl]-N-{-4-[4-(dimethylamino)piperidin-1-yl]-2-methoxyphenyl}pyrimidin-2-amine;
$N^1$-{4-[6-(2-benzyl-1H-benzimidazol-6-yl)imidazo[2,1-b][1,3]thiazol-5-yl]pyrimidin-2-yl}-2-methoxy-$N^4,N^4$-dimethylbenzene-1,4-diamine;
4-[2-(2-benzyl-1H-benzimidazol-6-yl)imidazo[1,2-a]pyridin-3-yl]-N-(4-chloro-2-methoxyphenyl)pyrimidin-2-amine;
$N^1$-(4-{6-[2-(2-chlorobenzyl)-1H-benzimidazol-6-yl]imidazo[2,1-b][1,3]thiazol-5-yl}pyrimidin-2-yl)-2-methoxy-$N^4,N^4$-dimethylbenzene-1,4-diamine;
2-methoxy-$N^1$-(4-{6-[2-(2-methoxybenzyl)-1H-benzimidazol-6-yl]imidazo[2,1-b][1,3]thiazol-5-yl}pyrimidin-2-yl)-$N^4,N^4$-dimethylbenzene-1,4-diamine;
4-[2-(2-benzyl-1H-benzimidazol-5-yl)imidazo[1,2-a]pyridin-3-yl]-N-(1-methyl-1H-pyrazol-4-yl)pyrimidin-2-amine;
2-[4-({4-[2-(2-phenyl-1H-benzimidazol-5-yl)imidazo[1,2-a]pyridin-3-yl]pyrimidin-2-yl}amino)-1H-pyrazol-1-yl]ethanol;
2-[4-({4-[2-(2-benzyl-1H-benzimidazol-5-yl)imidazo[1,2-a]pyridin-3-yl]pyrimidin-2-yl}amino)-1H-pyrazol-1-yl]ethanol;
N-(4-fluorophenyl)-4-[2-(2-phenyl-1H-benzimidazol-6-yl)imidazo[1,2-a]pyridin-3-yl]pyrimidin-2-amine;
4-[2-(2-benzyl-1H-benzimidazol-5-yl)imidazo[1,2-a]pyridin-3-yl]-N-(4-fluorophenyl)pyrimidin-2-amine;
N-(2,4-difluorophenyl)-4-[2-(2-phenyl-1H-benzimidazol-6-yl)imidazo[1,2-a]pyridin-3-yl]pyrimidin-2-amine;
4-[2-(2-benzyl-1H-benzimidazol-5-yl)imidazo[1,2-a]pyridin-3-yl]-N-(2,4-difluorophenyl)pyrimidin-2-amine;
N-[2-(pyrrolidin-1-ylmethyl)phenyl]-4-(6-{2-[2-(trifluoromethyl)benzyl]-1H-benzimidazol-6-yl}imidazo[2,1-b][1,3]thiazol-5-yl)pyrimidin-2-amine;
4-[2-(2-benzyl-1H-benzimidazol-6-yl)imidazo[1,2-a]pyridin-3-yl]-N-[2-methoxy-5-(methylsulfonyl)phenyl]pyrimidin-2-amine;
N-(1-methyl-1H-pyrazol-4-yl)-4-[2-(2-phenyl-1H-benzimidazol-5-yl)imidazo[1,2-a]pyridin-3-yl]pyrimidin-2-amine;
4-[2-(2-benzyl-1H-benzimidazol-6-yl)imidazo[1,2-a]pyridin-3-yl]-N-[2-methoxy-5-(trifluoromethyl)phenyl]pyrimidin-2-amine;
N-{4-[(dimethylamino)methyl]phenyl}-4-(6-{2-[2-(trifluoromethyl)benzyl]-1H-benzimidazol-6-yl}imidazo[2,1-b][1,3]thiazol-5-yl)pyrimidin-2-amine;
1-{[4-({4-[2-(2-benzyl-1H-benzimidazol-5-yl)imidazo[1,2-a]pyridin-3-yl]pyrimidin-2-yl}amino)-3-methoxyphenyl]amino}-2-methylpropan-2-ol;
2-[[4-({4-[2-(2-benzyl-1H-benzimidazol-6-yl)imidazo[1,2-a]pyridin-3-yl]pyrimidin-2-yl}amino)-3-methoxyphenyl](methyl)amino]ethanol;
N-[4-({4-[2-(2-benzyl-1H-benzimidazol-5-yl)imidazo[1,2-a]pyridin-3-yl]pyrimidin-2-yl}amino)-3-methoxyphenyl]glycine;
2-[[3-({4-[2-(2-benzyl-1H-benzimidazol-6-yl)imidazo[1,2-a]pyridin-3-yl]pyrimidin-2-yl}amino)-4-methoxybenzyl](methyl)amino]ethanol;
$N^1$-[3-({4-[2-(2-benzyl-1H-benzimidazol-6-yl)imidazo[1,2-a]pyridin-3-yl]pyrimidin-2-yl}amino)phenyl]-$N^2,N^2$-dimethylglycinamide;
N-{4-[4-(dimethylamino)piperidin-1-yl]-2-methoxyphenyl}-4-(6-{2-[2-(trifluoromethyl)benzyl]-1H-benzimidazol-6-yl}imidazo[2,1-b][1,3]thiazol-5-yl)pyrimidin-2-amine;
$N^1$-[3-({4-[2-(2-benzyl-1H-benzimidazol-6-yl)imidazo[1,2-a]pyridin-3-yl]pyrimidin-2-yl}amino)-4-methoxyphenyl]-$N^2,N^2$-dimethylglycinamide;

4-{6-[2-(2-chlorobenzyl)-1H-benzimidazol-6-yl]imidazo[2,1-b][1,3]thiazol-5-yl}-N-{4-[4-(dimethylamino)piperidin-1-yl]-2-methoxyphenyl}pyrimidin-2-amine;

N-{4-[4-(dimethylamino)piperidin-1-yl]-2-methoxyphenyl}-4-{6-[2-(2-methoxybenzyl)-1H-benzimidazol-6-yl]imidazo[2,1-b][1,3]thiazol-5-yl}pyrimidin-2-amine;

N-{4-[4-(dimethylamino)piperidin-1-yl]-2-methoxyphenyl}-4-{6-[2-(2-methylbenzyl)-1H-benzimidazol-6-yl]imidazo[2,1-b][1,3]thiazol-5-yl}pyrimidin-2-amine;

4-[6-(2-benzyl-1H-benzimidazol-6-yl)imidazo[2,1-b][1,3]thiazol-5-yl]-N-{4-[(dimethylamino)methyl]phenyl}pyrimidin-2-amine;

4-[6-(2-benzyl-1H-benzimidazol-6-yl)imidazo[2,1-b][1,3]thiazol-5-yl]-N-{2-[(dimethylamino)methyl]phenyl}pyrimidin-2-amine;

1-{3-[(4-{3-[2-(2-chlorobenzyl)-1H-benzimidazol-5-yl]-1H-pyrazol-4-yl}pyrimidin-2-yl)amino]phenyl}pyrrolidin-2-one;

N-{3-[(dimethylamino)methyl]phenyl}-4-{1-ethyl-3-[2-(2-methoxybenzyl)-1H-benzimidazol-5-yl]-1H-pyrazol-4-yl}pyrimidin-2-amine;

4-{3-[2-(2-chlorobenzyl)-1H-benzimidazol-5-yl]-1-ethyl-1H-pyrazol-4-yl}-N-{3-[(dimethylamino)methyl]phenyl}pyrimidin-2-amine;

5-{4-[2-({3-[(dimethylamino)methyl]phenyl}amino)pyrimidin-4-yl]-1-ethyl-1H-pyrazol-3-yl}-N-phenyl-1H-benzimidazol-2-amine;

4-[3-(2-benzyl-1H-benzimidazol-5-yl)-1-ethyl-1H-pyrazol-4-yl]-N-{3-[(dimethylamino)methyl]phenyl}pyrimidin-2-amine;

4-[3-(2-benzyl-1H-benzimidazol-5-yl)-1-ethyl-1H-pyrazol-4-yl]-N-(2-methoxyphenyl)pyrimidin-2-amine;

4-{1-ethyl-3-[2-(2-methoxybenzyl)-1H-benzimidazol-5-yl]-1H-pyrazol-4-yl}-N-(2-methoxyphenyl)pyrimidin-2-amine;

4-[3-(2-benzyl-1H-benzimidazol-5-yl)-1-ethyl-1H-pyrazol-4-yl]-N-{4-[4-(dimethylamino)piperidin-1-yl]-2-methoxyphenyl}pyrimidin-2-amine;

4-{3-[2-(2-chlorobenzyl)-1H-benzimidazol-5-yl]-1-ethyl-1H-pyrazol-4-yl}-N-{4-[4-(dimethylamino)piperidin-1-yl]-2-methoxyphenyl}pyrimidin-2-amine;

N-{4-[4-(dimethylamino)piperidin-1-yl]-2-methoxyphenyl}-4-{1-ethyl-3-[2-(2-methoxybenzyl)-1H-benzimidazol-5-yl]-1H-pyrazol-4-yl}pyrimidin-2-amine; and N-{4-[4-(dimethylamino)piperidin-1-yl]-2-methoxyphenyl}-4-[1-ethyl-3-(2-phenyl-1H-benzimidazol-5-yl)-1H-pyrazol-4-yl]pyrimidin-2-amine;

or pharmaceutically acceptable salts or solvates thereof.

Compounds of the present application may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

It will be appreciated that two or more asymmetric centers may be present in the present compounds, hence several diastereomers and enantiomers of the exemplified structures will often be possible. It is intended that pure diasteromers, pure enantiomers, and mixtures thereof, are within the scope of the invention.

Various stereoisomers (including enantiomers and diastereomers) and mixtures thereof (including racemates) are contemplated. Individual stereoisomers of present compounds may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. Thus various geometric isomers and mixtures thereof resulting from the disposition of substituents around a carbon-carbon double bond, a carbon-nitrogen double bond, a cycloalkyl group, or a heterocycle group are part of the invention. Substituents around a carbon-carbon double bond or a carbon-nitrogen bond are designated as being of Z or E configuration and substituents around a cycloalkyl or a heterocycle are designated as being of cis or trans configuration.

Within the present application it is to be understood that compounds disclosed hererin may exist as individual tautomers or equilibrium mixtures thereof wherein a proton of a compound shifts from one atom to another.

Though structural representations within this specification may show only one of the possible tautomeric or stereoisomeric forms, it is to be understood that the invention encompasses any tautomeric or stereoisomeric form, and mixtures thereof, and is not to be limited merely to any one tautomeric or stereoisomeric form utilized within the naming of the compounds or drawings.

The present compounds can exist in radiolabeled or isotope labeled form containing one or more atoms having an atomic mass or mass number different from the atomic mass or mass number most abundantly found in nature. Isotopes of atoms such as hydrogen, carbon, phosphorous, sulfur, fluorine, chlorine, and iodine include, but are not limited to, $^{2}H$, $^{3}H$, $^{14}C$, $^{32}P$, $^{35}S$, $^{18}F$, $^{36}Cl$, and $^{125}I$. Compounds that contain other radioisotopes of these and/or other atoms are within the scope of this invention. In one embodiment, the isotope-labeled compounds contain deuterium ($^{2}H$), tritium ($^{3}H$) or $^{14}C$ radioisotopes. Isotope and radiolabeled compounds of this invention can be prepared by the general methods well known to persons having ordinary skill in the art. Such isotope and radiolabeled compounds can be conveniently prepared by carrying out the procedures disclosed in the above Examples and Schemes by substituting a readily available isotope or radiolabeled reagent for a non-labeled reagent. The isotope and radiolabeled compounds of the invention may be used as standards to determine the effectiveness of IGF-IR ligands or modulators in the binding assays. The isotope and radiolabeled compounds of the invention or pharmaceutically acceptable salts or solvates thereof may also be used for treating or preventing diseases or conditions described herein.

c. Biological Data

The following example describes the assay that may be used to identify compounds having kinase activity.

IGF-1R kinase activity was assayed by a homogenous time-resolved fluorescence (HTRF) in vitro kinase assay (Mathis, G., HTRF(R) Technology. J Biomol Screen, 1999. 4(6): p. 309-314). Specifically, 10 μL C-terminal GST-tagged, recombinant, human IGF-1R, amino acids 954-1367 expressed by baculovirus in Sf21 cells (Cell Signaling Technology) was mixed with 10 μL inhibitor (various concentrations, 2% final DMSO) and 10 μL of ATP (50 μM final concentration) in reaction buffer (50 mM HEPES, pH 7.5, 10 mM $MgCl_2$, 2 mM $MnCl_2$, 0.1% BSA and 1 mM DTT, 40 μL final volume). The reaction was initiated by addition of 10 μL of biotinylated peptide substrate (Biotin-Ahx-AEEEYF- FLFA, 0.5 µM final concentration) in a black 384-well plate (Packard). After 60 minutes incubation at room temperature, the reaction was quenched by addition of 60 µL stop/revelation buffer to give 30 mM EDTA, 1 µg/mL streptavidin-APC (Prozyme), 50 ng/mL anti-phosphotyrosine mAb PT66-K Europium Cryptate, 30 mM HEPES, pH 7.5, 120 mM KF, 0.005% Tween-20, 0.05% BSA). The quenched reaction was allowed to stand at room temperature for 1 hour and then read in a time-resolved fluorescence detector (Envision, Perkin Elmer) at 615 nm and 665 nm simultaneously. The ratio between the signal of 615 nm and 665 nm was used in the calculation of the $IC_{50}$.

Table 1 demonstrates the utility of the representative examples of compounds described herein as inhibitors of IGF-1R kinases. In Table 1, "A" represents $IC_{50}$ of less than 10 nM; "B" represents $IC_{50}$ of between 10 nM and 50 nM; "C" represents $IC_{50}$ of between 51 nM and 100 nM; "D" represents $IC_{50}$ of between 101 nM and 500 nM; and "E" represents $IC_{50}$ of greater than 500 nM.

TABLE 1

| Example # | $IC_{50}$ |
|---|---|
| 1 | B |
| 2 | A |
| 3 | A |
| 4 | B |
| 5 | A |
| 6 | A |
| 7 | A |
| 8 | A |
| 9 | A |
| 10 | B |
| 11 | D |
| 12 | A |
| 13 | B |
| 14 | A |
| 15 | C |
| 16 | C |
| 17 | D |
| 18 | C |
| 19 | E |
| 20 | C |
| 21 | B |
| 22 | A |
| 23 | C |
| 24 | B |
| 25 | C |
| 26 | B |
| 27 | B |
| 29 | D |
| 30 | A |
| 31 | B |
| 32 | D |
| 33 | B |
| 34 | B |
| 36 | B |
| 37 | B |
| 38 | D |
| 39 | C |
| 40 | E |
| 41 | D |
| 42 | E |
| 43 | B |
| 44 | E |
| 45 | D |
| 46 | B |
| 47 | B |
| 48 | B |
| 49 | B |
| 50 | B |
| 51 | A |
| 52 | A |
| 53 | A |
| 54 | A |
| 55 | A |
| 56 | A |
| 57 | A |
| 58 | E |
| 59 | D |
| 60 | B |
| 61 | B |
| 62 | B |
| 63 | B |
| 64 | D |
| 65 | D |
| 66 | B |
| 67 | C |
| 68 | C |
| 69 | D |

Compounds assessed by the above-described assay were found to have IGF-1R inhibiting activity.

d. Methods of Using the Compounds

In one aspect, the present invention provides methods of using one or more compounds or composition described herein to treat or prevent a disease or condition involving mediation, overexpression or disregulation of IGF-1R kinases in a mammal. In particular, compounds described herein are expected to have utility in treatment of diseases or conditions during which protein kinases such as IGF-1R kinase family members are expressed.

In one group of embodiments, diseases and conditions of humans or other animals that can be treated with inhibitors of IGF-1R kinases, include, but are not limited to, diseases involving overexpression or unregulation of a protein kinase family member such as but not limited to cancer. Cancers include, but are not limited to, hematologic and solid tumor types such as acoustic neuroma, acute leukemia, acute lymphoblastic leukemia, acute myelogenous leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer (including estrogen-receptor positive breast cancer), bronchogenic carcinoma, Burkitt's lymphoma, cervical cancer, chondrosarcoma, chordoma, choriocarcinoma, chronic leukemia, chronic lymphocytic leukemia, chronic myelocytic (granulocytic) leukemia, chronic myelogenous leukemia, colon cancer, colorectal cancer, craniopharyngioma, cystadenocarcinoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, gastric carcinoma, germ cell testicular cancer, gestational trophobalstic disease, glioblastoma, head and neck cancer, heavy chain disease, hemangioblastoma, hepatoma, hepatocellular cancer, hormone insensitive prostate cancer, leiomyosarcoma, liposarcoma, lung cancer (including small cell lung cancer and non-small cell lung cancer), lymphangioendothelio-sarcoma, lymphangiosarcoma, lymphoblastic leukemia, lymphoma (lymphoma, including diffuse large B-cell lymphoma, follicular lymphoma, Hodgkin's lymphoma and non-Hodgkin's lymphoma), malignancies and hyperproliferative disorders of the bladder, breast, colon, lung, ovaries, pancreas, prostate, skin and uterus, lymphoid malignancies of T-cell or B-cell origin, leukemia, medullary carcinoma, medulloblastoma, melanoma, meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, peripheral T-cell lymphoma, pinealoma, polycythemia vera, prostate cancer (including hormone-insensitive (refractory) prostate cancer), rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), stomach cancer, squamous cell carcinoma, synovioma, sweat gland carcinoma, testicular cancer (including germ cell testicular cancer), thyroid cancer, Waldenström's macroglobulinemia, testicular tumors, uterine cancer, Wilms' tumor and the like.

It is also expected that compounds described herein would be useful in treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric osteosarcoma, pediatric rhabdoid kidney tumor, pediatric rhabdomyosarcoma, and pediatric T-cell cancers such as lymphoma and skin cancer and the like.

Involvement of IGF and IGFR in cancer is reported in Nature Reviews Cancer 8, 915 (2008).

The methods of the present invention typically involve administering to a subject in need of therapeutic treatment therapeutically effective amounts of one or more compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

e. Combination Therapy

Further provided herein are methods of using one or more compounds or composition of the invention in combination with one or more additional active agents. Compounds described herein are expected to be useful when used with:

alkylating agents, angiogenesis inhibitors, antibodies, antimetabolites, antimitotics, antiproliferatives, aurora kinase inhibitors, other apoptosis promoters (for example, Bcl-xL, Bcl-w and Bfl-1) inhibitors, Bcr-Abl kinase inhibitors, BiTE (Bi-Specific T cell Engager) antibodies, biologic response modifiers, cyclin-dependent kinase inhibitors, cell cycle inhibitors, cyclooxygenase-2 inhibitors, DVD Ig's, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of apoptosis proteins (IAP's) intercalating antibiotics, kinase inhibitors, mammalian target of rapamycin inhibitors, microRNA's mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, proteosome inhibitors, purine analogs, pyrimidine analogs, receptor tyrosine kinase inhibitors, retinoids/deltoids plant alkaloids, small inhibitory ribonucleic acids (siRNA's), topoisomerase inhibitors, combinations thereof and the like.

A BiTE antibody is a bi-specific antibody that directs T-cells to attach cancer cells by simultaneously binding the two cells. The T-cell then attacks the target cancer cell. Exemplary BiTE antibodies include adecatumumab (Micromet MT201), blinatumomab (Micromet MT103) and the like.

SiRNA's are molecules having endogenous RNA bases or chemically modified nucleotides. The modifications shall not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides or a combination thereof. The siRNA can have varying lengths (10-200 bps) and structures (hairpins, single/double strands, bulges, nicks/gaps, mismatches) and processed in the cell to provide active gene silencing. In certain embodiments, a double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'- and/or the 3'-ends of a given strand.

Multivalent binding proteins are binding proteins comprising two or more antigen binding sites. The multivalent binding protein is preferably engineered to have the three or more antigen binding sites and is generally not a naturally occurring antibody. The term "multispecific binding protein" means a binding protein capable of binding two or more related or unrelated targets. Dual variable domain (DVD) binding proteins are tetravalent or multivalent binding proteins comprising two or more antigen binding sites. Such DVDs may be monospecific, i.e., capable of binding one antigen or multispecific, i.e., capable of binding two or more antigens. DVD binding proteins comprising two heavy chain DVD polypeptides and two light chain DVD polypeptides are referred to as DVD Ig. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (metrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Bcl-2 proteins inhibitors include AT-101 ((−)gossypol), GENASENSE® (G3139 or oblimersen (Bcl-2-targeting antisense oligonucleotide)), IPI-194, IPI-565, N-(4-(4-((4′-chloro(1,1′-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecific antibodies, mAB AR-209, mAB 2B-1 and the like. Histone deacetylase inhibitors include depsipeptide, LAQ-824, MS-275, trapoxin, suberoylanilide hydroxamic acid (SAHA), TSA, valproic acid and the like. HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FCl, PU-3, radicicol, SNX-2112, STA-9090 VER49009 and the like.

Inhibitors of apoptosis proteins include ApoMab (a fully human affinity-matured IgG1 monoclonal antibody), antibodies that target TRAIL or death receptors (e.g., pro-apoptotic receptor agonists DR4 and DR5), conatumumab, ETR2-ST01, GDC0145, (lexatumumab), HGS-1029, LBY-135, PRO-1762 and tratuzumab.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like. Platinum chemotherapeutics include cisplatin, ELOXATIN® (oxaliplatin) eptaplatin, lobaplatin, nedaplatin, PARAPLATIN® (carboplatin), satraplatin and the like. Polo-like kinase inhibitors include BI-2536 and the like.

Thrombospondin analogs include ABT-510, ABT-567, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474) and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX®(WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN®

(aliretinoin), ATRAGEN® (liposomal tretinoin), TARGRETIN® (bexarotene), LGD-1550 and the like.

PARP inhibitors include ABT-888, olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN® (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like. Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Compounds described herein can also be used as radiosensitizeser that enhance the efficacy of radiotherapy. Examples of radiotherapy include external beam radiotherapy, teletherapy, brachtherapy and sealed, unsealed source radiotherapy and the like.

Additionally, compounds described herein may be combined with other chemptherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (Streptomyces staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

Combination therapy includes administration of a single pharmaceutical dosage formulation containing one or more of the compounds and one or more additional pharmaceutical agents, as well as administration of the compounds and each additional pharmaceutical agent in its own separate pharmaceutical dosage formulation. For example, one or more active ingredients (including present compounds and additional pharmaceutical agents) may be administered to the patient together, in a single oral dosage composition having a fixed ratio of each active ingredient, such as a tablet or capsule; or each active ingredient may be administered in separate oral dosage formulations.

Separate dosage formulations may be administered at essentially the same time (e.g., concurrently) or at separately staggered times (e.g., sequentially).

f. Pharmaceutical Compositions

Pharmaceutical compositions comprising compounds described herein or pharmaceutically acceptable salts or solvates thereof are also provided. The pharmaceutical compositions comprise compounds of interest formulated together with one or more non-toxic pharmaceutically acceptable carriers.

Another aspect relates to pharmaceutical compositions comprising compounds described herein, or pharmaceutically acceptable salts or solvates thereof, and one or more pharmaceutically acceptable carriers, alone or in combination with one or more additional active agents.

The pharmaceutical compositions can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions for parenteral injection comprise pharmaceutically acceptable sterile aqueous or non-aqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Present compounds can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration include powders, sprays, ointments and inhalants. The active compound may be mixed under sterile conditions with a pharmaceutically acceptable carrier and any needed preservatives, buffers or propellants which may be required. Ophthalmic formulations, eye ointments, powders and solutions are also contemplated as being within the scope of this invention. This invention also is directed, in part, to all salts of the compounds described herein. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient, the salt preferably is pharmaceutically acceptable and/or physiologically compatible. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethanesulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

Contemplated also are compounds formed by synthetic means or formed by in vivo biotransformation of a prodrug.

Compounds described herein can exist in unsolvated as well as solvated forms, including hydrated forms, such as hemi-hydrates. In general, the solvated forms, with pharmaceutically acceptable solvents such as water and ethanol among others are equivalent to the unsolvated forms.

g. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups $G^1$, $L^1$, $Ar^1$, $Ar^2$, $R^1$, $R^2$, $R^3$, $R^4$, $R^5$, m, m', n, p, and q, have meanings as set forth in the summary section unless otherwise noted, can be synthesized as shown in Schemes 1-5.

Abbreviations which have been used in the descriptions of the Schemes and the Examples that follow are: DMF for N,N-dimethylformamide, and DMSO for dimethyl sulfoxide.

Compounds of formula (I-i) can be prepared as illustrated in Scheme 1.

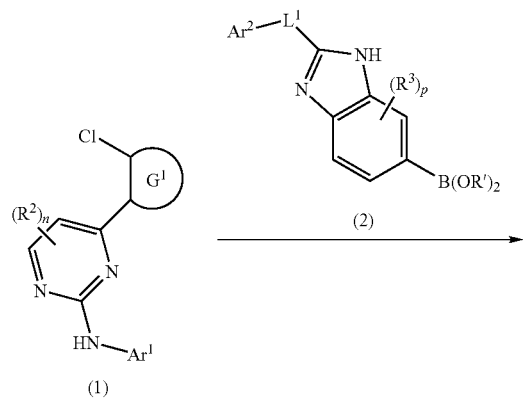

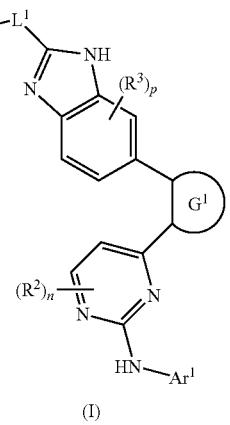

Compounds of formula (I) may be prepared by reacting compounds of formula (I) with an appropriate boronic acids of formula (2) wherein R' is H, or an appropriate boronic esters of formula (2) wherein R' is alkyl. The reaction can be carried out in the presence of a palladium (0) source, a base, and a suitable solvent. Suitable source of palladium (0) includes, but are not limited to, tetrakis(triphenylphosphine)palladium(0). Typical bases for use in the reaction include, for example, cesium carbonate and cesium fluoride. Lower alcohol such as methanol, toluene, 1,2-dimethoxyethane, and mixtures thereof are examples of suitable solvent.

Intermediates of formula (1) wherein $G^1$ is formula (i) used in the foregoing step can be prepared as shown using general procedures as shown in Scheme 2.

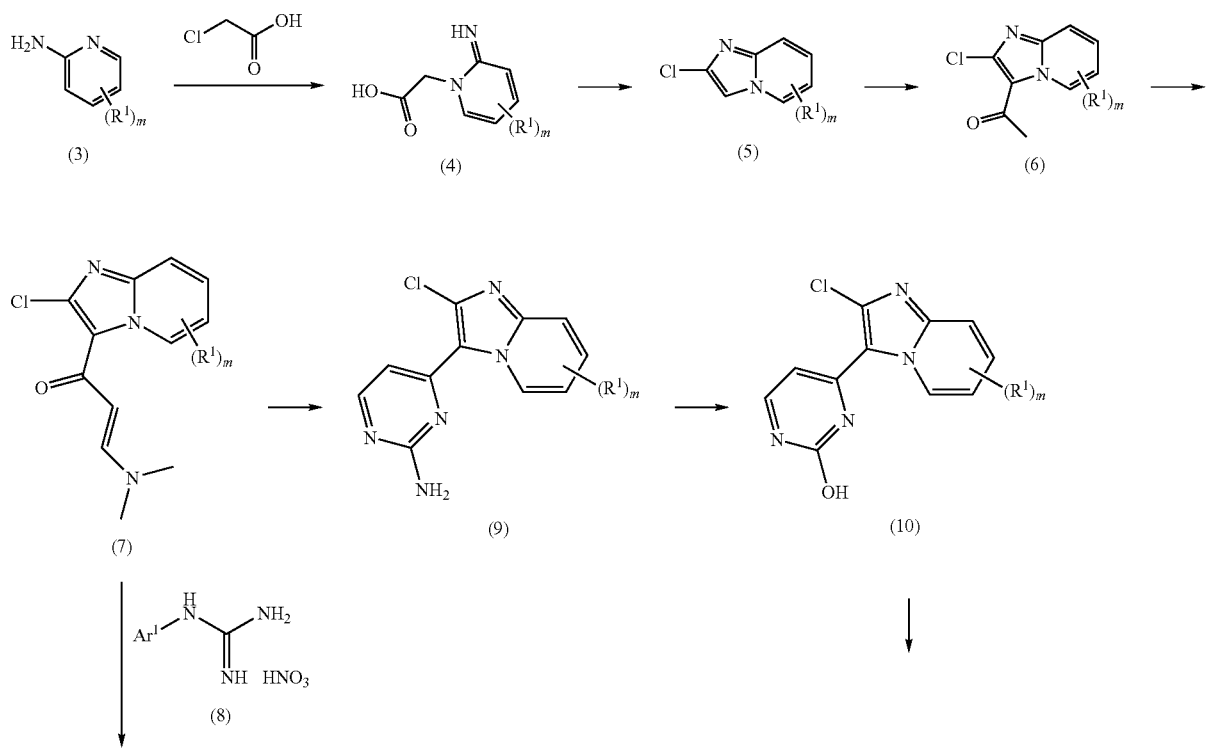

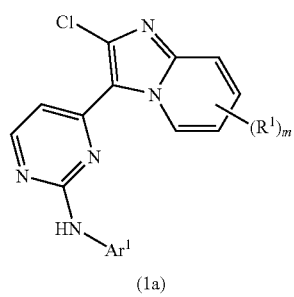

(1a)

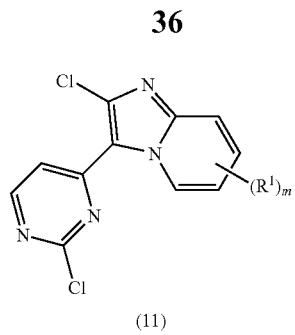

(11)

Compounds of formula (4) can be prepared by treating amines (3) with chloroacetic acid and a base, in a suitable solvent. Examples of suitable bases include but are not limited to, tertiary amines such as triethylamine and diisopropylethyl amine. Water is an example of a suitable solvent.

Treatment of (4) with phosphorusoxychloride at elevated temperature and in a suitable solvent (e.g. toluene) provides compounds of formula (5).

Compounds of formula (6) may be prepared by acylation of compounds of formula (5). Typically the acylation is conducted by treating (5) with an acylating agent, optionally in the presence of an acid or Lewis acid catalyst and optionally in a suitable solvent with optional heating. Typical acylating agents will be readily determined by those skilled in the art. An example of an acylating agent is acetic anhydride. Typical acid for use in this reaction is sulfuric acid.

Compounds of formula (7) may be prepared by reacting compounds of formula (6) with a dimethylformamide dialkyl acetal of formula $(CH_3)_2NCH(OR^{101})_2$ wherein $R^{101}$ is alkyl or cycloalkyl. Typical dimethylformamide dialkyl acetal for use in this method include but are not limited to dimethylformamide dimethylacetal and dimethylformamide di-tert-butyl acetal. The reaction is carried out by mixing compounds of formula (6) with the dimethylformamide dialkyl acetal, optionally with heating. Typical solvent includes but is not limited to N-methyl 2-pyrrolidinone.

Mixing compounds of formula (7) with amidines of formula (8) in a suitable solvent, optionally in the presence of a base (particularly when the amidine is in a salt form), and heating the reaction mixture to about 50° C.-150° C., afford compounds of formula (1). Typical solvents include lower alcohols such as methanol, ethanol, isopropanol, dimethylformamide and the like. The base is typically sodium alkoxide, potassium carbonate, or an amine base such as triethylamine.

Alternatively, the conversion of compounds of formula (7) to intermediates (1a) may be carried out by: (a) treating (7) with guanidine hydrochloride and a base as described in the preceding paragraph to obtain compounds of formula (9), (b) treating amines (9) with sodium nitrite in acetic acid and water to provide compounds of formula (10), (c) treating (10) with phosphorusoxy chloride at elevated temperature to provide chloro compounds of formula (11), and (d) treating compounds of formula (11) with an appropriate amines of formula $Ar^1NH_2$ in the presence of an acid such as but not limited to HCl, and a suitable solvent at elevated temperature. Examples of suitable solvent include but are not limited to lower alcohols such as 2-propanol.

Alternatively, (11) may be converted to (1a) in the presence of a suitable base at elevated temperature. Examples of suitable bases include but not limited to tertiary amines such as diethylisopropyl amine.

Conversion of (11) to (1a) may also be accomplished by metal catalysed cross coupling reaction conditions known to those skilled in the art, for example, by utilizing a palladium catalyst and a suitable ligand (e.g. palladium (II) acetate and Xantphos) to facilitate the reaction.

Scheme 3

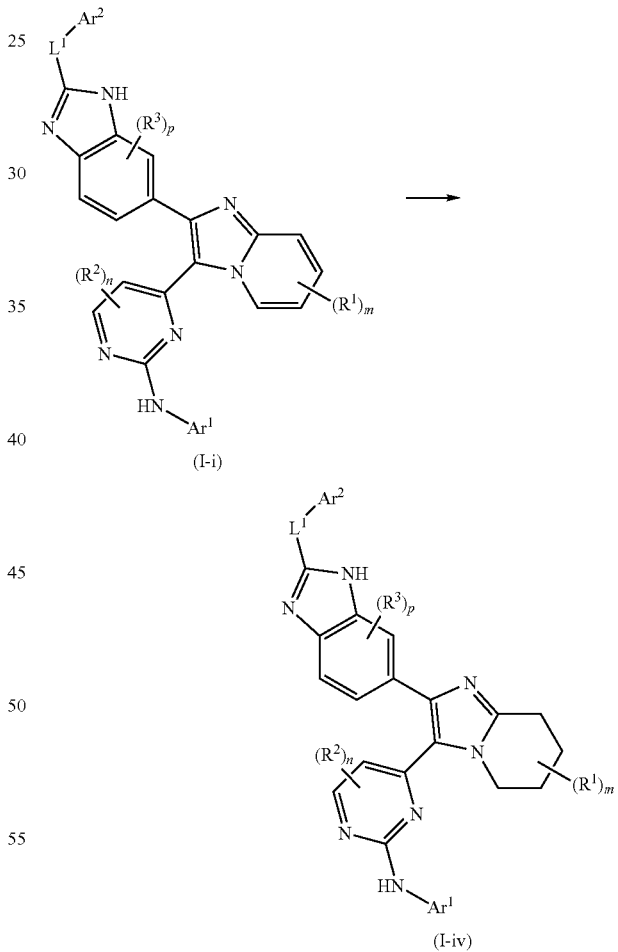

As shown in Scheme 3, compounds of formula (I-iv)) can be prepared from compounds of formula (I-i)) by catalytic hydrogenation using a catalyst such as 5% paladium on charcoal. The reaction is generally performed at elevated temperature and pressure in an alcoholic solvent such as but not limited to methanol.

Scheme 4

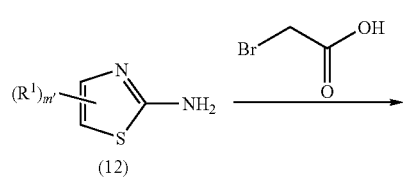

(12)

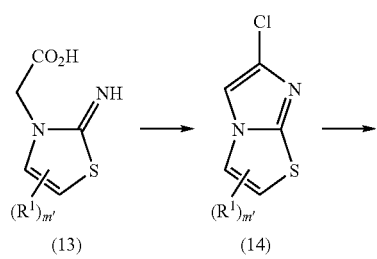

(13)   (14)

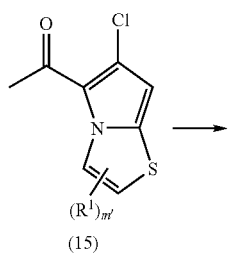

(15)

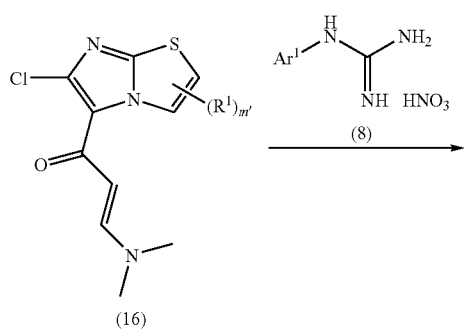

(16)   (8)

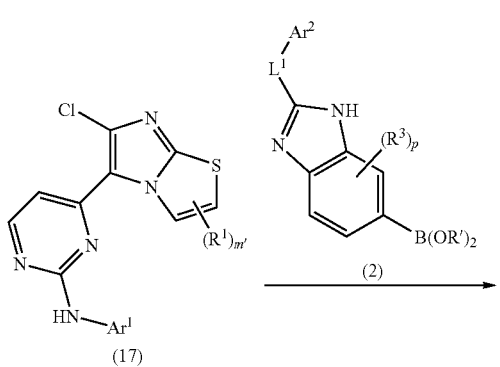

(17)   (2)

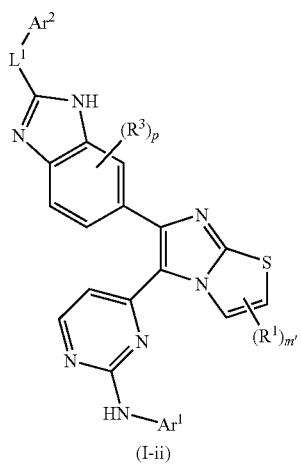

(I-ii)

As shown in Scheme 4, 2-aminothiazoles of formula (12) when reacted with bromoacetic acid provide compounds of formula (13). The reaction is typically performed by heating in a solvent such as but not limited to ethanol. Compounds of formula (14) can be prepared from compounds of formula (13) using phosphorusoxychloride in a solvent such as but not limited to toluene. Compounds of formula (15) can be prepared from compounds of formula (14) using sulfuric acid and acetic anhydride. The reaction is typically performed at elevated temperatures. Compounds of formula (16) can be prepared from compounds of formula (15) using N,N-dimethylformamide di-tert-butyl acetal and heat. The reaction is typically performed in a solvent such as but not limited to N-methyl-2-pyrrolidinone. Compounds of formula (17) can be prepared by reacting compounds of formula (16) with compounds of formula (8), using a base such as but not limited to potassium carbonate. Compounds of formula (I-ii) can be prepared from compounds of formula (17) by cross-coupling with boronic acids or esters of formula (2) using a palladium catalyst such as but not limited to palladium tetrakistriphenylphosphine as described in the literature and methods described herein.

Scheme 5

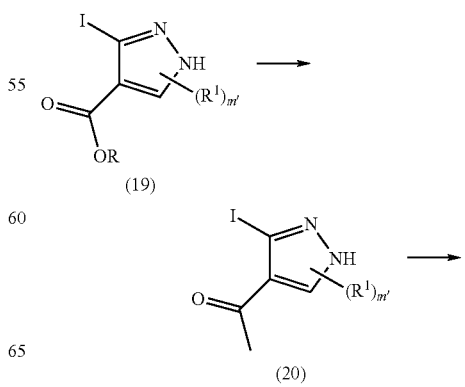

(19)

(20)

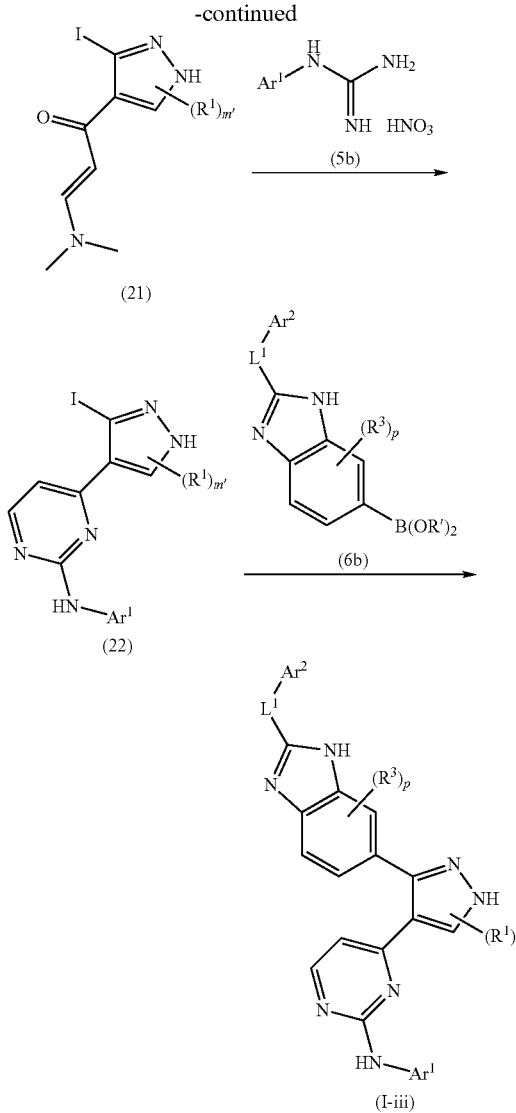

As shown in Scheme 5, 4-carboethoxypyrazoles of formula (19) when reacted with bis(cyclopentadienyl)-µ-Cl(dimethylaluminium)-µ-methylenetitanium (Tebbe's Reagent), followed by acidic hydrolysis provides compounds of formula (20). The reaction is typically performed in a solvent mixture such as but not limited to toluene/tetrahydrofuran, with hydrolysis of the intermediate enolether by an acid such as aqueous hydrochloric acid. Compounds of formula (21) can be prepared from compounds of formula (20) using sulfuric acid and acetic anhydride. The reaction is typically performed at elevated temperatures. Compounds of formula (22) can be prepared from compounds of formula (21) using N,N-dimethylformamide di-tert-butyl acetal and heat. The reaction is typically performed in a solvent such as but not limited to N-methyl-2-pyrrolidinone. Compounds of formula (22) can be prepared by reacting compounds of formula (21) with compounds of formula (8), using a base such as but not limited to potassium carbonate. Compounds of formula (I-iii) which are representative of the compounds of this invention can be prepared from compounds of formula (22) by cross-coupling with boronic acids or esters of formula (2) using a palladium catalyst such as but not limited to palladium tetrakistriphenylphosphine as described in the literature and methods described herein.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Organic Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

h. Examples

Example 1

1-[3-({4-[2-(2-benzyl-1H-benzimidazol-5-yl)imidazo[1,2-a]pyridin-3-yl]pyrimidin-2-yl}amino)phenyl]pyrrolidin-2-one

Example 1A 2-(2-iminopyridin-1(2H)-yl)acetic acid

In a 100 mL round bottom flask, 2-chloroacetic acid (10 g, 106 mmol) in water (16.3 mL) was treated with triethylamine (16.67 mL, 120 mmol) dropwise over about 6 minutes. After stirring the reaction at ambient temperature for 10 minutes, 2-aminopyridine (11.76 g, 125 mmol) was added and the mixture was heated at 90° C. for 5 hours. The reaction mixture was cooled to ambient temperature and diluted with ethanol (11 mL). The resulting suspension was stirred in an ice bath for 1 hour and filtered. The solid collected was washed with about 30 mL cold ethanol and dried under vacuum to a constant weight to provide the title compound. MS (DCI$^+$) m/e 152.9 (M+H)$^+$.

Example 1B 2-chloroimidazo[1,2-a]pyridine

To a 250 mL round bottom flask was charged EXAMPLE 1A (15.19 g, 100 mmol) and toluene (64 mL). The mixture was heated to 112° C. and POCl$_3$ (27.9 mL) was added dropwise over 15 minutes. The mixture became very thick with initial portions added. Upon complete addition, the suspension was stirred at 112° C. for 16 hours. The reaction was allowed to cool to ambient temperature and was added slowly to 320 mL of stirring cold (about 5° C.) water over 15 minutes. After stirring vigorously for 30 minutes, the layers were separated in a separatory funnel. The aqueous layer was cooled in an ice bath and neutralized to pH 7 with 10% aqueous NaOH (about 400 mL) with stirring. The resulting suspension was filtered, and the solid collected was dissolved in CH$_2$Cl$_2$ (300 mL) and dried over MgSO$_4$. The aqueous filtrate was extracted with CH$_2$Cl$_2$ (4×120 mL). The combined organic extracts were washed with brine and dried over MgSO$_4$. The two CH$_2$Cl$_2$ solutions drying over MgSO$_4$ were filtered, combined, and concentrated to provide the title compound. MS (DCI$^+$) m/e 153.0 (M+H)$^+$.

Example 1C 1-(2-chloroimidazo[1,2-a]pyridin-3-yl)ethanone

To a 500 mL round bottom flask was charged EXAMPLE 1B (12.2 g, 80 mmol), acetic anhydride (320 mL), and sulfuric acid (0.852 mL, 16 mmol). The mixture was heated at 140° C. for 2 hours. The reaction was cooled to ambient temperature, poured into 400 mL cold water, and extracted with 2×400 mL CH$_2$Cl$_2$. The combined organic extracts were washed with 350 mL 1N NaOH and brine, dried over Na$_2$SO$_4$, and concentrated under high vacuum to provide the title compound. MS (ESI$^+$) m/e 194.9 (M+H)$^+$.

Example 1D (E)-1-(2-chloroimidazo[1,2-a]pyridin-3-yl)-3-(dimethylamino)prop-2-en-1-one In a 100 mL round bottom flask, a solution of EXAMPLE 1C (4.25 g, 21.84 mmol), 1,1-di-tert-butoxy-N,N-dimethylmethanamine (28.8 mL, 120 mmol), and N-methyl-2-pyrrolidinone (15 mL) was heated at 85° C. for 2 hours. The reaction was concentrated under high vacuum on a rotavap at 60° C. The residual solid was triturated with 5 mL ether, filtered and dried to provide the title compound. MS (ES r) m/e 249.8 (M+H)$^+$.

Example 1E (E)-tert-butyl (tert-butoxycarbonylamino)(3-(2-oxopyrrolidin-1-yl)phenylamino)methylenecarbamate In a 500 mL round bottom flask was charged 1-(3-aminophenyl)pyrrolidin-2-one (5 g, 28.4 mmol), 2,2,10,10-tetramethyl-6-thioxo-3,9-dioxa-5,7-diazaundecane-4,8-dione (9.80 g, 35.5 mmol), polystyrene-carbodiimide (Argonaut P/N 800371, 1.42 mmole/g, 30.0 g, 42.6 mmol) and CH$_2$Cl$_2$ (300 mL). The resulting suspension was stirred at room temperature for 14 hours. The reaction was filtered and the collected solid was washed with 2×30 mL CH$_2$Cl$_2$. The filtrate was concentrated. The concentrate was purified by flash chromatography on a 140 g silica gel plug eluting with CH$_2$Cl$_2$ then 1:1 ethyl acetate/hexanes to provide the title compound. MS (ESI$^+$) m/e 419.1 (M+H)$^+$.

Example 1F 1-(3-(2-oxopyrrolidin-1-yl)phenyl)guanidine

In a 500 mL round-bottomed flask was charged EXAMPLE 1E (9.75 g, 23.30 mmol) and CH$_2$Cl$_2$ (35 mL). The resulting solution was treated with 4M hydrochloric acid in dioxane (69.9 mL, 280 mmol). The reaction was stirred at ambient temperature for 60 hours. The suspension was treated with ether (150 mL) and the mixture stirred for 2 hours. The ether supernatant was decanted from the solids. The solids were again triturated with ether (100 mL). The suspension was filtered and the solids were washed with ether and ethyl acetate. The solids were dried to constant weight in vacuo to provide a solid. In a 1 L Erlenmeyer flask, the solids were suspended in 15% isopropanol/CH$_2$Cl$_2$ (200 mL) and 3 N NaOH (75 mL). The mixture was stirred 30 minutes and the layers were separated. The organic phase was dried over Na$_2$SO$_4$ and concentrated to provide the title compound. MS ESI$^+$) m/e 218.9 (M+H)$^+$.

Example 1G 1-(3-(4-(2-chloroimidazo[1,2-a]pyridin-3-yl)pyrimidin-2-ylamino)phenyl)pyrrolidin-2-one In a 4 mL vial, a stirring solution of EXAMPLE 1D (0.062 g, 0.25 mmol) and N-methyl-2-pyrrolidinone (1.3 mL) was treated with potassium carbonate (0.138 g, 1 mmol) and EXAMPLE 1F (0.136 g, 0.625 mmol). The mixture was heated at 90° C. for 50 hours, cooled to ambient temperature and treated with 14 mL water. The suspension was stirred 30 minutes and filtered. The collected solid was washed with water (1 mL) and ether (0.5 mL) and was dried to constant weight under vacuum. The crude solid was purified by flash chromatography on an Alltech 5 g silica gel column with a gradient of from 0% to 2% methanol in $CH_2Cl_2$ to provide the title compound. MS $ESI^+$) m/e 405.0 $(M+H)^+$.

Example 1H

2-nitro-4-(4,4,5,5-tetramethyl-1,3,2-dioxaborolan-2-yl)aniline

In a 1 L round-bottomed flask was charged 4-bromo-2-nitroaniline (25.69 g, 118 mmol), 4,4,4',4',5,5,5',5'-octamethyl-2,2'-bi(1,3,2-dioxaborolane) (60.1 g, 237 mmol), potassium acetate (58.1 g, 592 mmol), and [1,1'-bis(diphenylphosphino)ferrocene]dichloropalladium(II) ($PdCl_2$ (dppf)) (0.199 g, 0.272 mmol) in N,N-dimethylformamide (237 ml). The mixture was heated at 100° C. for 18 hours. The mixture was cooled to ambient temperature, filtered through a pad of silica gel, and rinsed with ethyl acetate (500 mL). The filtrate was washed with brine (4×200 mL), dried over $MgSO_4$, and concentrated. The concentrate was treated with 300 mL hexanes and 150 mL methanol and was heated at 60° C. to get most of the slurry to dissolve. The reaction was allowed to cool to ambient temperature and was then allowed to stand in the freezer for 2 days. The suspension was filtered, rinsed with cold hexanes, and dried to constant weight to provide the title compound. MS $DCI^+$) m/e 265.1 $(M+H)^+$.

Example 1I

4-(4,4,5,5-tetramethyl-1,3,2-dioxaborolan-2-yl)benzene-1,2-diamine

In a 250 mL stainless steel pressure bottle a solution of EXAMPLE 1H (5 g, 18.93 mmol) in ethyl acetate (50 mL) was treated with 10% Pd on carbon (1.25 g, 1.175 mmol). The suspension was stirred under a hydrogen atmosphere for 36 hours at 30 psi at ambient temperature. The mixture was filtered through a nylon membrane and concentrated to provide the title compound. MS APCI(+)) m/e 235.19 $(M+H)^+$.

Example 1J

2-benzyl-6-(4,4,5,5-tetramethyl-1,3,2-dioxaborolan-2-yl)-1H-benzo[d]imidazole In a 100 mL round bottom flask, a solution of phenylacetic acid (1.894 g, 13.91 mmol) in tetrahydrofuran (21 mL) was treated with 1,1'-carbonyldiimidazole (2.26 g, 13.91 mmol) at ambient temperature. The solution was heated at 50° C. for 30 minutes. EXAMPLE 1I (2.96 g, 12.64 mmol) was added and the reaction was stirred at 50° C. for 1 hour. Acetic acid (10.5 mL) was added and the mixture was stirred at 90° C. for 15 hours. The mixture was evaporated to dryness. The residue was taken up in ethyl acetate/water (150 mL/100 mL) and the aqueous phase was saturated with solid $Na_2CO_3$ with stirring. The phases were separated and the aqueous layer was extracted with 75 mL ethyl acetate. The combined organic layers were washed with brine, dried over $Na_2SO_4$, filtered, and concentrated. The concentrate was purified by flash chromatography on an AnaLogix SF40-150 g silica gel column using an AnaLogix IntelliFlash 280 system eluting with a gradient of from 15% to 50% ethyl acetate in hexanes to provide the title compound. MS $DCI^+$) m/e 335.2 $(M+H)^+$.

Example 1K

1-[3-({4-[2-(2-benzyl-1H-benzimidazol-5-yl)imidazo[1,2-a]pyridin-3-yl]pyrimidin-2-yl}amino)phenyl]pyrrolidin-2-one A 2 mL Biotage microwave vial was charged with EXAMPLE 1G (0.039 g, 0.096 mmol), EXAMPLE 1J (0.035 g, 0.106 mmol), $PdCl_2$ $(PPh_3)_2$ (0.0038 g, 0.005 mmol), sodium carbonate (0.026 g, 0.241 mmol), 1,2-dimethoxyethane (0.6 mL) and water (0.25 mL). The mixture was heated at 160° C. in a Biotage microwave reactor for 40 minutes. The reaction was partitioned between 10% methanol/ethyl acetate and water. The organic layer was dried over $MgSO_4$, filtered, and concentrated. The concentrate was dissolved in 1.5 mL dimethyl sulfoxide, filtered through a membrane filter and purified by reverse-phase HPLC on a Phenomenex C18 column (3×15 cm, 10 μm particle size) using a gradient of acetonitrile in 0.15% aqueous trifluoroacetic acid to provide the title compound as a trifluoroacetic acid salt. MS ($ESI^+$) m/e 577.2 $(M+H)^+$; $^1$H NMR (300 MHz, methanol-$d_4$) δ ppm 2.15 (m, 2 H) 2.56 (m, 2 H) 3.89 (m, 2 H) 4.54 (s, 2 H) 6.61 (d, 1 H) 7.19-7.32 (m, 3 H) 7.36-7.47 (m, 6 H) 7.74-7.86 (m, 4 H) 7.98 (m, 1 H) 8.13 (m, 1 H) 8.28 (d, 1 H) 9.65 (d, 1 H).

Example 2

4-[2-(2-benzyl-1H-benzimidazol-6-yl)imidazo[1,2-a]pyridin-3-yl]-N-{3-[2-(dimethylamino)ethyl]phenyl}pyrimidin-2-amine

Example 2A

4-(2-chloroimidazo[1,2-a]pyridin-3-yl)pyrimidin-2-amine

In a 500 mL round bottom flask was charged EXAMPLE 1D (11.3 g, 45.3 mmol), guanidine carbonate (12.2 g, 67.9 mmol) and N-methyl-2-pyrrolidinone (140 mL) and the reaction mixture was heated at 92° C. for 72 hours. The reaction was allowed to cool to ambient temperature and was poured into 750 mL water. The resulting suspension was stirred 45 minutes and filtered. The collected solids were washed with water and air dried on the filter under vacuum overnight to provide the title compound. MS ($DCI^+$) m/e 246.0 $(M+H)^+$.

Example 2B

4-(2-chloroimidazo[1,2-a]pyridin-3-yl)pyrimidin-2-ol

To a 500 mL round bottom flask was charged EXAMPLE 2A (9.95 g, 40.5 mmol) and acetic acid (167 mL). The suspension was heated at 85° C. until a homogeneous solution formed. The reaction was allowed to cool to 65° C. and a solution of sodium nitrite (8.38 g, 122 mmol) in water (26 mL) was added dropwise over 10 minutes. Upon complete addition, the solution was stirred at 65° C. for 35 minutes. The reaction mixture was cooled to ambient temperature and then further cooled in an ice bath at 0° C. The reaction was quenched to pH 6-7 with 3 N NaOH (about 910 mL). The resulting cold suspension was filtered and the solid collected was washed with 3×400 mL water and 2×130 mL ether. The solid was dried in a vacuum oven at 70° C. to provide the title compound. MS ($ESI^+$) m/e 246.8 $(M+H)^+$.

Example 2C 2-chloro-3-(2-chloropyrimidin-4-yl)imidazo[1,2-a]pyridine

To a 500 mL round bottom flask was charged EXAMPLE 2B (9.1 g, 36.9 mmol) and POCl$_3$ (86 mL, 922 mmol). The suspension was heated to 80° C. for 5 hours. The reaction was cooled to ambient temperature and the suspension was added slowly to 500 mL of vigorously stirring water in an ice bath via an addition funnel at such a rate that the internal temperature did not exceed 20° C. Upon complete addition, the suspension was stirred for 30 minutes and then was basified to pH 10 with 15% aqueous NaOH (about 1280 mL) added in a rapid dropwise manner at such a rate to keep the internal temperature below 20° C. Upon basification, suspension was stirred 30 minutes and filtered. The collected solid was washed with 4×400 mL water, and dried in a vacuum oven at 65° C. to provide the title compound. MS (ESI$^+$) m/e 264.8 (M+H)$^+$.

Example 2D

N,N-dimethyl-2-(3-nitrophenyl)ethanamine

In a 250 mL round bottom flask was charged 1-(2-bromoethyl)-3-nitrobenzene (10 g, 43.5 mmol) and acetonitrile (36 mL). The suspension was treated with triethylamine (18.1 mL, 130 mmol) and dimethylamine (2 M in tetrahydrofuran, 65.2 mL, 130 mmol). The resulting solution was stirred at ambient temperature for 48 hours. The reaction was concentrated. The residual solid was partitioned between ethyl acetate (130 mL) and 60 ml saturated aqueous sodium bicarbonate. The aqueous layer was washed with ethyl acetate (75 mL). The combined organic layers were washed with brine, dried over MgSO$_4$, filtered, and concentrated. The concentrate was purified by flash chromatography on an 80 g silica gel column using an AnaLogix IntelliFlash 280 system eluting with a gradient of from 0% to 7% methanol in CH$_2$Cl$_2$ to provide the title compound. MS (DCI$^+$) m/e 195.1 (M+H)$^+$.

Example 2E 3-(2-(dimethylamino)ethyl)aniline

In a 250 mL stainless steel pressure bottle, EXAMPLE 2D (5.02 g, 25.8 mmol) in methanol (70 mL) was treated with 5% Pd—C (wet, 1.40 g, 25.8 mmol) and the suspension was shaken under 30 psi of hydrogen for 1.3 hours at ambient temperature. The mixture was filtered through a nylon membrane and the filtrate was concentrated to provide the title compound. MS (DCI$^+$) m/e 165.1 (M+H)$^+$.

Example 2F 4-(2-chloroimidazo[1,2-a]pyridin-3-yl)-N-(3-(2-(dimethylamino)ethyl)phenyl)pyrimidin-2-amine A 20 mL reaction vial, equipped with a stir bar, was charged with EXAMPLE 2C (0.67 g, 2.53 mmol), EXAMPLE 2E (0.46 g, 2.80 mmol)), 4 M HCl in 1,4-dioxane (0.69 mL, 2.77 mmol) and 2-propanol (13 ml). The vessel was sealed and the mixture was heated on a thermal block at 120° C. for 3.5 hours. The reaction was cooled to ambient temperature and concentrated. The concentrate was dissolved in 60 mL 15% methanol/CH$_2$Cl$_2$ and washed with 15 mL saturated aqueous sodium carbonate and 15 mL brine. The organic layer was dried over Na$_2$SO$_4$, filtered, and concentrated. The concentrate was purified by flash chromatography on a 20 g silica gel column eluting with methanol in CH$_2$Cl$_2$ to provide the title compound. MS (ESI$^+$) m/e 393.0 (M+H)$^+$.

Example 2G

4-[2-(2-benzyl-1H-benzimidazol-6-yl)imidazo[1,2-a]pyridin-3-yl]-N-{3-[2-(dimethylamino)ethyl]phenyl}pyrimidin-2-amine The trifluoroacetic acid salt of the title compound was prepared as described in EXAMPLE 1K, substituting EXAMPLE 2F for EXAMPLE 1G. MS (ESI$^+$) m/e 565.3 (M+H)$^+$; $^1$H NMR (300 MHz, methanol-d$_4$) δ ppm 2.93 (s, 6 H) 3.04 (m, 2 H) 3.40 (m, 2 H) 4.53 (s, 2 H) 6.58 (d, 1 H) 7.01 (d, 1 H) 7.22 (m, 1 H) 7.32 (m, 1 H) 7.37-7.46 (m, 5 H) 7.59 (m, 1 H) 7.69-7.83 (m, 5 H) 7.98 (m, 1 H) 8.24 (d, 1 H) 9.71 (d, 1 H).

Example 3

N-{3-[2-(dimethylamino)ethyl]phenyl}-4-{2-[2-(2-methoxybenzyl)-1H-benzimidazol-5-yl]imidazo[1,2-a]pyridin-3-yl}pyrimidin-2-amine

Example 3A ethyl 2-(2-methoxyphenyl)acetimidate

Into a 500 mL round-bottomed flask was added 2-(2-methoxyphenyl)acetonitrile (50.45 g, 343 mmol) in ethanol (101 mL). HCl (10.42 mL, 343 mmol) gas was bubbled through the suspension for 15 minutes. The HCl bubbler was removed and the reaction was stirred at ambient temperature for 48 hours. The reaction was diluted with 200 mL ether, and the suspension was filtered. The collected solid was washed with ether and dried under vacuum to provide the title compound as the hydrochloride salt. MS (DCI$^+$) m/e 194.0 (M+H)$^+$.

Example 3B 2-(2-methoxybenzyl)-6-(4,4,5,5-tetramethyl-1,3,2-dioxaborolan-2-yl)-1H-benzo[d]imidazole In a 1 L round-bottomed flask, a solution of EXAMPLE 1I (9.53 g, 40.7 mmol), in methanol (204 mL) was treated with EXAMPLE 3A (10.29 g, 44.8 mmol). The reaction was stirred at ambient temperature for 17 hours. The reaction was concentrated. The concentrate was purified by flash chromatography on a 90 g silica gel column eluting with 1:1 ethyl acetate/hexanes to provide a solid. The solid was triturated with ethyl ether, filtered, and dried under vacuum to provide the title compound. MS (DCI$^+$) m/e 365.0 (M+H)$^+$.

Example 3C

N-{3-[2-(dimethylamino)ethyl]phenyl}-4-{2-[2-(2-methoxybenzyl)-1H-benzimidazol-5-yl]imidazo[1,2-a]pyridin-3-yl}pyrimidin-2-amine The trifluoroacetic acid salt of the title compound was prepared as described in EXAMPLE 1K, substituting EXAMPLE 2F for EXAMPLE 1G and EXAMPLE 3B for EXAMPLE 1J. MS (ESI$^+$) m/e 595.3 (M+H)$^+$; $^1$H NMR (300 MHz, methanol-d$_4$) δ ppm 2.93 (s, 6 H) 3.04 (m, 2 H) 3.40 (m, 2 H) 3.81 (s, 3 H) 4.50 (s, 2 H) 6.57 (d, 1 H) 6.98-7.11 (m, 3

H) 7.17 (m, 1 H) 7.31 (t, 1 H) 7.42 (m, 2 H) 7.58-7.70 (m, 3 H) 7.78 (m, 3 H) 7.98 (m, 1 H) 8.24 (d, 1 H) 9.68 (d, 1 H).

Example 4

4-[2-(2-benzyl-1H-benzimidazol-5-yl)imidazo[1,2-a]pyridin-3-yl]-N-phenylpyrimidin-2-amine Example 4A 4-(2-chloroimidazo[1,2-a]pyridin-3-yl)-N-phenylpyrimidin-2-amine The title compound was prepared as described in EXAMPLE 1G, substituting phenylguanidine carbonate for EXAMPLE 1F. MS (ESI$^+$) m/e 321.9 (M+H)$^+$ Example 4B 4-[2-(2-benzyl-1H-benzimidazol-5-yl)imidazo[1,2-a]pyridin-3-yl]-N-phenylpyrimidin-2-amine The trifluoroacetic acid salt of the title compound was prepared as described in EXAMPLE 1K, substituting EXAMPLE 4A for EXAMPLE 1G. MS (ESI$^+$) m/e 494.1 (M+H)$^+$; $^1$H NMR (300 MHz, DMSO-d$_6$) δ ppm 4.47 (s, 2 H) 6.60 (d, 1 H) 6.96 (m, 1 H) 7.15 (m, 1 H) 7.26 (m, 2 H) 7.32-7.46 (m, 6 H) 7.57 (m, 1 H) 7.71 (m, 3 H) 7.80 (m, 2 H) 7.94 (m, 1 H) 8.34 (d, 1 H) 9.52 (d, 1 H) 9.79 (s, 1 H).

Example 5

4-{2-[2-(2-chlorobenzyl)-1H-benzimidazol-5-yl]imidazo[1,2-a]pyridin-3-yl}-N-{3-[2-(dimethylamino)ethyl]phenyl}pyrimidin-2-amine The title compound was prepared as described in EXAMPLE 1K, substituting EXAMPLE 2F for EXAMPLE 1G and EXAMPLE 9A for EXAMPLE 1J. MS (ESI$^+$) m/e 599.3 (M+H)$^+$, $^1$H NMR (400 MHz, DMSO-d$_6$) δ ppm 12.40 (d, 1 H) 9.61 (m, 2 H) 8.28 (s, 1 H) 7.73 (m, 2 H) 7.63 (s, 1 H) 7.58 (d, 2 H) 7.40-7.51 (m, 4 H) 7.33 (m, 2 H) 7.19 (t, 1 H) 7.05 (t, 1 H) 6.85 (d, 1 H) 6.57 (m, 1 H) 4.35 (s, 2 H) 2.67 (m, 2 H) 2.48 (m, 2 H) 2.17 (s, 6 H).

Example 6

N-{3-[2-(dimethylamino)ethyl]phenyl}-4-(2-{2-[2-(trifluoromethyl)benzyl]-1H-benzimidazol-5-yl}imidazo[1,2-a]pyridin-3-yl)pyrimidin-2-amine The title compound was prepared as described in EXAMPLE 1K substituting EXAMPLE 2F for EXAMPLE 1G and EXAMPLE 42B for EXAMPLE 1J. MS (ESI$^+$) m/e 633.3 (M+H)$^+$, $^1$H NMR (500 MHz, DMSO-d$_6$) δ ppm 12.39 (bs, 1 H) 9.67 (d, 1 H) 9.59 (d, 1 H) 8.28 (dd, 1 H) 7.76 (m, 2 H) 7.66 (m, 2 H) 7.58 (m, 2 H) 7.50 (m, 4 H) 7.42 (t, 1 H) 7.18 (t, 1 H) 7.06 (t, 1 H) 6.84 (d, 1 H) 6.56 (dd, 1 H) 4.42 (s, 2 H) 2.66 (m, 2 H) 2.44 (m, 2 H) 2.15 (s, 6 H).

Example 7

4-[6-(2-benzyl-1H-benzimidazol-6-yl)imidazo[2,1-b][1,3]thiazol-5-yl]-N-{3-[2-(dimethylamino)ethyl]phenyl}pyrimidin-2-amine Example 7A 1-(6-chloroimidazo[2,1-b]thiazol-5-yl)ethanone The title compound was prepared according to the procedure of EXAMPLE 1C, substituting 6-chloro-imidazo[2,1-b]thiazole for EXAMPLE 1B. MS: (ESI$^+$) m/e 200.8 (M+H)$^+$.

Example 7B (E)-1-(6-chloroimidazo[2,1-b]thiazol-5-yl)-3-(dimethylamino)prop-2-en-1-one The title compound was prepared according to the procedure of EXAMPLE 2D, substituted EXAMPLE 7A for EXAMPLE 1C. MS: (ESI$^+$) m/e 255.8 (M+H)$^+$.

Example 7C (E)-tert-butyl (tert-butoxycarbonylamino)(3-(2-(dimethylamino)ethyl)phenylamino)methylenecarbamate The title compound was prepared according to the procedure of EXAMPLE 1E, substituting 3-(2-(dimethylamino)ethyl)aniline for (3-aminophenyl)pyrrolidin-2-one. MS: (ESI$^+$) m/e 407.8 (M+H)$^+$.

Example 7D 1-(3-(2-(dimethylamino)ethyl)phenyl)guanidine

The title compound was prepared according to the procedure of EXAMPLE 1F, substituting EXAMPLE 7C for EXAMPLE 1E. MS: (ESI$^+$) m/e 207.3 (M+H)$^+$.

Example 7E 4-(6-chloroimidazo[2,1-b]thiazol-5-yl)-N-(3-(2-(dimethylamino)ethyl)phenyl)pyrimidin-2-amine The title compound was prepared according to the procedure of EXAMPLE 1G, substituting EXAMPLE 7B for EXAMPLE 1D and EXAMPLE 7D for EXAMPLE 1F. MS: (ESI$^+$) m/e 399.0 (M+H)$^+$.

Example 7F

4-[6-(2-benzyl-1H-benzimidazol-6-yl)imidazo[2,1-b][1,3]thiazol-5-yl]-N-{3-[2-(dimethylamino)ethyl]phenyl}pyrimidin-2-amine The title compound was prepared according to the procedure of EXAMPLE 1K, substituting EXAMPLE 7E for EXAMPLE 1G. MS: (ESI$^+$) m/e 571.3 (M+H)$^+$; $^1$H NMR (500 MHz, DMSO-d$_6$) δ ppm 12.44, 12.39 (d, 1 H), 9.55 (s, 1H), 8.86 (s, 1H), 8.18 (s, 1H), 7.68-7.55 (m, 3H), 7.47 (d, 1H), 7.40-7.18 (m, 8H), 6.85 (d, 1H), 6.51 (s, 1H), 4.21 (s, 2H), 2.70 (t, 2H), 2.50 (t, 2H), 2.19 (s, 6H).

Example 8

N-{3-[2-(dimethylamino)ethyl]phenyl}-4-{6-[2-(2-methoxybenzyl)-1H-benzimidazol-6-yl]imidazo[2,1-b][1,3]thiazol-5-yl}pyrimidin-2-amine The title compound was prepared according to the procedure of EXAMPLE 1K, substituting EXAMPLE 7E for EXAMPLE 1G and EXAMPLE 3B for EXAMPLE 1J. MS: (ESI$^+$) m/e 601.3 (M+H)$^+$; $^1$H NMR (500 MHz, DMSO-d$_6$) δ ppm 12.23, 12.17 (d, 1 H), 9.55 (s, 1H), 8.86 (s, 1H), 8.19 (t, 1H), 7.63-7.55 (m, 3H), 7.46 (d, 1H), 7.36 (d, 1H), 7.29-7.18 (m, 3H), 7.02 (d, 1H), 6.93 (t, 1H), 6.85 (d, 1H), 6.52 (dd, 1H), 4.17 (s, 2 H), 3.79 (s, 3H), 2.69 (t, 2H), 2.49 (t, 2H), 2.19 (s, 6H).

Example 9

4-{6-[2-(2-chlorobenzyl)-1H-benzimidazol-6-yl]imidazo[2,1-b][1,3]thiazol-5-yl}-N-{3-[2-(dimethylamino)ethyl]phenyl}pyrimidin-2-amine Example 9A 2-(2-chlorobenzyl)-6-(4,4,5,5-tetramethyl-1,3,2-dioxaborolan-2-yl)-1H-benzo[d]imidazole The title compound was prepared according to the procedure of EXAMPLE 1J, substituting 2-chlorophenyl acetic acid for phenyl acetic acid. MS: (ESI$^+$) m/e 369.0 (M+H)$^+$ Example 9B 4-{6-[2-(2-chlorobenzyl)-1H-benzimidazol-6-yl]imidazo[2,1-b][1,3]thiazol-5-yl}-N-{3-[2-(dimethylamino)ethyl]phenyl}pyrimidin-2-amine The title compound was prepared according to the procedure of EXAMPLE 1K, substituting EXAMPLE 7E for EXAMPLE 1G and EXAMPLE 9A for EXAMPLE 1J. MS: (ESI$^+$) m/e 605.3 (M+H)$^+$; $^1$H NMR (500 MHz, DMSO-d$_6$) δ ppm 12.44, 12.39 (d, 1 H), 9.55 (d, 1H), 8.86 (s, 1H), 8.19 (dd, 1H), 7.63-7.40 (m, 6H), 7.38-7.30 (m, 4H), 7.20 (t, 1H), 6.85 (d, 1H), 6.52 (dd, 1H), 4.35 (s, 2H), 2.69 (t, 2H), 2.49 (t, 2H), 2.19 (s, 6H).

Example 10

N-{3-[2-(dimethylamino)ethyl]phenyl}-4-{2-[2-(2-phenylethyl)-1H-benzimidazol-6-yl]imidazo[1,2-a]pyridin-3-yl}pyrimidin-2-amine Example 10A 4-(2-(4-amino-3-nitrophenyl)imidazo[1,2-a]pyridin-3-yl)-N-(3-(2-(dimethylamino)ethyl)phenyl)pyrimidin-2-amine The title compound was prepared as described in EXAMPLE 1K substituting EXAMPLE 2F for EXAMPLE 1G and EXAMPLE 1H for EXAMPLE 1J. MS (ESI$^+$) m/e 495.1 (M+H)$^+$.

Example 10B

N-{3-[2-(dimethylamino)ethyl]phenyl}-4-{2-[2-(2-phenylethyl)-1H-benzimidazol-6-yl]imidazo[1,2-a]pyridin-3-yl}pyrimidin-2-amine A 5 mL microwave tube was charged with EXAMPLE 10A (50 mg, 0.101 mmol) and ethanol (1 mL). The suspension was treated with 3-phenylpropanal (14.24 mg, 0.106 mmol) and sodium hydrosulfite (52.8 mg, 0.303 mmol). The mixture was heated in a Biotage Initiator microwave oven at 150° C. for 30 minutes. The reaction quenched with 5M aqueous ammonium hydroxide and diluted with dichloromethane. The organic layer was separated, dried with sodium sulfate filtered, and concentrated. The residue was purified on a Shimadzu SIL-10 HPLC system using a Phenominex Gemini 10 micron C18 column (150×30 mm, 110 Angstrom pore size) and eluting with a gradient of 40% to 80% acetonitrile/water with 0.1% ammonium hydroxide to provide the title compound. MS (ESI$^+$) m/e 579.3 (M+H)$^+$, $^1$H NMR (400 MHz, DMSO-d$_6$) δ ppm 12.35 (d, 1 H) 9.63 (m, 2 H) 8.28 (m, 1 H) 7.75 (d, 1 H) 7.62 (m, 3 H) 7.48 (m, 2 H) 7.41 (d, 1 H) 7.29 (m, 4 H) 7.19 (m, 2 H) 7.05 (m, 1 H) 6.85 (d, 1 H) 6.56 (dd, 1 H) 3.14 (s, 4 H) 2.66 (m, 2 H) 2.45 (m, 2 H) 2.15 (m, 6 H).

Example 11

N-phenyl-4-[2-(2-phenyl-1H-benzimidazol-6-yl)imidazo[1,2-a]pyridin-3-yl]pyrimidin-2-amine The title compound was prepared as described in EXAMPLE 1K substituting EXAMPLE 4A for EXAMPLE 1G and EXAMPLE 27A for EXAMPLE 1J. MS (ESI$^+$) m/e 480.1 (M+H)$^+$, $^1$H NMR (400 MHz, DMSO-d$_6$) δ ppm 13.01 (d, 1 H) 9.72 (d, 1 H) 9.59 (dd, 1 H) 8.31 (dd, 1 H) 8.19 (m, 2 H) 7.76 (m, 4 H) 7.61 (m, 1 H) 7.56 (d, 2 H) 7.52 (m, 3 H) 7.30 (m, 2 H) 7.08 (m, 1 H) 6.98 (t, 1 H) 6.62 (dd, 1 H).

Example 12

6-{3-[2-({3-[2-(dimethylamino)ethyl]phenyl}amino)pyrimidin-4-yl]imidazo[1,2-a]pyridin-2-yl}-N-phenyl-1H-benzimidazol-2-amine Example 12A 4-(3-(2-(3-(2-(dimethylamino)ethyl)phenylamino)pyrimidin-4-yl)imidazo[1,2-a]pyridin-2-yl)benzene-1,2-diamine A 50 mL pressure bottle was charged with 4-(2-(4-amino-3-nitrophenyl)imidazo[1,2-a]pyridin-3-yl)-N-(3-(2-(dimethylamino)ethyl)phenyl)pyrimidin-2-amine (60 mg, 0.121 mmol) from EXAMPLE 10A and tetrahydrofuran (20 mL). The solution was treated with 50% palladium on carbon (30.0 mg, 0.282 mmol) and stirred for 24 hours at 30 psi at ambient temperature. The mixture was filtered through a nylon membrane and solvents were concentrated to provide the title compound. MS (ESI$^+$) m/e 465.1 (M+H)$^+$.

Example 12B

6-{3-[2-({3-[2-(dimethylamino)ethyl]phenyl}amino)pyrimidin-4-yl]imidazo[1,2-a]pyridin-2-yl}-N-phenyl-1H-benzimidazol-2-amine A 50 ml round-bottom flask was charged with EXAMPLE 12A (56 mg, 0.121 mmol) and anhydrous tetrahydrofuran (1.0 ml). The reaction mixture was treated with phenyl isothiocyanate (0.015 ml, 0.127 mmol) and N-(3-dimethylaminopropyl)-N'-ethylcarbodiimide hydrochloride (41.6 mg, 0.217 mmol). The mixture was heated to 50° C. Anhydrous 1-methyl-2-pyrrolidinone (1.0 ml) was added to form a solution. The mixture was heated for 48 hours at 50° C. The mixture was cooled and diluted with dichloromethane and water. The layers were separated, and organic layer washed with brine, dried with sodium sulfate, filtered, and concentrated. The residue purified on a Shimadzu SIL-10 HPLC system using a Phenominex Gemini 10 micron C18 column (150×30 mm, 110 Angstrom pore size) and eluting with a gradient of 40% to 80% acetonitrile/water with 0.1% ammonium hydroxide to produce the title compound. MS (ESI$^+$) m/e 566.3 (M+H)$^+$, $^1$H NMR (400 MHz, DMSO-d$_6$) δ ppm 11.00 (d, 1 H) 9.63 (bs, 2 H) 9.49 (s, 1 H) 8.29 (m, 1 H) 7.75 (m, 3 H) 7.64 (s, 1 H) 7.60 (d, 1 H) 7.55 (s, 1 H) 7.48 (m, 1 H) 7.34 (m, 4 H) 7.20 (m, 1 H) 7.05 (m, 1 H) 6.94 (t, 1 H) 6.85 (d, 1 H) 6.61 (bs, 1 H) 2.68 (m, 2 H) 2.49 (m, 2 H) 2.18 (s, 6 H).

Example 13

N-{3-[2-(dimethylamino)ethyl]phenyl}-4-[2-(2-phenyl-1H-benzimidazol-6-yl)imidazo[1,2-a]pyridin-3-yl]pyrimidin-2-amine The title compound was prepared as described in EXAMPLE 1K substituting EXAMPLE 2F for EXAMPLE 1G and EXAMPLE 27A for EXAMPLE 1J. MS (ESI$^+$) m/e 551.3 (M+H)$^+$, $^1$H NMR (400 MHz, DMSO-d$_6$) δ ppm 13.06 (d, 1 H) 9.61 (m, 2 H) 8.31 (m, 1 H) 8.19 (m, 2 H) 7.69-7.83 (m, 2 H) 7.64 (s, 1 H) 7.57 (m, 4 H) 7.51 (m, 3 H) 7.20 (t, 1 H) 7.07 (t, 1 H) 6.85 (d, 1 H) 6.62 (m, 1 H) 2.68 (m, 2 H) 2.48 (m, 2 H) 2.19 (s, 6 H).

Example 14

4-[2-(2-benzyl-1H-benzimidazol-6-yl)imidazo[1,2-a]pyridin-3-yl]-N-(2-methoxy-4-morpholin-4-ylphenyl)pyrimidin-2-amine Example 14A 4-(2-chloroimidazo[1,2-a]pyridin-3-yl)-N-(2-methoxy-4-morpholin-4-ylphenyl)pyrimidin-2-amine The title compound was prepared as described in EXAMPLE 2F, substituting 2-methoxy-4-morpholinoaniline for EXAMPLE 2E. MS (ESI$^+$) m/e 437.0 (M+H)$^+$.

Example 14B

4-[2-(2-benzyl-1H-benzimidazol-6-yl)imidazo[1,2-a]pyridin-3-yl]-N-(2-methoxy-4-morpholin-4-ylphenyl)pyrimidin-2-amine The trifluoroacetic acid salt of the title compound was prepared as described in EXAMPLE 1K, substituting EXAMPLE 14A for EXAMPLE 1G. MS (ESI$^+$) m/e 609.4 (M+H)$^+$; $^1$H NMR (300 MHz, DMSO-d$_6$) δ ppm 9.42 (bds, 1H), 8.62 (bds, 1H), 8.16 (d, 1H), 7.92 (s, 1H), 7.79 (m, 2H), 7.68 (dd, 1H), 7.57 (t, 1H), 7.41 (m, 7H), 7.08 (m, 1H), 6.72 (d, 1H), 6.50 (dd, 1H), 6.41 (d, 1H), 4.47 (s, 2H), 3.82 (s, 3H), 3.77 (m, 4H), 3.14 (m, 4H).

Example 15

4-[2-(2-benzyl-1H-benzimidazol-6-yl)imidazo[1,2-a]pyridin-3-yl]-N-(2-methoxyphenyl)pyrimidin-2-amine Example 15A 4-(2-chloroimidazo[1,2-a]pyridin-3-yl)-N-(2-methoxyphenyl)pyrimidin-2-amine The title compound was prepared as described in EXAMPLE 2F, substituting 2-methoxyaniline for EXAMPLE 2E. MS ESI$^+$) m/e 351.0 (M+H)$^+$.

Example 15B

4-[2-(2-benzyl-1H-benzimidazol-6-yl)imidazo[1,2-a]pyridin-3-yl]-N-(2-methoxyphenyl)pyrimidin-2-amine The trifluoroacetic acid salt of the title compound was prepared as described in EXAMPLE 1K, substituting EXAMPLE 15A for EXAMPLE 1G. MS (ESI$^+$) m/e 524.2 (M+H)$^+$; $^1$H NMR (300 MHz, DMSO-d$_6$) δ ppm 8.64 (s, 1H), 8.27 (d, 1H), 7.93 (s, 1H), 7.80 (m, 3H), 7.69 (d, 1H), 7.56 (m, 1H), 7.43-7.35 (m, 5H), 7.12-7.08 (m, 3H), 6.90 (m, 1H), 6.53 (d, 1H), 4.48 (s, 2H), 3.86 (s, 3H).

Example 16

4-[2-(2-benzyl-1H-benzimidazol-6-yl)imidazo[1,2-a]pyridin-3-yl]-N-[3-(methylsulfonyl)phenyl]pyrimidin-2-amine Example 16A 4-(2-chloroimidazo[1,2-a]pyridin-3-yl)-N-[3-(methylsulfonyl)phenyl]pyrimidin-2-amine The title compound was prepared as described in EXAMPLE 2F, substituting 3-methylsulfonylaniline for EXAMPLE 2E. MS ESI$^+$) m/e 399.0 (M+H)$^+$.

Example 16B

4-[2-(2-benzyl-1H-benzimidazol-6-yl)imidazo[1,2-a]pyridin-3-yl]-N-[3-(methylsulfonyl)phenyl]pyrimidin-2-amine The trifluoroacetic acid salt of the title compound was prepared as described in EXAMPLE 1K, substituting EXAMPLE 16A for EXAMPLE 1G. MS (ESI$^+$) m/e 572.2 (M+H)$^+$; $^1$H NMR (300 MHz, DMSO-d$_6$) δ ppm 10.21 (s, 1H), 9.59 (d, 1H), 8.39 (d, 1H), 8.07 (m, 1H), 7.92 (s, 1H), 7.82-7.74 (m, 2H), 7.68-7.52 (m, 4H), 7.41-7.32 (m, 5H), 7.17 (m, 2H), 6.65 (d, 1H), 4.44 (s, 2H), 3.10 (s, 3H).

Example 17

3-({4-[2-(2-benzyl-1H-benzimidazol-6-yl)imidazo[1,2-a]pyridin-3-yl]pyrimidin-2-yl}amino)-N,N-dimethylbenzenesulfonamide

Example 17A 3-(4-(2-chloroimidazo[1,2-a]pyridin-3-yl)pyrimidin-2-ylamino)-N,N-dimethylbenzenesulfonamide The title compound was prepared as described in EXAMPLE 2F, substituting 3-amino-N,N-dimethylbenzenesulfonamide for EXAMPLE 2E. MS (ESI$^+$) m/e 429.0 (M+H)$^+$.

Example 17B 3-({4-[2-(2-benzyl-1H-benzimidazol-6-yl)imidazo[1,2-a]pyridin-3-yl]pyrimidin-2-yl}amino)-N,N-dimethylbenzenesulfonamide The trifluoroacetic acid salt of the title compound was prepared as described in EXAMPLE 1K, substituting EXAMPLE 17A for EXAMPLE 1G. MS (ESI$^+$) m/e 601.2 (M+H)$^+$; $^1$H NMR (300 MHz, DMSO-d$_6$) δ ppm 10.17 (s, 1H), 9.56 (m, 1H), 8.38 (d, 1H), 8.21 (m, 1H), 8.08 (m, 1H), 7.92 (s, 1H), 7.81-7.51 (m, 5H), 7.43-7.30 (m, 7H), 6.66 (d, 1H), 4.43 (s, 2H), 2.60 (s, 6H).

Example 18

4-[2-(2-benzyl-1H-benzimidazol-6-yl)imidazo[1,2-a]pyridin-3-yl]-N-[4-(methylsulfonyl)phenyl]pyrimidin-2-amine

Example 18A 4-(2-chloroimidazo[1,2-a]pyridin-3-yl)-N-[4-(methylsulfonyl)phenyl]pyrimidin-2-amine The title compound was prepared as described in EXAMPLE 2F, substituting 4-methylsulfonylaniline for EXAMPLE 2E. MS (ESI$^+$) m/e 399.0 (M+H)$^+$.

Example 18B

4-[2-(2-benzyl-1H-benzimidazol-6-yl)imidazo[1,2-a]pyridin-3-yl]-N-[4-(methylsulfonyl)phenyl]pyrimidin-2-amine The trifluoroacetic acid salt of the title compound was prepared as described in EXAMPLE 1K, substituting EXAMPLE 18A for EXAMPLE 1G. MS (ESI$^+$) m/e 572.2 (M+H)$^+$; $^1$H NMR (300 MHz, DMSO-d$_6$) δ ppm 10.35 (s, 1H), 9.52 (d, 1H), 8.44 (d, 1H), 7.96 (m, 3H), 7.84-7.57 (m, 6H), 7.43-7.33 (m, 5H), 7.20 (m, 1H), 6.75 (d, 1H), 4.49 (s, 2H), 3.15 (s, 3H).

Example 19

6-[3-(2-anilinopyrimidin-4-yl)imidazo[1,2-a]pyridin-2-yl]-N-phenyl-1H-benzimidazol-2-amine

Example 19A 4-(2-(4-amino-3-nitrophenyl)imidazo[1,2-a]pyridin-3-yl)-N-(phenyl)pyrimidin-2-amine The title compound was prepared as described in EXAMPLE 1K substituting EXAMPLE 5A for EXAMPLE 1G and EXAMPLE 1H for EXAMPLE 1J. MS (ESI$^+$) m/e 424.0 (M+H)$^+$.

Example 19B 4-(2-(3,4-diaminophenyl)imidazo[1,2-a]pyridin-3-yl)-N-(phenyl)pyrimidin-2-amine The title compound was prepared as described in EXAMPLE 12A substituting EXAMPLE 19A for EXAMPLE 10A. MS (ESI$^+$) m/e 394.0 (M+H)$^+$.

Example 19C

6-[3-(2-anilinopyrimidin-4-yl)imidazo[1,2-a]pyridin-2-yl]-N-phenyl-1H-benzimidazol-2-amine The title compound was prepared as described in EXAMPLE 12B substituting EXAMPLE 19B for EXAMPLE 12A. MS (ESI$^+$) m/e 495.1 (M+H)$^+$, $^1$H NMR (500 MHz, Methanol-D$_4$) δ ppm 9.73 (d, 1 H) 8.12 (d, 1 H) 7.66 (d, 3 H) 7.54 (s, 1 H) 7.50 (m, 3 H) 7.41 (d, 1 H) 7.33 (m, 5 H) 7.04 (m, 2 H) 6.99 (m, 1 H) 6.57 (d, 1 H).

Example 20

4-{2-[2-(2-methoxybenzyl)-1H-benzimidazol-6-yl]imidazo[1,2-a]pyridin-3-yl}-N-(2-methoxy-4-morpholin-4-ylphenyl)pyrimidin-2-amine The trifluoroacetic acid salt of the title compound was prepared as described in EXAMPLE 1K, substituting EXAMPLE 14A for EXAMPLE 1G and EXAMPLE 3B for EXAMPLE 1J. MS (ESI$^+$) m/e 639.3 (M+H)$^+$; $^1$H NMR (300 MHz, DMSO-d$_6$) δ ppm 9.41 (m, 1H), 8.61 (m, 1H), 8.18 (d, 1H), 7.91 (m, 1H), 7.81-7.70 (m, 3H), 7.55 (m, 1H), 7.41 (m, 2H), 7.10-7.00 (m, 3H), 6.71 (d, 1H), 6.51 (m, 1H), 6.42 (d, 1H), 4.44 (s, 2H), 3.82 (s, 3H), 3.77 (s, 3H), 3.74 (m, 4H), 3.14 (m, 4H).

Example 21

4-{2-[2-(2,6-difluorobenzyl)-1H-benzimidazol-6-yl]imidazo[1,2-a]pyridin-3-yl}-N-(2-methoxy-4-morpholin-4-ylphenyl)pyrimidin-2-amine

Example 21A 2-(2,6-difluorobenzyl)-5-(4,4,5,5-tetramethyl-1,3,2-dioxaborolan-2-yl)-1H-benzo[d]imidazole The title compound was prepared as described in EXAMPLE 1J, substituting 2,6-difluorophenylacetic acid for phenylacetic acid. MS (ESI$^+$) m/e 371.1 (M+H)$^+$.

Example 21B

4-{2-[2-(2,6-difluorobenzyl)-1H-benzimidazol-6-yl]imidazo[1,2-a]pyridin-3-yl}-N-(2-methoxy-4-morpholin-4-ylphenyl)pyrimidin-2-amine The trifluoroacetic acid salt of the title compound was prepared as described in EXAMPLE 1K, substituting EXAMPLE 14A for EXAMPLE 1G and EXAMPLE 21A for EXAMPLE 1J. MS (ESI$^+$) m/e 645.3 (M+H)$^+$; $^1$H NMR (300 MHz, DMSO-d$_6$) δ ppm 9.52 (m, 1H), 8.78 (m, 1H), 8.16 (d, 1H), 7.85-7.80 (m, 2H), 7.73-7.39 (m, 4H), 7.22-7.15 (m, 3H), 6.72 (m, 1H), 6.53 (m, 1H), 6.42 (d, 1H), 4.44 (s, 2H), 3.82 (s, 3H) 3.75 (m, 4H), 3.15 (m, 4H).

Example 22

4-[2-(2-benzyl-1H-benzimidazol-5-yl)imidazo[1,2-a]pyridin-3-yl]-N-{2-methoxy-4-[4-(4-methylpiperazin-1-yl)piperidin-1-yl]phenyl}pyrimidin-2-amine

Example 22A 1-(1-(3-methoxy-4-nitrophenyl)piperidin-4-yl)-4-methylpiperazine Into a 5 mL microwave tube was charged 4-fluoro-2-methoxy-1-nitrobenzene (1 g, 0.584 mmol), 1-methyl-4-(piperidin-4-yl)piperazine (0.321 g, 1.753 mmol), triethylamine (0.244 mL, 1.753 mmol), and acetonitrile (1.948 mL). The reaction was heated in Biotage microwave reactor at 130° C. for 40 minutes. The solvent was removed under reduced pressure, and the reaction purified by flash chromatography using a gradient 100% CH$_2$Cl$_2$ to 1:1 CH$_2$Cl$_2$/methanol to provide the title compound. MS (ESI) m/e 335 (M+H)$^+$.

Example 22B 2-methoxy-4-(4-(4-methylpiperazin-1-yl)piperidin-1-yl)aniline

EXAMPLE 22A (1.16 g, 3.47 mmol) and methanol (20 mL) were added to 5% Pd—C, wet (0.232 g, 2.180 mmol) in a 250 mL stainless steel pressure bottle and stirred for 2 hours under H$_2$ at 30 psi at room temperature. The mixture was filtered through a nylon membrane and concentrated to provide the title compound. MS (ESI) m/e 305 (M+H)$^+$.

Example 22C 4-(2-chloroimidazo[1,2-a]pyridin-3-yl)-N-(2-methoxy-4-(4-(4-methylpiperazin-1-yl)piperidin-1-yl)phenyl)pyrimidin-2-amine The title compound was prepared as described in EXAMPLE 2F, substituting EXAMPLE 22B for EXAMPLE 2E. MS (ESI) m/e 533 (M+H)$^+$.

Example 22D

4-[2-(2-benzyl-1H-benzimidazol-5-yl)imidazo[1,2-a]pyridin-3-yl]-N-{2-methoxy-4-[4-(4-methylpiperazin-1-yl)piperidin-1-yl]phenyl}pyrimidin-2-amine The title compound was prepared as described in EXAMPLE 1K, substituting EXAMPLE 22C for EXAMPLE 1G. MS (ESI) m/e 705 (M+H)$^+$; $^1$H NMR (300 MHz, DMSO-d$_6$) δ 12.39 (d, 1H), 9.44 (m, 1H), 8.39 (s, 1H), 8.10 (dd, 1H), 7.71 (m, 1H), 7.60 (m, 1H), 7.46 (m, 1H), 7.33-7.41 (m, 5H), 7.31 (m, 1H), 7.25 (m, 1H), 7.11 (dt, 1H), 6.93 (t, 1H), 6.67 (d, 1H), 6.49 (dd, 1H), 6.39 (dd, 1H), 4.20 (s, 2H), 3.80 (s, 3H), 3.72 (d, 2H), 2.68 9t, 2H), 2.31 (m, 5H), 2.14 (s, 3H), 1.85 (m, 2H), 1.52 (m, 2H).

Example 23

4-[6-(2-benzyl-1H-benzimidazol-6-yl)imidazo[2,1-b][1,3]thiazol-5-yl]-N-phenylpyrimidin-2-amine

Example 23A 4-(6-chloroimidazo[2,1-b]thiazol-5-yl)-N-phenylpyrimidin-2-amine The title compound was prepared according to the procedure of EXAMPLE 1G, substituting EXAMPLE 7B for EXAMPLE 1D and 1-phenyl guanidine for EXAMPLE 1F. MS: (ESI$^+$) m/e 325.9 (M+H)$^+$.

Example 23B

4-[6-(2-benzyl-1H-benzimidazol-6-yl)imidazo[2,1-b][1,3]thiazol-5-yl]-N-phenylpyrimidin-2-amine The title compound was prepared according to the procedure of EXAMPLE 1K, substituting EXAMPLE 23A for EXAMPLE 1G. MS: (ESI$^+$) m/e 500.1 (M+H)$^+$; $^1$H NMR (500 MHz, DMSO-d$_6$) δ ppm 12.46 (bs, 1 H), 9.66 (s, 1H), 8.89 (s, 1H), 8.19 (d, 1H), 7.73 (d, 2H), 7.69 (s, 1H), 7.57 (d, 1H), 7.50 (d, 1H), 7.40-7.20 (m, 8H), 6.98 (t, 1H), 6.51 (d, 1H), 4.21 (s, 2 H).

Example 24

4-[6-(2-benzyl-1H-benzimidazol-6-yl)imidazo[2,1-b][1,3]thiazol-5-yl]-N-(2-methoxyphenyl)pyrimidin-2-amine

Example 24A 4-(6-chloroimidazo[2,1-b]thiazol-5-yl)-N-(2-methoxyphenyl)pyrimidin-2-amine The title compound was prepared according to the procedure of EXAMPLE 1G, substituting EXAMPLE 7B for EXAMPLE 1D and 1-(2-methoxyl-phenyl)phenyl guanidine for EXAMPLE 1F. MS: (ESI$^+$) m/e 357.9 (M+H)$^+$.

Example 24B

4-[6-(2-benzyl-1H-benzimidazol-6-yl)imidazo[2,1-b][1,3]thiazol-5-yl]-N-(2-methoxyphenyl)pyrimidin-2-amine The title compound was prepared according to the procedure of EXAMPLE 1K, substituting EXAMPLE 24A for EXAMPLE 1G. MS: (ESI$^+$) m/e 528.2 (M+H)$^+$; $^1$H NMR (500 MHz, DMSO-d$_6$) δ ppm 12.45 (bs, 1 H), 8.63 (bs, 1H), 8.60 (s, 1H), 8.13 (d, 1H), 7.82 (d, 1H), 7.67 (s, 1H), 7.64-7.60 (m, 2H), 7.57-7.54 (m, 2H), 7.39-7.32 (m, 4H), 7.25 (t, 1H), 7.14-7.08 (m, 2H), 6.94 (t, 1H), 6.48 (d, 1H), 4.21 (s, 2 H), 3.84 (s, 3H).

Example 25

4-[2-(2-benzyl-1H-benzimidazol-6-yl)imidazo[1,2-a]pyridin-3-yl]-N-(5-methyl-1H-pyrazol-3-yl)pyrimidin-2-amine

Example 25A 4-(2-chloroimidazo[1,2-a]pyridin-3-yl)-N-(5-methyl-1H-pyrazol-3-yl)pyrimidin-2-amine The title compound was prepared as described in EXAMPLE 2F, substituting 5-methyl-1H-pyrazol-3-amine for EXAMPLE 2E. MS ESI$^+$) m/e 325.9 (M+H)$^+$.

Example 25B

4-[2-(2-benzyl-1H-benzimidazol-6-yl)imidazo[1,2-a]pyridin-3-yl]-N-(5-methyl-1H-pyrazol-3-yl)pyrimidin-2-amine The trifluoroacetic acid salt of the title compound was prepared as described in EXAMPLE 1K, substituting EXAMPLE 25A for EXAMPLE 1G. MS (ESI$^+$) m/e 498.2 (M+H)$^+$; $^1$H NMR (300 MHz, DMSO-d$_6$) δ ppm 9.77 (m, 1H), 8.18 (d, 1H), 7.76-7.72 (m, 2H), 7.58 (d, 1H), 7.50 (m, 1H), 7.43-7.33 (m, 5H), 7.07 (m, 1H), 6.46 (d, 1H), 6.22 (s, 1H), 4.24 (s, 2H), 2.20 (s, 3H).

Example 26

4-[2-(2-benzyl-1H-benzimidazol-6-yl)imidazo[1,2-a]pyridin-3-yl]-N-(3-cyclopropyl-1H-pyrazol-5-yl)pyrimidin-2-amine

Example 26A 4-(2-chloroimidazo[1,2-a]pyridin-3-yl)-N-(3-cyclopropyl-1H-pyrazol-5-yl)pyrimidin-2-amine The title compound was prepared as described in EXAMPLE 2F, substituting 3-cyclopropyl-1H-pyrazol-5-amine for EXAMPLE 2E. MS ESI$^+$) m/e 351.9 (M+H)$^+$.

Example 26B

4-[2-(2-benzyl-1H-benzimidazol-6-yl)imidazo[1,2-a]pyridin-3-yl]-N-(3-cyclopropyl-1H-pyrazol-5-yl)pyrimidin-2-amine The trifluoroacetic acid salt of the title compound was prepared as described in EXAMPLE 1K, substituting EXAMPLE 26A for EXAMPLE 1G. MS (ESI$^+$) m/e 524.2 (M+H)$^+$; $^1$H NMR (300 MHz, DMSO-d$_6$) δ ppm 9.95 (m, 1H), 8.23 (d, 1H), 8.12 (m, 1H), 7.91 (m, 1H), 7.81-7.58 (m, 4H), 7.44-7.25 (m, 4H), 7.15 (m, 1H), 7.08 (m, 1H), 6.19 (s, 1H), 4.44 (s, 2H), 1.86 (m, 1H), 0.90 (m, 2H), 0.63 (m, 2H).

Example 27

N-(2-methoxy-4-morpholin-4-ylphenyl)-4-[2-(2-phenyl-1H-benzimidazol-6-yl)imidazo[1,2-a]pyridin-3-yl]pyrimidin-2-amine

Example 27A 2-phenyl-6-(4,4,5,5-tetramethyl-1,3,2-dioxaborolan-2-yl)-1H-benzo[d]imidazole The title compound was prepared as described in EXAMPLE 3B, substituting ethyl benzimidate hydrochloride for EXAMPLE 3A. MS (ESI$^+$) m/e 321.0 (M+H)$^+$

Example 27B 4-(2-chloroimidazo[1,2-a]pyridin-3-yl)-N-(2-methoxy-4-morpholinophenyl)pyrimidin-2-amine The trifluoroacetic acid salt of the title compound was prepared as described in EXAMPLE 2F, substituting 2-methoxy-4-morpholinoaniline for EXAMPLE 2E. MS (ESI$^+$) m/e 437.1 (M+H)$^+$

Example 27C

N-(2-methoxy-4-morpholinophenyl)-4-(2-(2-phenyl-1H-benzo[d]imidazol-6-yl)imidazo[1,2-a]pyridin-3-yl)pyrimidin-2-amine A 2 mL Biotage microwave vial was charged with EXAMPLE 27B (0.02 g, 0.046 mmol), EXAMPLE 27A (0.017 g, 0.054 mmol), cesium fluoride (0.021 g, 0.137 mmol), 1,2-dimethoxyethane (0.5 mL) and methanol (0.25 mL). The mixture was treated with tetrakis(triphenylphosphine)palladium (0) and the vessel was sealed under nitrogen. The reaction was heated at 155° C. for 35 minutes on a Biotage Initiator microwave reactor. The reaction was cooled to ambient temperature, diluted with 5 mL water, and extracted with 20 mL 10% methanol/CH$_2$Cl$_2$. The organic phase was concentrated and the residue was purified by reverse-phase HPLC on a Phenomenex C18 column (3×15 cm, 10 μm particle size) using a gradient of acetonitrile in 0.15% aqueous trifluoroacetic acid to provide the title compound as a trifluoroacetic acid salt. MS (ESI$^+$) m/e 595.3 (M+H)$^+$; $^1$H NMR (300 MHz, DMSO-d$_6$) δ ppm 3.14 (m, 4 H) 3.76 (m, 4 H) 3.83 (s, 3 H) 6.50 (m, 2 H) 6.72 (m, 1 H) 7.18 (m, 1 H) 7.40 (d, 1 H) 7.52-7.71 (m, 6 H) 7.75-7.91 (m, 3 H) 8.22 (m, 3 H) 8.78 (brs, 1 H) 9.53 (brs, 1 H).

Example 28

4-[2-(2-benzyl-1H-benzimidazol-5-yl)-5,6,7,8-tetrahydroimidazo[1,2-a]pyridin-3-yl]-N-phenylpyrimidin-2-amine EXAMPLE 4 (89 mg, 0.180 mmol) and methanol (1 ml) were added to 5% Pd—C, wet (178 mg, 1.673 mmol) in a 50 ml pressure bottle and stirred for 72 hours at 30 psi and 50° C. The mixture was filtered through a nylon membrane. The filtrate was concentrated to provide the title compound. MS (ESI) m/e 498 (M+H)$^+$; $^1$H NMR (300 MHz, DMSO-d$_6$) δ 9.58 (s, 1H), 8.29 (d, 1H), 7.65 (d, 1H), 7.28-7.36 (m, 5H), 7.18-7.25 (m, 4H), 6.91 (m, 1H), 6.57 (d, 1H), 4.14 (s, 2H), 2.87 (m, 2H), 1.92 9m, 4H).

Example 29

3-({4-[2-(2-benzyl-1H-benzimidazol-5-yl)imidazo[1,
2-a]pyridin-3-yl]pyrimidin-2-yl}amino)pyridin-2
(1H)-one

Example 29A 3-(4-(2-chloroimidazo[1,2-a]pyridin-3-yl)pyrimidin-
2-ylamino)pyridin-2(1H)-one A 5 mL reaction vial equipped with a stir bar was charged with EXAMPLE 2C (0.1 g, 0.377 mmol), 2-methoxypyridin-3-amine (0.049 g, 0.396 mmol), 2-propanol (2 ml) and 4 M HCl in 1,4-dioxane (0.133 mL, 0.453 mmol). The vessel was sealed and the mixture was heated on a thermal block at 120° C. for 3.5 hours. The reaction became homogeneous and then formed a suspension over time. The reaction was cooled to ambient temperature and the suspension was filtered. The solid collected was washed with 2-propanol (3×3 mL) and dried. The solid was suspended in 80 mL 20% methanol/CHCl$_3$, washed with saturated aqueous sodium bicarbonate and brine, dried over Na$_2$SO$_4$, and concentrated to provide the title compound. MS (APCI(+)) m/e 339.2 (M+H)$^+$.

Example 29B 3-({4-[2-(2-benzyl-1H-benzimidazol-5-yl)imidazo[1,
2-a]pyridin-3-yl]pyrimidin-2-yl}amino)pyridin-2
(1H)-one The trifluoroacetic acid salt of the title compound was prepared as described in EXAMPLE 27C, substituting EXAMPLE 29A for EXAMPLE 27B and EXAMPLE 1J for EXAMPLE 27A. MS (ESI$^+$) m/e 511.2 (M+H)$^+$, $^1$H NMR (300 MHz, DMSO-d$_6$) δ ppm 4.44 (s, 2 H) 6.16 (m, 1 H) 6.69 (d, 1 H) 7.02 (m, 1 H) 7.18 (m, 1 H) 7.31-7.43 (m, 6 H) 7.57 (m, 1 H) 7.66 (m, 1 H) 7.77 (m, 2 H) 7.91 (s, 1 H) 8.16 (d, 1 H) 8.41 (d, 1 H) 8.51 (s, 1 H) 9.46 (d, 1 H) 11.98 (d, 1 H).

Example 30

4-[6-(2-benzyl-1H-benzimidazol-6-yl)imidazo[2,1-
b][1,3]thiazol-5-yl]-N-{4-[4-(dimethylamino)piperi-
din-1-yl]-2-methoxyphenyl}pyrimidin-2-amine

Example 30A 4-(6-chloroimidazo[2,1-b]thiazol-5-yl)pyrimidin-2-
amine

The title compound was prepared according to the procedure of EXAMPLE 2A, substituting EXAMPLE 7B for EXAMPLE 1D. (ES r) m/e 251.8 (M+H)$^+$.

Example 30B 4-(6-chloroimidazo[2,1-b]thiazol-5-yl)pyrimidin-2-
ol

The title compound was prepared according to the procedure of EXAMPLE 2B, substituting EXAMPLE 30A for EXAMPLE 2A. (ESI(−)) m/e 250.8 (M−H)$^−$.

Example 30C 6-chloro-5-(2-chloropyrimidin-4-yl)imidazo[2,1-b]
thiazole

The title compound was prepared according to the procedure of EXAMPLE 2C, substituting EXAMPLE 30B for EXAMPLE 2B. (ES r) m/e 271.1 (M+H)$^+$.

Example 30D 1-(3-methoxy-4-nitrophenyl)-N,N-dimethylpiperi-
din-4-amine

A solution of 4-fluoro-2-methoxy-1-nitrobenzene (1.711 g, 10 mmol), N,N-dimethylpiperidin-4-amine (1.410 g, 11.00 mmol) and N-ethyl-N-isopropylpropan-2-amine (3.48 mL, 20.00 mmol) in anhydrous N,N-dimethylformamide (25 mL) was stirred at 70° C. overnight. The mixture was concentrated and the residue was mixed with water (60 mL), adjusted to pH 12, then extracted with CH$_2$Cl$_2$. The crude product was purified on a silica gel column eluting with 7.5% methanol in CH$_2$Cl$_2$ saturated with NH$_3$ to provide the title compound. (ESI$^+$) m/e 280.1 (M+H)$^+$.

Example 30E 1-(4-amino-3-methoxyphenyl)-N,N-dimethylpiperi-
din-4-amine

EXAMPLE 30D (2.7 g, 9.67 mmol), iron (2.70 g, 48.3 mmol) and ammonium chloride (0.517 g, 9.67 mmol) were mixed with absolute ethanol (20 mL) and water (5 mL). The mixture was refluxed for 2 hours and filtered through a nylon membrane. The filtrate was concentrated to remove most of the ethanol. The aqueous solution was adjusted to pH 13-14 and extracted with CH$_2$Cl$_2$. The organic solution was dried (MgSO$_4$), filtered and concentrated to provide the title compound. (ESI$^+$) m/e 250.2 (M+H)$^+$.

Example 30F 4-(6-chloroimidazo[2,1-b]thiazol-5-yl)-N-(4-(4-
(dimethylamino)piperidin-1-yl)-2-methoxyphenyl)
pyrimidin-2-amine The title compound was prepared according to the procedure of EXAMPLE 2F, substituting EXAMPLE 30C for EXAMPLE 2C and EXAMPLE 30E for EXAMPLE 2E. (ESI$^+$) m/e 484.4 (M+H)$^+$.

Example 30G

4-[6-(2-benzyl-1H-benzimidazol-6-yl)imidazo[2,1-
b][1,3]thiazol-5-yl]-N-{4-[4-(dimethylamino)piperi-
din-1-yl]-2-methoxyphenyl}pyrimidin-2-amine The title compound was prepared according to the procedure of EXAMPLE 1K, substituting EXAMPLE 30F for EXAMPLE 1G. MS: (ESI$^+$) m/e 656.3 (M+H)$^+$; $^1$H NMR (500 MHz, DMSO-d$_6$) δ ppm 12.45, 12.39 (d, 1 H), 8.44 (bs, 1H), 8.04 (dd, 1H), 7.60 (d, 1H), 7.40-7.30 (m, 8H), 7.25-7.20 (m, 2H), 6.67 (s, 1H), 6.51 (d, 1H), 6.38 (dd, 1H), 4.20 (s, 2 H), 4.11-4.08(m, 1H), 3.78 (s, 3H), 3.72(d, 2H), 2.66-2.71(t, 2H), 2.21(s, 6H), 1.85(d, 2H), 1.55-1.50(m, 2H).

Example 31

N$^1$-{4-[6-(2-benzyl-1H-benzimidazol-6-yl)imidazo[2,1-b][1,3]thiazol-5-yl]pyrimidin-2-yl}-2-methoxy-N$^4$,N$^4$-dimethylbenzene-1,4-diamine

Example 31A 3-methoxy-N,N-dimethyl-4-nitroaniline

The title compound was prepared according to the procedure of EXAMPLE 30D, substituting dimethylamine for N,N-dimethylpiperidin-4-amine. MS: (ESI$^+$) m/e 197.2 (M+H)$^+$.

Example 31B 3-methoxy-N1,N1-dimethylbenzene-1,4-diamine

The title compound was prepared according to the procedure of EXAMPLE 30E, substituting EXAMPLE 31A for EXAMPLE 30D. MS: (ESI$^+$) m/e 167.1 (M+H)$^+$.

Example 31C

N1-(4-(6-chloroimidazo[2,1-b]thiazol-5-yl)pyrimidin-2-yl)-2-methoxy-N4,N4-dimethylbenzene-1,4-diamine The title compound was prepared according to the procedure of EXAMPLE 2F, substituting EXAMPLE 30C for EXAMPLE 2C and EXAMPLE 31B for EXAMPLE 2E. (ESI$^+$) m/e 400.9 (M+H)$^+$.

Example 31D

N$^1$-{4-[6-(2-benzyl-1H-benzimidazol-6-yl)imidazo[2,1-b][1,3]thiazol-5-yl]pyrimidin-2-yl}-2-methoxy-N$^4$,N$^4$-dimethylbenzene-1,4-diamine The title compound was prepared according to the procedure of EXAMPLE 1K, substituting EXAMPLE 31C for EXAMPLE 1G. MS: (ESI$^+$) m/e 573.2 (M+H)$^+$; $^1$H NMR (500 MHz, DMSO-d$_6$) δ ppm 12.45, 12.39 (d, 1 H), 8.40 (s, 1H), 8.02 (m, 1H), 7.60 (s, 1H), 7.38-7.23 (m, 10H), 6.44 (d, 1H), 6.37-6.34 (m, 2H), 4.21 (s, 2 H), 3.78 (s, 3H), 2.93 (s, 6H).

Example 32

4-[2-(2-benzyl-1H-benzimidazol-6-yl)imidazo[1,2-a]pyridin-3-yl]-N-(4-chloro-2-methoxyphenyl)pyrimidin-2-amine

Example 32A

N-(4-chloro-2-methoxyphenyl)-4-(2-chloroimidazo[1,2-a]pyridin-3-yl)pyrimidin-2-amine The title compound was prepared as described in EXAMPLE 2F, substituting 4-chloro-2-methoxyaniline for EXAMPLE 2E. MS (ESI) m/e 386 (M+H)$^+$.

Example 32B

N$^1$-{4-[6-(2-benzyl-1H-benzimidazol-6-yl)imidazo[2,1-b][1,3]thiazol-5-yl]pyrimidin-2-yl}-2-methoxy-N$^4$,N$^4$-dimethylbenzene-1,4-diamine The trifluoroacetic acid salt of the title compound was prepared as described in EXAMPLE 1K, substituting EXAMPLE 32A for EXAMPLE 1G. MS (ESI) m/e 558 (M+H)$^+$; $^1$H NMR (300 MHz, DMSO-d$_6$) δ 9.47 (d, 1H), 8.80 (s, 1H), 8.29 (d, 1H), 7.98 (s, 1H), 7.84 (m, 3H), 7.72 (dd, 1H), (7.64 (m, 1H), 7.44 (m, 4H), 7.38 (m, 2H), 7.20 (d, 1H), 7.18 (m, 1H), 6.97 (dd, 1H), 6.55 (d, 1H), 4.53 (s, 2H), 3.89 (s, 3H).

Example 33

N$^1$-(4-{6-[2-(2-chlorobenzyl)-1H-benzimidazol-6-yl]imidazo[2,1-b][1,3]thiazol-5-yl}pyrimidin-2-yl)-2-methoxy-N$^4$,N$^4$-dimethylbenzene-1,4-diamine The trifluoroacetic acid salt of the title compound was prepared according to the procedure of EXAMPLE 1K, substituting EXAMPLE 31C for EXAMPLE 1G and EXAMPLE 9A for EXAMPLE 1J. MS: (ESI$^+$) m/e 607.1 (M+H)$^+$; $^1$H NMR (500 MHz, DMSO-d$_6$) δ ppm 9.20 (bs, 1 H), 8.58 (bs, 1H), 8.03 (d, 1H), 7.91 (s, 1H), 7.79 (d, 1H), 7.66 (dd, 1H), 7.58-7.53 (m, 2H), 7.22-7.38 (m, 4H), 6.63 (s, 1H), 6.50 (d, 1H), 6.41 (d, 1H), 4.63 (s, 2H), 3.80 (s, 3H), 3.00 (s, 6H).

Example 34

2-methoxy-N$^1$-(4-{6-[2-(2-methoxybenzyl)-1H-benzimidazol-6-yl]imidazo[2,1-b][1,3]thiazol-5-yl}pyrimidin-2-yl)-N$^4$,N$^4$-dimethylbenzene-1,4-diamine The trifluoroacetic acid salt of the title compound was prepared according to the procedure of EXAMPLE 1K, substituting EXAMPLE 31C for EXAMPLE 1G and EXAMPLE 3B for EXAMPLE 1J. MS: (ESI$^+$) m/e 603.2 (M+H)$^+$; $^1$H NMR (500 MHz, DMSO-d$_6$) δ ppm 9.04 (bs, 1 H), 8.56 (bs, 1H), 8.03 (d, 1H), 7.93 (s, 1H), 7.81 (d, 1H), 7.70 (d, 1H), 7.44-7.36 (m, 4H), 7.08 (d, 1H), 7.01 (t, 1H), 6.62 (s, 1H), 6.48 (d, 1H), 6.39 (d, 1H), 4.46 (s, 2H), 3.88 (s, 3H), 3.76 (s, 3H), 2.99 (s, 6H).

Example 35

4-[2-(2-benzyl-1H-benzimidazol-5-yl)imidazo[1,2-a]pyridin-3-yl]-N-(1-methyl-1H-pyrazol-4-yl)pyrimidin-2-amine

Example 35A 4-(2-chloroimidazo[1,2-a]pyridin-3-yl)-N-(1-methyl-1H-pyrazol-4-yl)pyrimidin-2-amine A 5 mL reaction vial equipped with a stir bar was charged with EXAMPLE 2C (0.1 g, 0.377 mmol), 1-methyl-1H-pyrazol-4-amine (0.039 g, 0.404 mmol), 2-propanol (2 ml) and 4 M HCl in dioxane (0.094 mL, 0.377 mmol). The vessel was sealed and the mixture was heated on a thermal block at 120° C. for 5 hours. The reaction was cooled to ambient temperature. The suspension was filtered and solid collected was washed with 2-propanol (1.5 mL) and dried. The solid was suspended in 80 mL 20% methanol/CHCl$_3$, washed with saturated aqueous sodium bicarbonate and brine, dried over Na$_2$SO$_4$, and concentrated. The concentrate was purified by flash chromatography on a 5 g silica gel column eluting with a gradient of methanol in CH$_2$Cl$_2$ to provide the title compound. MS (ESI$^+$) m/e 325.9 (M+H)$^+$.

Example 35B

The title compound was prepared as described in EXAMPLE 27C, substituting EXAMPLE 35A for EXAMPLE 27B and EXAMPLE 1J for EXAMPLE 27A. MS (ESI$^+$) m/e 498.2 (M+H)$^+$, $^1$H NMR (300 MHz, methanol-d$_4$) δ ppm 3.82 (s, 3 H) 4.53 (s, 2 H) 6.55 (m, 1 H) 7.31 (m, 1 H) 7.42 (m, 5 H) 7.56 (s, 1 H) 7.74-7.88 (m, 5 H) 7.98 (s, 1 H) 8.25 (d, 1 H) 9.61 (brs, 1 H).

Example 36

2-[4-({4-[2(2-phenyl-1H-benzimidazol-5-yl)imidazo[1,2-a]pyridin-3-yl]pyrimidin-2-yl}amino)-1H-pyrazol-1-yl]ethanol

Example 36A 2-(4-(4-(2-chloroimidazo[1,2-a]pyridin-3-yl)pyrimidin-2-ylamino)-1H-pyrazol-1-yl)ethanol The title compound was prepared as described in EXAMPLE 35A, substituting 2-(4-amino-1H-pyrazol-1-yl)ethanol hydrochloride (WO2007/099326) for 1-methyl-1H-pyrazol-4-amine. MS (ESI$^+$) m/e 355.9 (M+H)$^+$.

Example 36B

The title compound was prepared as described in EXAMPLE 27C, substituting EXAMPLE 36A for EXAMPLE 27B. Purification of the crude reaction product was performed using reverse-phase HPLC on a Phenomenex C18 column (3×15 cm) using a gradient of acetonitrile in 0.1% aqueous ammonium hydroxide. MS (ESI$^+$) m/e 514.1 (M+H)$^+$, $^1$H NMR (300 MHz, methanol-d$_4$) δ ppm 3.87 (t, 2 H) 4.17 (t, 2 H) 6.58 (m, 1H) 7.28 (m, 1 H) 7.64 (m, 5 H) 7.74 (m, 1 H) 7.81 (m, 2 H) 7.96 (m, 2 H) 8.13 (m, 2 H) 8.25 (m, 1 H) 9.66 (brs, 1 H).

Example 37

2-[4-({4-[2-(2-benzyl-1H-benzimidazol-5-yl)imidazo[1,2-a]pyridin-3-yl]pyrimidin-2-yl}amino)-1H-pyrazol-1-yl]ethanol The title compound was prepared as described in EXAMPLE 27C, substituting EXAMPLE 36A for EXAMPLE 27B and EXAMPLE 1J for EXAMPLE 27A. Purification of the crude reaction product was performed using reverse-phase HPLC on a Phenomenex C18 column (3×15 cm) using a gradient of acetonitrile: in 0.1% aqueous ammonium hydroxide. MS (ESI$^+$) m/e 528.2 (M+H)$^+$, $^1$H NMR (300 MHz, methanol-d$_4$) δ ppm 3.70 (m, 2 H) 4.06 (m, 2 H) 4.20 (s, 2 H) 4.84 (m, 1 H) 6.45 (m, 1 H) 7.07 (m, 1 H) 7.20-7.42 (m, 7 H) 7.49 (m, 3 H) 7.73 (m, 2 H) 7.90 (m, 1 H) 8.23 (m, 1 H) 9.56 (m, 1 H) 12.36 (brs, 1 H).

Example 38

N-(4-fluorophenyl)-4-[2-(2-phenyl-1H-benzimidazol-6-yl)imidazo[1,2-a]pyridin-3-yl]pyrimidin-2-amine

Example 38A 4-(2-chloroimidazo[1,2-a]pyridin-3-yl)-N-(4-fluorophenyl)pyrimidin-2-amine The title compound was prepared as described in EXAMPLE 2F substituting 4-fluoroaniline for EXAMPLE 2E. MS (ESI$^+$) m/e 340.0 (M+H)$^+$.

Example 38B

N-(4-fluorophenyl)-4-[2-(2-phenyl-1H-benzimidazol-6-yl)imidazo[1,2-a]pyridin-3-yl]pyrimidin-2-amine The title compound was prepared as described in EXAMPLE 27C substituting EXAMPLE 38A for EXAMPLE 27B. MS (ESI$^+$) m/e 498.1 (M+H)$^+$, $^1$H NMR (500 MHz, DMSO-d$_6$) δ ppm 13.02 (d, 1 H) 9.78 (s, 1 H) 9.53 (m, 1 H) 8.31 (s, 1 H) 8.19 (d, 2 H) 7.75 (m, 4 H) 7.56-7.65 (m, 3 H) 7.50 (m, 3 H) 7.11 (m, 3 H) 6.63 (s, 1 H).

Example 39

4-[2-(2-benzyl-1H-benzimidazol-5-yl)imidazo[1,2-a]pyridin-3-yl]-N-(4-fluorophenyl)pyrimidin-2-amine The title compound was prepared as described in EXAMPLE 27C substituting EXAMPLE 38A for EXAMPLE 27B and EXAMPLE 1J for EXAMPLE 27A. MS (ESI$^+$) m/e 512.1 (M+H)$^+$, $^1$H NMR (500 MHz, DMSO-d$_6$) δ ppm 12.50 (m, 1 H) 9.76 (s, 1 H) 9.56 (d, 1 H) 8.26 (d, 1 H) 7.73 (m, 4 H) 7.55 (d, 1 H) 7.48 (t, 1 H) 7.36 (m, 5 H) 7.25 (t, 1 H) 7.12 (t, 2 H) 7.07 (t, 1 H) 6.56 (d, 1 H) 4.20 (s, 2 H).

Example 40

N-(2,4-difluorophenyl)-4-[2-(2-phenyl-1H-benzimidazol-6-yl)imidazo[1,2-a]pyridin-3-yl]pyrimidin-2-amine

Example 40A 4-(2-chloroimidazo[1,2-a]pyridin-3-yl)-N-(2,4-difluorophenyl)pyrimidin-2-amine The title compound was prepared as described in EXAMPLE 2F substituting 2,4-difluoroaniline for EXAMPLE 2E. MS (ESI$^+$) m/e 357.9 (M+H)$^+$.

Example 40B

N-(2,4-difluorophenyl)-4-[2-(2-phenyl-1H-benzimidazol-6-yl)imidazo[1,2-a]pyridin-3-yl]pyrimidin-2-amine The title compound was prepared as described in EXAMPLE 27C substituting EXAMPLE 40A for EXAMPLE 27B. MS (ESI⁺) m/e 516.1 (M+H)⁺, ¹H NMR (500 MHz, DMSO-d₆) δ ppm 13.05 (m, 1H) 9.49 (s, 1H) 9.34 (s, 1 H) 8.21 (m, 3 H) 7.79 (s, 1 H) 7.75 (d, 1 H) 7.70 (m, 2 H) 7.58 (m, 2 H) 7.45-7.53 (m, 3 H) 7.39 (m, 1 H) 7.11 (m, 1 H) 7.02 (t, 1 H) 6.57 (d, 1 H).

Example 41

4-[2-(2-benzyl-1H-benzimidazol-5-yl)imidazo[1,2-a]pyridin-3-yl]-N-(2,4-difluorophenyl)pyrimidin-2-amine The title compound was prepared as described in EXAMPLE 27C substituting EXAMPLE 40A for EXAMPLE 27B and EXAMPLE 1J for EXAMPLE 27A. MS (ESI⁺) m/e 530.1 (M+H)⁺, ¹H NMR (500 MHz, DMSO-d₆) δ ppm 12.40 (m, 1 H) 9.49 (s, 1 H) 9.31 (s, 1 H) 8.18 (d, 1 H) 7.72 (d, 1 H) 7.68 (m, 2 H) 7.55 (m, 1 H) 7.47 (m, 1 H) 7.32-7.41 (m, 6 H) 7.25 (t, 1 H) 7.09 (m, 1 H) 7.00 (t, 1 H) 6.51 (d, 1 H) 4.21 (s, 2 H).

Example 42

N-[2-(pyrrolidin-1-ylmethyl)phenyl]-4-(6-{2-[2-(trifluoromethyl)benzyl]-1H-benzimidazol-6-yl}imidazo[2,1-b][1,3]thiazol-5-yl)pyrimidin-2-amine

Example 42A 4-(6-chloroimidazo[2,1-b]thiazol-5-yl)-N-(2-(pyrrolidin-1-ylmethyl)phenyl)pyrimidin-2-amine The title compound was prepared according to the procedure of EXAMPLE 2F, substituting EXAMPLE 30C for EXAMPLE 2C and 2-(pyrrolidin-1-y)methyl aniline for EXAMPLE 2E. (ESI⁺) m/e 411.0 (M+H)⁺.

Example 42B 6-(4,4,5,5-tetramethyl-1,3,2-dioxaborolan-2-yl)-2-(2-(trifluoromethyl)benzyl)-1H-benzo[d]imidazole The title compound was prepared according to the procedure of EXAMPLE 1J, substituting 2-trifluoromethylphenyl acetic acid for phenyl acetic acid. MS: (ESI⁺) m/e 403.3 (M+H)⁺

Example 42C

N-[2-(pyrrolidin-1-ylmethyl)phenyl]-4-(6-{2-[2-(trifluoromethyl)benzyl]-1H-benzimidazol-6-yl}imidazo[2,1-b][1,3]thiazol-5-yl)pyrimidin-2-amine The title compound was prepared according to the procedure of EXAMPLE 1K, substituting EXAMPLE 42A for EXAMPLE 1G and EXAMPLE 42B for EXAMPLE 1J. MS: (ESI⁺) m/e 651.2 (M+H)⁺; ¹H NMR (500 MHz, DMSO-d₆) δ ppm 12.48, 12.44 (d, 1 H), 10.47 (bs, 1H), 8.51 (s, 1H), 8.21 (dd, 1H), 8.16 (d, 1H), 7.77 (d, 1H), 7.67 (t, 1H), 7.65 (d, 1H), 7.55-7.45 (m, 4H), 7.40 (dd, 1H), 7.28-7.23 (m, 2H), 6.97 (t, 1H), 6.56 (dd, 1H), 4.42 (s, 2 H), 3.76 (s, 2H), 2.50 (s, 4H), 1.80 (s, 4H).

Example 43

4-[2-(2-benzyl-1H-benzimidazol-6-yl)imidazo[1,2-a]pyridin-3-yl]-N-[2-methoxy-5-(methylsulfonyl)phenyl]pyrimidin-2-amine

Example 43A 4-(2-chloroimidazo[1,2-a]pyridin-3-yl)-N-(2-methoxy-5-(methylsulfonyl)phenyl)pyrimidin-2-amine The title compound was prepared as described in EXAMPLE 2F, substituting 2-methoxy-5-(methylsulfonyl)aniline for EXAMPLE 2E. MS ESI⁺) m/e 429.9 (M+H)⁺.

Example 43B

4-[2-(2-benzyl-1H-benzimidazol-6-yl)imidazo[1,2-a]pyridin-3-yl]-N-[2-methoxy-5-(methylsulfonyl)phenyl]pyrimidin-2-amine The title compound was prepared as described in EXAMPLE 1K, substituting EXAMPLE 43A for EXAMPLE 1G. MS ESI⁺) m/e 602.2 (M+H)⁺; ¹H NMR (300 MHz, dimethylsulfoxide-d₆) δ ppm 9.53 (m, 1H), 8.79 (s, 1H), 8.56 (m, 1H), 8.28 (m, 1H), 7.73 (d, 1H), 7.68-7.58 (m, 2H), 7.48 (m, 2H), 7.39-7.31 (m, 6H), 7.05 (m, 1H), 6.57 (m, 1H), 4.20 (s, 2H), 3.99 (s, 3H), 3.13 (s, 3H).

Example 44

N-(1-methyl-1H-pyrazol-4-yl)-4-[2-(2-phenyl-1H-benzimidazol-5-yl)imidazo[1,2-a]pyridin-3-yl]pyrimidin-2-amine The trifluoroacetic acid salt of the title compound was prepared as described in EXAMPLE 27C, substituting EXAMPLE 35A for EXAMPLE 27B. MS (ESI⁺) m/e 484.1 (M+H)⁺, ¹H NMR (300 MHz, methanol-d₄) δ ppm 3.84 (s, 3 H) 6.59 (m, 1 H) 7.37 (m, 1 H) 7.59 (s, 1 H) 7.63-7.93 (m, 8 H) 8.02 (m, 1 H) 8.13 (m, 2 H) 8.30 (d, 1 H) 9.67 (brs, 1 H).

Example 45

4-[2-(2-benzyl-1H-benzimidazol-6-yl)imidazo[1,2-a]pyridin-3-yl]-N-[2-methoxy-5-(trifluoromethyl)phenyl]pyrimidin-2-amine

Example 45A 4-(2-chloroimidazo[1,2-a]pyridin-3-yl)-N-(2-methoxy-5-(trifluoromethyl)phenyl)pyrimidin-2-amine The title compound was prepared as described in EXAMPLE 2F, substituting 2-methoxy-5-(trifluoromethyl) aniline for EXAMPLE 2E. MS ESI⁺) m/e 419.9 (M+H)⁺.

Example 45B

4-[2-(2-benzyl-1H-benzimidazol-6-yl)imidazo[1,2-a]pyridin-3-yl]-N-[2-methoxy-5-(trifluoromethyl)phenyl]pyrimidin-2-amine The title compound was prepared as described in EXAMPLE 1K, substituting EXAMPLE 45A for EXAMPLE 1G. MS ESI+) m/e 592.2 (M+H)+; 1H NMR (300 MHz, dimethylsulfoxide-d6) δ ppm 12.40 (d, 1H), 9.51 (m, 1H), 8.68 (s, 1H), 8.44 (m, 1H), 8.29 (m, 1H), 7.73 (d, 1H), 7.62 (m, 1H), 7.51-7.25 (m, 9H), 7.00 (t, 1H), 6.58 (m, 1H), 4.20 (s, 2H), 3.97 (s, 3H).

Example 46

N-{4-[(dimethylamino)methyl]phenyl}-4-(6-{2-[2-(trifluoromethyl)benzyl]-1H-benzimidazol-6-yl}imidazo[2,1-b][1,3]thiazol-5-yl)pyrimidin-2-amine

Example 46A 4-(6-chloroimidazo[2,1-b]thiazol-5-yl)-N-(4-((dimethylamino)methyl)phenyl)pyrimidin-2-amine The title compound was prepared according to the procedure of EXAMPLE 2F, substituting EXAMPLE 30C for EXAMPLE 2C and 4-(dimethylamino)methyl aniline for EXAMPLE 2E. (ESI+) m/e 384.9 (M+H)+.

Example 46B

N-{4-[(dimethylamino)methyl]phenyl}-4-(6-{2-[2-(trifluoromethyl)benzyl]-1H-benzimidazol-6-yl}imidazo[2,1-b][1,3]thiazol-5-yl)pyrimidin-2-amine The title compound was prepared according to the procedure of EXAMPLE 1K, substituting EXAMPLE 46A for EXAMPLE 1G and EXAMPLE 42B for EXAMPLE 1J. MS: (ESI+) m/e 625.2 (M+H)+; 1H NMR (500 MHz, DMSO-d6) δ ppm 12.48, 12.43 (d, 1 H), 9.63 (d, 1H), 8.86 (s, 1H), 8.19 (dd, 1H), 7.76 (d, 1H), 7.69 (s, 1H), 7.65 (d, 2H), 7.60 (d, 1H), 7.55-7.45 (m, 4H), 7.40 (dd, 1H), 7.20 (d, 2H), 6.50 (dd, 1H), 4.42 (s, 2 H), 3.44 (s, 2H), 2.15 (s, 6H).

Example 47

1-{[4-({4-[2-(2-benzyl-1H-benzimidazol-5-yl)imidazo[1,2-a]pyridin-3-yl]pyrimidin-2-yl}amino)-3-methoxyphenyl]amino}-2-methylpropan-2-ol

Example 47A 1-(3-methoxy-4-nitrophenylamino)-2-methylpropan-2-ol

A 20 mL reaction vial equipped with a stir bar was charged with 4-fluoro-2-methoxy-1-nitrobenzene (0.5 g, 2.92 mmol), 1-amino-2-methylpropan-2-ol (0.313 g, 3.51 mmol), N-methyl-2-pyrrolidinone (7.3 mL) and Hunig's base (N,N-diisopropylethylamine) (0.76 g, 5.84 mmol). The vessel was sealed and the reaction was heated on a thermal block at 80° C. for 24 hours. The reaction was cooled to ambient temperature, treated with water (40 mL) and extracted with ethyl acetate (3×60 mL). The combined organic layers were washed with brine (25 mL), dried over Na2SO4, filtered, and concentrated. The concentrate was purified by flash chromatography on a 10 g silica gel column with 1% methanol/CH2Cl2 to provide the title compound.

Example 47B 1-(4-amino-3-methoxyphenylamino)-2-methylpropan-2-ol

EXAMPLE 47A (0.9 g, 2.81 mmol) in methanol (28 mL) was added to 5% Pd/C (wet, 0.180 g) in a 250 mL stainless steel pressure bottle, and the mixture was shaken under 30 psi of hydrogen at 50° C. for 10 minutes. The mixture was filtered through a nylon membrane and the filtrate was concentrated. The concentrate was purified by flash chromatography on a 10 g silica gel column eluting with a gradient of from 0% to 2% methanol/CH2Cl2 to provide the title compound. MS (ESI+) m/e 210.9 (M+H)+.

Example 47C 1-(4-(4-(2-chloroimidazo[1,2-a]pyridin-3-yl)pyrimidin-2-ylamino)-3-methoxyphenylamino)-2-methylpropan-2-ol A 20 mL reaction vial equipped with a stir bar was charged with EXAMPLE 2C (0.36 g, 1.358 mmol), EXAMPLE 47B (80%, 0.375 g, 1.426 mmol) and Hunig's base (0.474 mL, 2.72 mmol) in N-methyl-2-pyrrolidinone (5 ml) and was sealed. The reaction was heated on a thermal block at 98° C. for 44 hours. The reaction was cooled to ambient temperature, diluted with water (25 mL) and extracted with 1:1 ether/ethyl acetate (2×80 mL). The combined organic layers were washed with water (50 mL) and brine (2×50 mL), dried over Na2SO4 and concentrated. The concentrate was triturated with ethyl ether (6 mL) and purified by flash chromatography on an 8 g silica gel column eluting with a gradient of from 0% to 1% methanol/CH2Cl2 to provide the title compound. MS (ESI+) m/e 439.0 (M+H)+

Example 47D

1-{[4-({4-[2-(2-benzyl-1H-benzimidazol-5-yl)imidazo[1,2-a]pyridin-3-yl]pyrimidin-2-yl}amino)-3-methoxyphenyl]amino}-2-methylpropan-2-ol The trifluoroacetic acid salt of the title compound was prepared as described in EXAMPLE 27C, substituting EXAMPLE 47C for EXAMPLE 27B and EXAMPLE 1J for EXAMPLE 27A. MS (ESI+) m/e 611.3 (M+H)+, 1H NMR (300 MHz, methanol-d4) δ ppm 1.32 (s, 6 H) 3.22 (s, 2 H) 3.89 (s, 3 H) 4.56 (s, 2 H) 6.55 (m, 2 H) 6.72 (m, 1 H) 7.24 (m, 1 H) 7.43 (m, 5 H) 7.57 (m, 1 H) 7.70-7.89 (m, 4 H) 7.99 (m, 2 H) 9.78 (m, 1 H).

Example 48

2-[[4-({4-[2-(2-benzyl-1H-benzimidazol-6-yl)imidazo[1,2-a]pyridin-3-yl]pyrimidin-2-yl}amino)-3-methoxyphenyl](methyl)amino]ethanol

Example 48A 2-((3-methoxy-4-nitrophenyl)(methyl)amino)ethanol

The title compound was prepared as described in EXAMPLE 47A, substituting 2-(methylamino)ethanol for 1-amino-2-methylpropan-2-ol. MS (ESI+) m/e 226.9 (M+H)+.

Example 48B 2-((4-amino-3-methoxyphenyl)(methyl)amino)ethanol

The title compound was prepared as described in EXAMPLE 2E, substituting EXAMPLE 48A for EXAMPLE 2D. MS (DCI+) m/e 197.1 (M+H)+.

Example 48C 2-((4-(4-(2-chloroimidazo[1,2-a]pyridin-3-yl)pyrimidin-2-ylamino)-3-methoxyphenyl)(methyl)amino) ethanol The title compound was prepared as described in EXAMPLE 2F, substituting EXAMPLE 48B for EXAMPLE 2E. MS (ESI+) m/e 425.0 (M+H)+.

Example 48D

2-[[4-({4-[2-(2-benzyl-1H-benzimidazol-6-yl)imidazo[1,2-a]pyridin-3-yl]pyrimidin-2-yl}amino)-3-methoxyphenyl](methyl)amino]ethanol The trifluoroacetic acid salt of the title compound was prepared as described in EXAMPLE 27C, substituting EXAMPLE 48C for EXAMPLE 27B and EXAMPLE 1J for EXAMPLE 27A. MS (ESI+) m/e 597.3 (M+H)+, $^1$H NMR (300 MHz, methanol-$d_4$) δ ppm 3.24 (s, 3 H) 3.65 (s, 4 H) 3.98 (s, 3 H) 4.54 (s, 2 H) 6.61 (d, 1 H) 6.90 (m, 1 H) 7.03 (m, 1 H) 7.24 (m, 1 H) 7.42 (m, 5 H) 7.70-7.87 (m, 4 H) 7.99 (m, 1 H) 8.07 (m, 1 H) 8.16 (d, 1 H) 9.67 (d, 1 H).

Example 49

N-[4-({4-[2-(2-benzyl-1H-benzimidazol-5-yl)imidazo[1,2-a]pyridin-3-yl]pyrimidin-2-yl}amino)-3-methoxyphenyl]glycine

Example 49A tert-butyl 2-(3-methoxy-4-nitrophenylamino)acetate

The title compound was prepared as described in EXAMPLE 47A, substituting tert-butyl 2-aminoacetate for 1-amino-2-methylpropan-2-ol. MS (ESI+) m/e 282.9 (M+H)+

Example 49B tert-butyl 2-(4-amino-3-methoxyphenylamino)acetate

EXAMPLE 49A (0.466 g, 1.651 mmol) in methanol (5 mL) was added to 5% Pd/C (wet, 0.093 g) in a 20 mL pressure bottle and stirred under 60 psi of hydrogen at 50° C. for 1 hour. The mixture was filtered through a polypropylene membrane filter, and the filtrate was concentrated to provide the title compound. MS (DCI+) m/e 253.1 (M+H)+

Example 49C tert-butyl 2-(4-(4-(2-chloroimidazo[1,2-a]pyridin-3-yl)pyrimidin-2-ylamino)-3-methoxyphenylamino) acetate A 5 mL reaction vial equipped with a stir bar was charged with EXAMPLE 2C (0.225 g, 0.849 mmol), EXAMPLE 49B (0.236 g, 0.934 mmol) and Hunig's base (0.296 mL, 1.697 mmol) in N-methyl-2-pyrrolidinone (3.6 ml) and was sealed. The reaction was heated on a thermal block at 95° C. for 60 hours. The reaction was cooled to ambient temperature, diluted with 60 mL water and the resulting suspension was filtered. The solid collected was washed with water and dried under vacuum. The residue was purified by flash chromatography on a 10 g silica gel column eluting with a gradient of from 0% to 30% ethyl acetate/hexanes to provide the title compound. MS (ESI+) m/e 481.0 (M+H)+.

Example 49D

N-[4-({4-[2-(2-benzyl-1H-benzimidazol-5-yl)imidazo[1,2-a]pyridin-3-yl]pyrimidin-2-yl}amino)-3-methoxyphenyl]glycine A 2 mL Biotage microwave reaction vial was charged with EXAMPLE 49C (0.06 g, 0.125 mmol), EXAMPLE 1J (0.045 g, 0.133 mmol), cesium fluoride (0.057 g, 0.374 mmol), 1,2-dimethoxyethane (1 mL) and methanol (0.5 mL). The mixture was treated with tetrakis(triphenylphosphine)palladium (0) (7.2 mg, 6.24 µmol) and the vessel was sealed under nitrogen. The reaction was heated at 155° C. for 35 minutes on a Biotage Initiator microwave reactor. The reaction mixture was cooled to ambient temperature, treated with 0.187 mL 2N NaOH, and stirred for 15 hours. The reaction was concentrated and purified by reverse-phase HPLC on a Phenomenex C18 column (3×15 cm) using a gradient of acetonitrile in 0.15% aqueous trifluoroacetic acid to provide the title compound as a trifluoroacetic acid salt. MS (ESI+) m/e 597.2 (M+H)+, $^1$H NMR (300 MHz, methanol-$d_4$) δ ppm 3.83 (s, 3 H) 3.98 (s, 2 H) 4.55 (s, 2 H) 6.31 (m, 1 H) 6.50 (m, 2 H) 7.27 (m, 2 H) 7.41 (m, 5 H) 7.74-7.90 (m, 5 H) 8.00 (m, 1 H) 9.79 (brs, 1 H).

Example 50

2-[[3-({4-[2-(2-benzyl-1H-benzimidazol-6-yl)imidazo[1,2-a]pyridin-3-yl]pyrimidin-2-yl}amino)-4-methoxybenzyl](methyl)amino]ethanol

Example 50A 2-((4-methoxy-3-nitrobenzyl)(methyl)amino)ethanol

A 5 mL round bottom flask was charged with 4-(bromomethyl)-1-methoxy-2-nitrobenzene (0.6 g, 2.44 mmol) and acetonitrile (2 mL). The solution was treated with triethylamine (1 mL, 7.32 mmol) and 2-(methylamino)ethanol (0.585 mL, 7.32 mmol), and the reaction was stirred at ambient temperature for 16 hours. The reaction was partitioned between ethyl acetate and saturated aqueous sodium bicarbonate. The organic layer was washed with brine, dried over $Na_2SO_4$, filtered, and concentrated to provide the title compound. MS (DCI+) m/e 241.1 (M+H)+.

Example 50B 2-((3-amino-4-methoxybenzyl)(methyl)amino)ethanol

To a 25 mL round bottom flask was charged EXAMPLE 50A (380 mg, 1.58 mmol) and ethanol (8 mL). The suspension was treated with iron (0.707 g, 12.65 mmol) followed by a solution of ammonium chloride (169 mg, 3.16 mmol) in water (1.3 mL). The mixture was heated at 90° C. with vigorous stirring for 2 hours. The reaction was cooled to ambient temperature and filtered. The filter pad was washed with methanol and then CH₂Cl₂. The combined filtrates were washed with saturated aqueous sodium bicarbonate (30 mL). The aqueous layer was back-extracted with 2×60 mL 10% methanol/CH₂Cl₂. The combined organic layers were dried over Na₂SO₄, filtered, and concentrated to provide the title compound. MS (DCI⁺) m/e 211.1 (M+H)⁺

Example 50C 2-((3-(4-(2-chloroimidazo[1,2-a]pyridin-3-yl)pyrimidin-2-ylamino)-4-methoxybenzyl)(methyl)amino)ethanol A 5 mL reaction vial equipped with a stir bar was charged with EXAMPLE 2C (0.13 g, 0.49 mmol), EXAMPLE 50B (0.113 g, 0.539 mmol), 2-propanol (2.6 ml) and 4 M HCl in 1,4-dioxane (0.150 mL, 0.6 mmol). The vessel was sealed and the reaction was heated on a thermal block at 120° C. for 20 hours. The reaction was cooled to ambient temperature, diluted with 90 mL 10% methanol/CH₂Cl₂, washed with saturated aqueous sodium bicarbonate and brine, dried over Na₂SO₄, and concentrated. The concentrate was purified by flash chromatography on a 2 g silica gel column eluting with a gradient of from 0% to 4% methanol/CH₂Cl₂ to provide the title compound. (ESI⁺) m/e 439.0 (M+H)⁺

Example 50D

2-[[3-({4-[2-(2-benzyl-1H-benzimidazol-6-yl)imidazo[1,2-a]pyridin-3-yl]pyrimidin-2-yl}amino)-4-methoxybenzyl](methyl)amino]ethanol The trifluoroacetic acid salt of the title compound was prepared as described in EXAMPLE 27C, substituting EXAMPLE 50C for EXAMPLE 27B and EXAMPLE 1J for EXAMPLE 27A. MS (APCI(+)) m/e 611.5 (M+H)⁺, ¹H NMR (300 MHz, methanol-d₄) δ ppm 2.81 (s, 3 H) 3.82 (t, 2 H) 4.00 (s, 3 H) 4.28 (m, 2 H) 4.52 (s, 2 H) 4.82 (s, 2 H) 6.62 (d, 1 H) 7.18-7.29 (m, 3 H) 7.35-7.49 (m, 5 H) 7.66-7.83 (m, 4 H) 7.98 (m, 1 H) 8.27 (d, 1 H) 8.34 (d, 1 H) 9.58 (d, 1 H).

Example 51

N¹-[3-({4-[2-(2-benzyl-1H-benzimidazol-6-yl)imidazo[1,2-a]pyridin-3-yl]pyrimidin-2-yl}amino)phenyl]-N²,N²-dimethylglycinamide

Example 51A tert-butyl 3-(2-(dimethylamino)acetamido)phenylcarbamate

A 250 mL round bottom flask with stir bar was charged with tert-butyl 3-aminophenylcarbamate (5.315 g, 25.5 mmol), 2-(dimethylamino)acetic acid (2.94 g, 28.5 mmol), 1-ethyl-3-[3-(dimethylamino)propyl]-carbodiimide hydrochloride (5.17 g, 27.0 mmol) and 4-dimethylaminopyridine (0.09 g, 0.737 mmol) in dichloromethane (100 ml). The solution was stirred at ambient temperature for 2 hours. The reaction mixture was washed into a separatory funnel with an additional 100 mL dichloromethane and washed with 100 mL saturated sodium bicarbonate. The organics were dried over magnesium sulfate, filtered, and concentrated to provide the title compound. MS ESI⁺) m/e 294.0 (M+H)⁺.

Example 51B

N-(3-aminophenyl)-2-(dimethylamino)acetamide

A 500 mL round bottom flask with stir bar containing EXAMPLE 51A (7.04 g, 24.00 mmol) dissolved in dichloromethane (160 ml) was cooled in an ice bath. Trifluoroacetic acid (40 ml, 519 mmol) was added. After 5 minutes, the ice bath was removed and the solution allowed to warm to ambient temperature. After 1 hour, the mixture was stripped down by rotary evaporation to minimize excess trifluoroacetic acid, then shaken in a separatory funnel with 200 mL each dichloromethane and aqueous sodium carbonate. The organic layer was dried over sodium sulfate, filtered, and concentrated to provide the title compound. MS DCI⁺) m/e 194.1 (M+H)⁺.

Example 51C

N-(3-(4-(2-chloroimidazo[1,2-a]pyridin-3-yl)pyrimidin-2-ylamino)phenyl)-2-(dimethylamino)acetamide The title compound was prepared as described in EXAMPLE 2F, substituting EXAMPLE 51B for EXAMPLE 2E. MS ESI⁺) m/e 422.0 (M+H)⁺.

Example 51D

N¹-[3-({4-[2-(2-benzyl-1H-benzimidazol-6-yl)imidazo[1,2-a]pyridin-3-yl]pyrimidin-2-yl}amino)phenyl]-N²,N²-dimethylglycinamide The title compound was prepared as described in EXAMPLE 1K, substituting EXAMPLE 51C for EXAMPLE 1G. MS ESI⁺) m/e 594.3 (M+H)⁺; ¹H NMR (300 MHz, dimethylsulfoxide-d₆) δ ppm 9.73 (s, 1H), 9.69 (m, 1H), 9.60 (s, 1H), 8.25 (m, 1H), 8.05 (m, 1H), 7.75 (d, 2H), 7.66-7.18 (m, 9H), 7.05 (m, 1H), 6.54 (m, 1H), 4.21 (s, 2H), 3.05 (s, 2H), 2.27 (s, 6H).

Example 52

N-{4-[4-(dimethylamino)piperidin-1-yl]-2-methoxyphenyl}-4-(6-{2-[2-(trifluoromethyl)benzyl]-1H-benzimidazol-6-yl}imidazo[2,1-b][1,3]thiazol-5-yl)pyrimidin-2-amine The trifluoroacetic acid salt of the title compound was prepared according to the procedure of EXAMPLE 1K, substituting EXAMPLE 30F for EXAMPLE 1G and EXAMPLE 42B for EXAMPLE 1J. MS: (ESI⁺) m/e 722.3 (M+H)⁺; ¹H NMR (500 MHz, DMSO-d₆) δ ppm 9.79 (s, 1 H), 8.90 (bs, 1H), 8.55 (bs, 1H), 8.06 (d, 1H), 7.88 (s, 1H), 7.85 (d, 1H), 7.78 (d, 1H), 7.75 (d, 1H), 7.60-7.55 (m, 3H), 7.41 (m, 2H), 6.74 (s, 1H), 6.59 (d, 1H), 6.42 (d, 1H), 4.67 (s, 2 H), 3.97 (d, 2H), 3.88 (s, 3H), 3.33 (m, 1H), 2.80 (s, 6H), 2.72 (t, 2H), 2.11(m, 2H), 1.75-1.72 (m, 2H).

Example 53

$N^1$-[3-({4-[2-(2-benzyl-1H-benzimidazol-6-yl)imidazo[1,2-a]pyridin-3-yl]pyrimidin-2-yl}amino)-4-methoxyphenyl]-$N^2$,$N^2$-dimethylglycinamide

Example 53A 2-(dimethylamino)-N-(4-methoxy-3-nitrophenyl)acetamide

The title compound was prepared as described in EXAMPLE 51A, substituting 4-methoxy-3-nitroaniline for tert-butyl 4-aminophenylcarbamate. MS DCI$^+$) m/e 254.1 (M+H)$^+$.

Example 53B

N-(3-amino-4-methoxyphenyl)-2-(dimethylamino)acetamide

EXAMPLE 53A (7.23 g, 28.5 mmol) and 5% Pd on charcoal (1.446 g, 13.59 mmol) in methanol (200 mL) were stirred at ambient temperature for 2 hours under 30 psi of hydrogen gas, then filtered, concentrated and vacuum dried to give the title compound. MS DCI$^+$) m/e 224.1 (M+H)$^+$.

Example 53C

N-(3-(4-(2-chloroimidazo[1,2-a]pyridin-3-yl)pyrimidin-2-ylamino)-4-methoxyphenyl)-2-(dimethylamino)acetamide The title compound was prepared as described in EXAMPLE 2F, substituting EXAMPLE 53B for EXAMPLE 2E. MS ESI$^+$) m/e 452.1 (M+H)$^+$.

Example 53D $N^1$-[3-({4-[2-(2-benzyl-1H-benzimidazol-6-yl)imidazo[1,2-a]pyridin-3-yl]pyrimidin-2-yl}amino)-4-methoxyphenyl]-$N^2$,$N^2$-dimethylglycinamide The title compound was prepared as described in EXAMPLE 1K, substituting EXAMPLE 53C for EXAMPLE 1G. MS ESI$^+$) m/e 624.2 (M+H)$^+$; $^1$H NMR (300 MHz, dimethylsulfoxide-$d_6$) δ ppm 9.54 (s, 1H), 9.50 (m, 1H), 8.55 (s, 1H), 8.19 (d, 1H), 8.10 (m, 1H), 7.71 (d, 2H), 7.46 (m, 2H), 7.39-7.31 (m, 5H), 7.05 (d, 1H), 6.96 (m, 1H), 6.48 (d, 1H), 4.20 (s, 2H), 3.83 (s, 3H), 3.01 (s, 2H), 2.24 (s, 6H).

Example 54

4-{6-[2-(2-chlorobenzyl)-1H-benzimidazol-6-yl]imidazo[2,1-b][1,3]thiazol-5-yl}-N-{4-[4-(dimethylamino)piperidin-1-yl]-2-methoxyphenyl}pyrimidin-2-amine The trifluoroacetic acid salt of the title compound was prepared according to the procedure of EXAMPLE 1K, substituting EXAMPLE 30F for EXAMPLE 1G and EXAMPLE 9A for EXAMPLE 1J. MS: (ESI$^+$) m/e 690.2 (M+H)$^+$; $^1$H NMR (500 MHz, DMSO-$d_6$) δ ppm 9.79 (s, 1H), 8.90 (bs, 1H), 8.55 (bs, 1H), 8.06 (d, 1H), 7.88 (s, 1H), 7.85 (d, 1H), 7.78 (d, 1H), 7.75 (d, 1H), 7.60-7.55 (m, 3H), 7.41 (m, 2H), 6.74 (s, 1H), 6.59 (d, 1H), 6.42 (d, 1H), 4.63 (s, 2H), 3.97-3.90 (m, 2H), 3.80 (s, 3H), 3.33 (m, 1H), 2.80 (s, 6H), 2.74 (t, 2H), 2.11 (m, 2H), 1.75-1.72 (m, 2H).

Example 55

N-{4-[4-(dimethylamino)piperidin-1-yl]-2-methoxyphenyl}-4-{6-[2-(2-methoxybenzyl)-1H-benzimidazol-6-yl]imidazo[2,1-b][1,3]thiazol-5-yl}pyrimidin-2-amine The trifluoroacetic acid salt of the title compound was prepared according to the procedure of EXAMPLE 1K, substituting EXAMPLE 30F for EXAMPLE 1G and EXAMPLE 3B for EXAMPLE 1J. MS: (ESI$^+$) m/e 686.3 (M+H)$^+$; $^1$H NMR (500 MHz, DMSO-$d_6$) δ ppm 9.92 (s, 1H), 8.88 (bs, 1H), 8.56 (bs, 1H), 8.08 (d, 1H), 7.92 (s, 1H), 7.83 (d, 1H), 7.72 (d, 1H), 7.45-7.38 (m, 4H), 7.10 (d, 1H), 7.03 (t, 1H), 6.73 (s, 1H), 6.57 (d, 1H), 6.40 (d, 1H), 4.47 (s, 2H), 3.97-3.90 (m, 2H), 3.86 (s, 3H), 3.80 (s, 3H), 3.33 (m, 1H), 2.81 (s, 6H), 2.74 (t, 2H), 2.10 (m, 2H), 1.75-1.72 (m, 2H).

Example 56

N-{4-[4-(dimethylamino)piperidin-1-yl]-2-methoxyphenyl}-4-{6-[2-(2-methylbenzyl)-1H-benzimidazol-6-yl]imidazo[2,1-b][1,3]thiazol-5-yl}pyrimidin-2-amine

Example 56A 2-(2-methylbenzyl)-6-(4,4,5,5-tetramethyl-1,3,2-dioxaborolan-2-yl)-1H-benzo[d]imidazole The title compound was prepared according to the procedure of EXAMPLE 1J, substituting 2-methylphenyl acetic acid for phenyl acetic acid. MS: (ESI$^+$) m/e 349.3 (M+H)$^+$

Example 56B

N-{4-[4-(dimethylamino)piperidin-1-yl]-2-methoxyphenyl}-4-{6-[2-(2-methylbenzyl)-1H-benzimidazol-6-yl]imidazo[2,1-b][1,3]thiazol-5-yl}pyrimidin-2-amine, TFA salt The trifluoroacetic acid salt of the title compound was prepared according to the procedure of EXAMPLE 1K, substituting EXAMPLE 30F for EXAMPLE 1G and EXAMPLE 56A for EXAMPLE 1J. MS: (ESI$^+$) m/e 670.3 (M+H)$^+$; $^1$H NMR (500 MHz, DMSO-$d_6$) δ ppm 9.92 (s, 1H), 8.88 (bs, 1H), 8.56 (bs, 1H), 8.08 (d, 1H), 7.92 (s, 1H), 7.83 (d, 1H), 7.72 (d, 1H), 7.45-7.38 (m, 4H), 7.10 (d, 1H), 7.03 (t, 1H), 6.73 (s, 1H), 6.57 (d, 1H), 6.40 (d, 1H), 4.52 (s, 2 H), 3.97-3.90 (m, 2H), 3.80 (s, 3H), 3.33 (m, 1H), 2.81 (s, 6H), 2.74 (t, 2H), 2.33 (s, 3H), 2.10-2.08 (m, 2H), 1.75-1.72 (m, 2H).

Example 57

4-[6-(2-benzyl-1H-benzimidazol-6-yl)imidazo[2,1-b][1,3]thiazol-5-yl]-N-{4-[(dimethylamino)methyl]phenyl}pyrimidin-2-amine The trifluoroacetic acid salt of the title compound was prepared according to the procedure of EXAMPLE 1K, substituting EXAMPLE 46A for EXAMPLE 1G. MS: (ESI$^+$) m/e 557.2 (M+H)$^+$; $^1$H NMR (500 MHz, DMSO-$d_6$) δ ppm 9.93 (s, 1 H), 9.70 (bs, 1H), 8.88 (s, 1H), 8.26 (d, 1H), 7.95 (s, 1H), 7.83 (d, 2H), 7.82 (d, 1H), 7.70 (d, 1H), 7.54 (d, 1H), 7.47-7.40 (m, 7H), 7.35 (t, 1H), 6.55 (d, 1H), 4.52 (s, 2 H), 4.22 (s, 2H), 2.73 (s, 6H).

Example 58

4-[6-(2-benzyl-1H-benzimidazol-6-yl)imidazo[2,1-b][1,3]thiazol-5-yl]-N-{2-[(dimethylamino)methyl]phenyl}pyrimidin-2-amine Example 58A 4-(6-chloroimidazo[2,1-b]thiazol-5-yl)-N-(2-((dimethylamino)methyl)phenyl)pyrimidin-2-amine The title compound was prepared according to the procedure of EXAMPLE 2F, substituting EXAMPLE 30C for EXAMPLE 2C and 2-(dimethylamino)methyl aniline for EXAMPLE 2E. (ESI$^+$) m/e 384.9 (M+H)$^+$.

Example 58B

4-[6-(2-benzyl-1H-benzimidazol-6-yl)imidazo[2,1-b][1,3]thiazol-5-yl]-N-{2-[(dimethylamino)methyl]phenyl}pyrimidin-2-amine The trifluoroacetic acid salt of the title compound was prepared according to the procedure of EXAMPLE 1K, substituting EXAMPLE 58A for EXAMPLE 1G. MS: (ESI$^+$) m/e 557.2 (M+H)$^+$; $^1$H NMR (500 MHz, DMSO-d$_6$) δ ppm 9.59 (bs, 1H), 9.32 (s, 1H), 8.36 (bs, 1H), 8.14 (d, 1H), 7.91 (s, 1H), 7.81 (d, 1H), 7.65-7.61 (m, 2H), 7.57 (d, 1H), 7.46-7.33 (m, 8H), 6.49 (d, 1H), 4.50 (s, 2H), 4.36 (s, 2H), 2.73 (s, 6H).

Example 59

1-{3-[(4-{3-[2-(2-chlorobenzyl)-1H-benzimidazol-5-yl]-1H-pyrazol-4-yl}pyrimidin-2-yl)amino]phenyl}pyrrolidin-2-one Example 59A ethyl 3-iodo-1H-pyrazole-4-carboxylate A mixture of ethyl 3-amino-pyrazole-4-carboxylate (6.4 g, 40 mmole) and diiodomethane (200 g) was cooled to −10° C. Isoamyl nitrite (24 mL, 180 mmole) was added via a syringe over 30 minutes. The mixture was allowed to warm up to ambient temperature and then stirred at 100° C. for 2 hours. After cooling to room temperature, the mixture was concentrated and the residue was dissolved in ethyl acetate (200 mL) and washed with 0.5 M aqueous sodium metasulfite solution (2×70 mL), 1 N HCl and brine. The organic solution was dried with magnesium sulfate and concentrated. The crude product was purified on a silica gel column eluting with 15% ethyl acetate in hexane to provide the title compound. MS (DCI) m/e 266.9 (M+H)$^+$, 283.9 (M+NH$_4$)$^+$.

Example 59B ethyl 3-iodo-1-((2-(trimethylsilyl)ethoxy)methyl)-1H-pyrazole-4-carboxylate To a solution of EXAMPLE 59A (1.3 g, 5 mmole) and diisopropyl-ethyl amine (1.3 mL, 7.5 mmole) in dichloromethane (20 mL) at ambient temperature was added 2-(trimethylsilyl)ethoxymethyl chloride (1.25 g, 7.5 mmole) dropwise. The solution was stirred overnight. Brine (20 mL) was added and the mixture was extracted with ethyl acetate. The mixture was dried with magnesium sulfate, filtered and concentrated. The residue was purified on a silica gel column eluting with 25% ethyl acetate in hexane. The two regioisomers were isolated as a mixture. MS (DCI) m/e 397 (M+H)$^+$.

Example 59C 1-(3-iodo-14(2-(trimethylsilyl)ethoxy)methyl)-1H-pyrazol-4-yl)ethanone A solution of the EXAMPLE 59B (1.28 g, 3.23 mmole, mixture of two regioisomers) and anhydrous pyridine (30 μL) in anhydrous tetrahydrofuran (4 mL) and toluene (12 mL) was cooled to −45° C. using an acetonitrile and dry ice bath. Tebbe's reagent ((C$_5$H$_5$)$_2$TiCH$_2$ClAl(CH$_3$)$_2$) (0.5 M in toluene, 7.75 mL, 3.38 mmole) was added dropwise over 10 minutes. The mixture was stirred at −45° C. for 1 hour, then allowed to warm up to room temperature and stirred for another hour. The mixture was cooled with an ice-bath and methanol (10 mL) was carefully added, followed by 20 mL of 3 M aqueous HCl. The mixture was stirred for 30 minutes and extracted with dichloromethane. The solution was dried with magnesium sulfate, filtered and concentrated. The residue was purified on a silica gel column eluting with 25% ethyl acetate in hexane to give the title compound. MS (DCI) m/e 367 (M+H)$^+$, 384 (M+NH$_4$)$^+$.

Example 59D (E)-3-(dimethylamino)-1-(3-iodo-1-((2-(trimethylsilyl)ethoxy)methyl)-1H-pyrazol-4-yl)prop-2-en-1-one A solution of EXAMPLE 59C in N,N-dimethylformamide di-tert-butyl acetal (8 mL) was stirred at 90° C. for 4 hours. The mixture was concentrated and the residue purified on a silica gel column eluting with 30% ethyl acetate first, than 100% ethyl acetate to provide the title compound. MS (DCI) m/e 422 (M+H)$^+$.

Example 59E 1-(3-(4-(3-iodo-1-((2-(trimethylsilyl)ethoxy)methyl)-1H-pyrazol-4-yl)pyrimidin-2-ylamino)phenyl)pyrrolidin-2-one The title compound was prepared according to the procedure of EXAMPLE 1G, substituting EXAMPLE 59D for EXAMPLE 1D. MS: (ESI$^+$) m/e 399.0 (M+H)$^+$.

Example 59F

1-{3-[(4-{3-[2-(2-chlorobenzyl)-1H-benzimidazol-5-yl]-1H-pyrazol-4-yl}pyrimidin-2-yl)amino]phenyl}pyrrolidin-2-one, TFA salt A Personal Chemistry microwave reaction tube was charged with EXAMPLE 59E (55 mg, 0.095 mmole), EXAMPLE 9A (42 m, 0.11 mmole), cesium fluoride (44 mg, 0.29 mmole) and 2 mL of dimethoxyethane/methanol (3:2) mixture. The mixture was purged with argon and palladium tetrakis(triphenylphosphine) (12 mg, 0.01 mmole) was added. The sealed tube was stirred at 150° C. for 20 minutes on a Personal Chemistry microwave instrument. The mixture was quenched with brine (10 mL) and extracted with dichloromethane (3×10 mL). The combined organic solution was dried with magnesium sulfate, filtered and concentrated. The residue was purified on a silica gel eluting with 5% methanol in CH$_2$Cl$_2$. The crude material was dissolved in methanol (3 mL) and 4 N HCl in dioxane (1 mL) and stirred at room temperature overnight. The mixture was concentrated and the residue was purified on a reverse phase HPLC using TFA buffered water-acetonitrile as the mobile phase to provide the trifluoroacetic acid salt of the title compound. MS: (ESI$^+$) m/e 561.2 (M+H)$^+$; $^1$H NMR (500 MHz, DMSO-d$_6$) δ ppm 9.47 (s, 1H), 8.39 (bs, 1H), 8.34 (d, 1H), 7.84-7.83 (m, 2H), 7.70 (d, 1H), 7.62 (d, 1H), 7.58-7.53 (m, 2H), 7.45-7.43 (m, 2H), 7.14-7.13 (m, 2H), 7.80-6.79 (m, 2H), 4.63 (s, 2H), 3.68 (t, 2H), 3.01 (t, 2H), 2.05 (m, 2H).

Example 60

N-{3-[(dimethylamino)methyl]phenyl}-4-{1-ethyl-3-[2-(2-methoxybenzyl)-1H-benzimidazol-5-yl]-1H-pyrazol-4-yl}pyrimidin-2-amine Example 60A Ethyl 1-ethyl-3-iodo-1H-pyrazole-4-carboxylate A 500 mL flask was charged with the sodium hydride (0.584 g, 14.61 mmol) and tetrahydrofuran (100 mL). To the resulting suspension was added a solution of EXAMPLE 59A (3.11 g, 11.69 mmol) in tetrahydrofuran (50 mL) dropwise over about 20 minutes and the reaction was stirred for 4 hours under nitrogen. The reaction mixture was cooled to −45° C. and a solution of iodoethane (3.77 mL, 46.8 mmol) in tetrahydrofuran (20 ml) was added dropwise over 20 minutes. The reaction mixture was allowed to come to ambient temperature and stirring was continued for 42 hours. The reaction was diluted with brine (400 mL) and extracted with ether (400 ml, 2×200 mL). The combined organics were dried over sodium sulfate, filtered and concentrated. The crude material was purified on the ISCO chromatography system on a silica gel cartridge (150 g) eluting with a 0, 10, 25, and 50% ethyl acetate/hexane step gradient to give the title compound. MS DCI$^+$) m/e 295 (M+H)$^+$.

Example 60B 1-(1-Ethyl-3-iodo-1H-pyrazol-4-yl)ethanone

The title compound was prepared as described in EXAMPLE 59C, substituting EXAMPLE 60A for EXAMPLE 59B. MS DCI$^+$) m/e 265 (M+H)$^+$.

Example 60C (E)-3-(dimethylamino)-1-(1-ethyl-3-iodo-1H-pyrazol-4-yl)prop-2-en-1-one The title compound was prepared as described in EXAMPLE 59D, substituting EXAMPLE 60B for EXAMPLE 59C. MS DCI$^+$) m/e 320 (M+H)$^+$.

Example 60D (E)-tert-butyl (tert-butoxycarbonylamino)(3-((dimethylamino)methyl)phenylamino)methylenecarbamate The title compound was prepared as described EXAMPLE 1E, substituting 3-((dimethylamino)-methyl)aniline for (3-aminophenyl)pyrrolidin-2-one. MS DCI$^+$) m/e 393 (M+H)$^+$.

Example 60E 1-(3-((Dimethylamino)methyl)phenyl)guanidine

The title compound was prepared as described in EXAMPLE 1F, substituting EXAMPLE 60D for EXAMPLE 1E. MS DCI$^+$) m/e 193 (M+H)$^+$.

Example 60F

N-(3-((dimethylamino)methyl)phenyl)-4-(1-ethyl-3-iodo-1H-pyrazol-4-yl)pyrimidin-2-amine The title compound was prepared as described in EXAMPLE 1G, substituting EXAMPLE 60C for EXAMPLE 1D and EXAMPLE 60E for EXAMPLE 1F. MS: (ESI$^+$) m/e 399.0 (M+H)$^+$.

Example 60G

N-{3-[(dimethylamino)methyl]phenyl}-4-{1-ethyl-3-[2-(2-methoxybenzyl)-1H-benzimidazol-5-yl]-1H-pyrazol-4-yl}pyrimidin-2-amine A 5 mL microwave vial was charged with EXAMPLE 60F (75 mg, 0.167 mmol), EXAMPLE 3B (91 mg, 0.251 mmol), cesium fluoride (76 mg, 0.502 mmol) and palladium tetrakis (19.33 mg, 0.017 mmol). Under argon, dimethoxyethane (3 mL) and methanol (1.5 mL) were added. The vial was sealed and heated in a Biotage Initiator 2 microwave reactor at 160° C. for 15 minutes. Additional palladium tetrakis (19.33 mg, 0.017 mmol) was added and the vial was purged with argon, sealed and microwave heated at 160° C. for 15 minutes. Additional palladium tetrakis (19.33 mg, 0.017 mmol) added and the vial was purged with argon, sealed and microwave heated at 160° C. for 15 minutes. The reaction mixture was filtered to remove the black solid and the filtrate was concentrated. The residue was purified on a silica gel syringe cartridge (20 g) eluted with 5% 7-N methanolic ammonia in methylene chloride to give the title compound. MS (ESI$^+$) m/e 559 (M+H)$^+$, (ESI(−)) m/e 557 (M−H)$^-$; $^1$H NMR (300 MHz, DMSO-d$_6$) δ ppm 12.11 (d, 1 H), 9.40 (s, 1 H), 8.30 (s, 1 H), 8.24 (t, 1 H), 7.70 (s, 1 H), 7.36-7.62 (m, 3 H), 7.21-7.31 (m, 2 H), 7.16 (d, 1 H), 6.83-7.07 (m, 3 H), 6.76 (d, 1 H), 6.54 (dd, 1 H), 4.24 (q, 2 H), 4.14 (s, 2 H), 3.79 (d, 3 H), 3.21-3.28 (m, 2 H), 2.13 (s, 6 H), 1.48 (t, 3 H).

Example 61

4-{3-[2-(2-chlorobenzyl)-1H-benzimidazol-5-yl]-1-ethyl-1H-pyrazol-4-yl}-N-{3-[(dimethylamino)methyl]phenyl}pyrimidin-2-amine The title compound was prepared as described in EXAMPLE 60G, substituting EXAMPLE 9A for EXAMPLE 3B. MS (ESI$^+$) m/e 563 (M+H)$^+$, (ESI(−)) m/e 561 (M−H)$^-$; $^1$H NMR (300 MHz, DMSO-d$_6$) δ ppm 12.32 (d, 1 H), 9.40 (d, 1 H), 8.30 (s, 1 H), 8.25 (t, 1 H), 7.69 (s, 1 H), 7.23-7.63 (m, 8 H), 6.93 (t, 1 H), 6.75 (d, 1 H), 6.56 (dd, 1 H), 4.32 (s, 2 H), 4.25 (q, 2 H), 3.25 (d, 2 H), 2.13 (s, 6 H), 1.48 (t, 3 H).

Example 62

5-{4-[2-({3-[(dimethylamino)methyl]phenyl}amino)pyrimidin-4-yl]-1-ethyl-1H-pyrazol-3-yl}-N-phenyl-1H-benzimidazol-2-amine

Example 62A

N-phenyl-6-(4,4,5,5-tetramethyl-1,3,2-dioxaborolan-2-yl)-1H-benzo[d]imidazol-2-amine Into a 100 mL round-bottomed flask was charged EXAMPLE 1I (0.258 g, 1.102 mmol) in tetrahydrofuran (11.02 mL). Phenyl isothiocyanate (0.138 mL, 1.157 mmol) and 1-ethyl-3-[3-(dimethylamino)propyl]-carbodiimide hydrochloride (0.380 g, 1.984 mmol) were added. The mixture was heated to 50° C. overnight, then cooled to room temperature. The mixture was diluted with water, and extracted with ethyl acetate. The organic layer was washed with brine, dried over MgSO$_4$, filtered and concentrated to provide the title compound. MS (ESI$^+$) m/e 336 (M+H)$^+$.

Example 62B

5-{4-[2-({3-[(dimethylamino)methyl]phenyl}amino)pyrimidin-4-yl]-1-ethyl-1H-pyrazol-3-yl}-N-phenyl-1H-benzimidazol-2-amine The title compound was prepared as described in EXAMPLE 60G, substituting EXAMPLE 62A for EXAMPLE 3B. MS (ESI$^+$) m/e 530 (M+H)$^+$, (ESI(−)) m/e 528 (M−H)$^-$; $^1$H NMR (500 MHz, DMSO-d$_6$) δ ppm 11.03 (d, 1 H), 9.52 (s, 1 H), 9.32-9.47 (m, 1 H), 8.29 (s, 1 H), 8.25 (s, 1 H), 7.70-7.81 (m, 3 H), 7.46 (d, 1 H), 7.42 (s, 1 H), 7.26-7.37 (m, 3 H), 7.13 (d, 1 H), 7.04 (t, 1 H), 6.93 (t, 1 H), 6.79 (d, 1 H), 6.58 (s, 1 H), 4.25 (q, 2 H), 3.27 (s, 2 H), 2.14 (s, 6 H), 1.48 (t, 3 H).

Example 63

4-[3-(2-benzyl-1H-benzimidazol-5-yl)-1-ethyl-1H-pyrazol-4-yl]-N-{3-[(dimethylamino)methyl]phenyl}pyrimidin-2-amine The title compound was prepared as described in EXAMPLE 60G, substituting EXAMPLE 1J for EXAMPLE 3B. MS (ESI$^+$) m/e 529 (M+H)$^+$, (ESI(−)) m/e 527 (M−H)$^-$; $^1$H NMR (300 MHz, DMSO-d$_6$) δ ppm 12.28 (s, 1 H), 9.38 (s, 1 H), 8.30 (s, 1 H), 8.24 (d, 1 H), 7.69 (s, 1 H), 7.19-7.65 (m, 9 H), 6.92 (t, 1 H), 6.74 (d, 1 H), 6.54 (d, 1 H), 4.24 (q, 2 H), 4.18 (s, 2 H), 3.25 (s, 2 H), 2.13 (s, 6 H), 1.48 (t, 3 H).

Example 64

4-[3-(2-benzyl-1H-benzimidazol-5-yl)-1-ethyl-1H-pyrazol-4-yl]-N-(2-methoxyphenyl)pyrimidin-2-amine

Example 64A 4-(1-ethyl-3-iodo-1H-pyrazol-4-yl)-N-(2-methoxyphenyl)pyrimidin-2-amine The title compound was prepared as described in EXAMPLE 1G, substituting EXAMPLE 60C for EXAMPLE 1D and 1-(2-methoxyphenyl)guanidine hydrochloride for EXAMPLE 1F. MS: (ESI$^+$) m/e 422 (M+H)$^+$, (ESI(−)) m/e 420 (M−H)$^-$.

Example 64B

4-[3-(2-benzyl-1H-benzimidazol-5-yl)-1-ethyl-1H-pyrazol-4-yl]-N-(2-methoxyphenyl)pyrimidin-2-amine The title compound was prepared as described in EXAMPLE 60G, substituting EXAMPLE 64A for EXAMPLE 60F and EXAMPLE 1J for EXAMPLE 3B. MS (ESI$^+$) m/e 502 (M+H)$^+$, (ESI(−)) m/e 500 (M−H)$^-$; $^1$H NMR (300 MHz, DMSO-d$_6$) δ ppm 12.30 (s, 1 H), 8.38 (s, 1 H), 8.26 (d, 1 H), 7.82 (d, 1 H), 7.74 (s, 1 H), 7.40-7.65 (m, 2 H), 7.19-7.38 (m, 6 H), 6.95 (d, 1 H), 6.80 (t, 1 H), 6.67 (d, 1 H), 6.44 (t, 1 H), 4.24 (q, 2 H), 4.18 (s, 2 H), 3.83 (s, 3 H), 1.47 (t, 3 H).

Example 65

4-{1-ethyl-3-[2-(2-methoxybenzyl)-1H-benzimidazol-5-yl]-1H-pyrazol-4-yl}-N-(2-methoxyphenyl)pyrimidin-2-amine The title compound was prepared as described in EXAMPLE 60G, substituting EXAMPLE 64A for EXAMPLE 60F. MS (ESI$^+$) m/e 532 (M+H)$^+$, (ESI(−)) m/e 530 (M−H)$^-$; $^1$H NMR (300 MHz, DMSO-d$_6$) δ ppm 12.10 (d, 1 H), 8.37 (s, 1 H), 8.24-8.29 (m, 1 H), 7.82-7.90 (m, 1 H), 7.74 (s, 1 H), 7.38-7.62 (m, 2 H), 7.20-7.30 (m, 2 H), 7.15 (dd, 1 H), 6.99 (dd, 2 H), 6.79-6.92 (m, 2 H), 6.66 (t, 1 H), 6.50 (t, 1 H), 4.24 (q, 2 H), 4.14 (s, 2 H), 3.84 (s, 3 H), 3.79 (s, 3 H), 1.47 (t, 3 H).

Example 66

4-[3-(2-benzyl-1H-benzimidazol-5-yl)-1-ethyl-1H-pyrazol-4-yl]-N-{-4-[4-(dimethylamino)piperidin-1-yl]-2-methoxyphenyl}pyrimidin-2-amine

Example 66A 1-(4-(4-(dimethylamino)piperidin-1-yl)-2-methoxyphenyl)guanidine A 250 mL flask was charged with the EXAMPLE 30E (2.0 g, 8.02 mmol), 2,2,10,10-tetramethyl-6-thioxo-3,9-dioxa-5,7-diazaundecane-4,8-dione (2.66 g, 9.62 mmol), PS-carbodiimide (1.42 mmole/g, 8.47 g, 12.03 mmole, 1.5 eq) and dichloromethane (75 mL). The mixture was stirred overnight. The solvent was filtered off and the residue was shaken with methylene chloride (6×100 mL) and filtered. The combined filtrates were concentrated and purified on the ISCO chromatography system using a silica gel cartridge (150 g) eluted with a 1, 2.5, 5, 10% 7N methanolic ammonia in methylene chloride step gradient to afford the Boc-protected product as a white solid. The solid was dissolved in a mixture of anhydrous methylene chloride (30 ml) and trifluoroacetic acid (30 ml) and stirred under nitrogen for 2 hours. The reaction was concentrated at <40° C. to afford the trifluoroacetic acid salt of the title compound. MS DCI$^+$) m/e 292 (M+H)$^+$.

Example 66B

N-(4-(4-(dimethylamino)piperidin-1-yl)-2-methoxyphenyl)-4-(1-ethyl-3-iodo-1H-pyrazol-4-yl)pyrimidin-2-amine The title compound was prepared as described in EXAMPLE 1G, substituting EXAMPLE 60C for EXAMPLE 1D and EXAMPLE 66A for EXAMPLE 1F. MS: (ESI$^+$) m/e 548 (M+H)$^+$, (ESI(−)) m/e 546 (M−H)$^−$.

Example 66C

4-[3-(2-benzyl-1H-benzimidazol-5-yl)-1-ethyl-1H-pyrazol-4-yl]-N-{-4-[4-(dimethylamino)piperidin-1-yl]-2-methoxyphenyl}pyrimidin-2-amine The title compound was prepared as described in EXAMPLE 60G, substituting EXAMPLE 66B for EXAMPLE 60F and EXAMPLE 1J for EXAMPLE 3B. MS (ESI$^+$) m/e 628 (M+H)$^+$, (ESI(−)) m/e 626 (M−H)$^−$; $^1$H NMR (300 1H NMR (300 MHz, DMSO-d$_6$) δ ppm 12.34 (d, 1 H), 8.32 (s, 1 H), 8.17 (dd, 1 H), 7.39-7.64 (m, 3 H), 7.20-7.38 (m, 7 H), 6.51-6.61 (m, 2 H), 6.07 (s, 1 H), 4.15-4.30 (m, 4 H), 3.79 (s, 3 H), 3.57 (d, 2 H), 2.52-2.63 (m, 2 H), 2.09-2.24 (m, 7 H), 1.81 (s, 2 H), 1.38-1.56 (m, 5 H).

Example 67

4-{3-[2-(2-chlorobenzyl)-1H-benzimidazol-5-yl]-1-ethyl-1H-pyrazol-4-yl}-N-{4-[4-(dimethylamino)piperidin-1-yl]-2-methoxyphenyl}pyrimidin-2-amine The title compound was prepared as described in EXAMPLE 60G, substituting EXAMPLE 66B for EXAMPLE 60F and EXAMPLE 9A for EXAMPLE 3B. MS (ESI$^+$) m/e 662 (M+H)$^+$, (ESI(−)) m/e 660 (M−H)$^−$; $^1$H NMR (300 MHz, DMSO-d$_6$) δ ppm 12.33 (s, 1 H), 8.32 (s, 1 H), 8.19 (d, 1 H), 7.40-7.63 (m, 5 H), 7.27-7.40 (m, 3 H), 7.24 (dd, 1 H), 6.57 (d, 2 H), 6.00 (d, 1 H), 4.32 (s, 2 H), 4.23 (q, 2 H), 3.79 (s, 3 H), 3.56 (d, 2 H), 2.52-2.61 (m, 2 H), 2.09-2.24 (m, 7 H), 1.81 (s, 2 H), 1.38-1.56 (m, 5 H).

Example 68

N-{4-[4-(dimethylamino)piperidin-1-yl]-2-methoxyphenyl}-4-{1-ethyl-3-[2-(2-methoxybenzyl)-1H-benzimidazol-5-yl]-1H-pyrazol-4-yl}pyrimidin-2-amine The title compound was prepared as described in EXAMPLE 60G, substituting EXAMPLE 66B for EXAMPLE 60F. MS (ESI$^+$) m/e 658 (M+H)$^+$, (ESI(−)) m/e 656 (M−H)$^−$; $^1$H NMR (300 MHz, DMSO-d$_6$) δ ppm 12.14 (d, 1 H), 8.32 (s, 1 H), 8.18 (d, 1 H), 7.38-7.63 (m, 4 H), 7.18-7.29 (m, 2 H), 7.14 (d, 1 H), 7.01 (d, 1 H), 6.88 (t, 1 H), 6.57 (d, 2 H), 6.03 (d, 1 H), 4.23 (q, 2 H), 4.13 (s, 2 H), 3.79 (s, 6 H), 3.56 (d, 2 H), 2.52-2.62 (m, 2 H), 2.10-2.23 (m, 7 H), 1.83 (d, 2 H), 1.39-1.55 (m, 5 H).

Example 69

N-{4-[4-(dimethylamino)piperidin-1-yl]-2-methoxyphenyl}-4-[1-ethyl-3-(2-phenyl-1H-benzimidazol-5-yl)-1H-pyrazol-4-yl]pyrimidin-2-amine The title compound was prepared as described in EXAMPLE 60G, substituting EXAMPLE 66B for EXAMPLE 60F and EXAMPLE 27A for EXAMPLE 3B. MS (ESI$^+$) m/e 614 (M+H)$^+$, (ESI(−)) m/e 612 (M−H)$^−$; $^1$H NMR (300 MHz, DMSO-d$_6$) δ ppm 12.98 (s, 1 H), 8.38 (s, 1 H), 8.28 (d, 1 H), 8.22 (d, 2 H), 7.41-7.71 (m, 6 H), 7.22 (d, 1 H), 7.08 (s, 1 H), 6.81 (d, 1 H), 6.45 (d, 1 H), 5.39 (s, 1 H), 4.25 (q, 2 H), 3.72-3.80 (m, 3 H), 3.22-3.32 (m, 2 H), 2.21-2.36 (m, 2 H), 2.09 (s, 6 H), 1.87 (s, 1 H), 1.43-1.58 (m, 5 H), 1.23 (s, 2 H).

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:
1. A compound of formula (I)

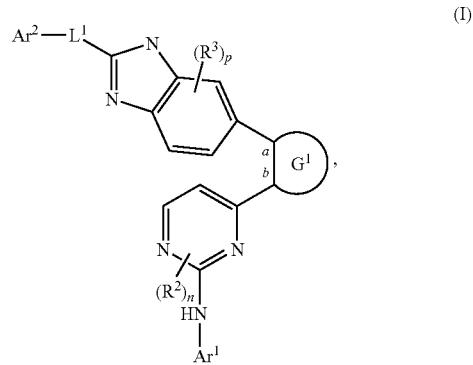

or a pharmaceutically acceptable salt, solvate, prodrug, or a combination thereof, wherein
G$^1$ is formula (i), (ii), (iii), or (iv)

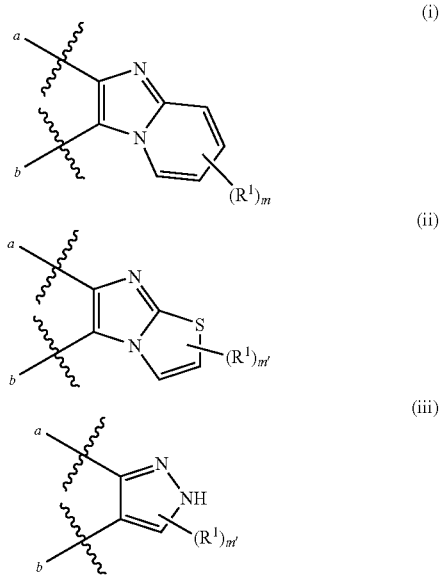

-continued

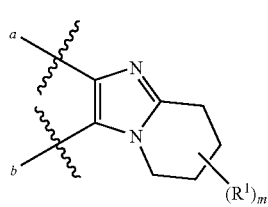
(iv)

m is 0, 1, 2, 3, or 4;
m' is 0, 1, or 2;
n is 0, 1, or 2;
p is 0, 1, 2, or 3;
$R^1$, $R^2$, and $R^3$ are optional substituents, and when present, are each independently alkyl, halogen, —O(alkyl), —O(haloalkyl), or haloalkyl;
a and b designate the points of attachment at which formula (i), (ii), (iii), and (iv) are bound to formula (I);
$L^1$ is a bond, O, N(H), or $(CR^4R^5)_q$;
$R^4$ and $R^5$, at each occurrence, are each independently hydrogen, alkyl, halogen, or haloalkyl;
q is 1, 2, 3, or 4;
$Ar^1$ is aryl or heteroaryl; each of which is independently unsubstituted or substituted with 1, 2, 3, 4, or 5 substituents as represented by T, wherein each T is selected from the group consisting of alkyl, alkenyl, alkynyl, halogen, haloalkyl, oxo, CN, $NO_2$, $G^2$, —$OR^6$, —$OC(O)R^7$, —$SR^6$, —$S(O)R^7$, —$S(O)_2R^7$, —$S(O)_2N(R^8)(R^9)$, —$N(R^8)(R^9)$, —$N(R^8)C(O)R^7$, —$N(R^8)C(O)OR^7$, —$N(R^8)S(O)_2R^7$, —$N(R^8)C(O)N(R^8)(R^9)$, —$N(R^8)C(O)$—$(C_{1-6}$ alkylenyl)-$N(R^8)(R^9)$, —$N(R^8)S(O)_2N(R^8)(R^9)$, —$C(O)R^6$, —$C(O)OR^6$, —$C(O)N(R^8)(R^9)$, —$(C_{1-6}$ alkylenyl)-$G^2$, —$(C_{1-6}$ alkylenyl)-$OR^6$, —$(C_{1-6}$ alkylenyl)-$OC(O)R^7$, —$(C_{1-6}$ alkylenyl)-$SR^6$, —$(C_{1-6}$ alkylenyl)-$S(O)R^7$, —$(C_{1-6}$ alkylenyl)-$S(O)_2R^7$, —$(C_{1-6}$ alkylenyl)-$S(O)_2N(R^8)(R^9)$, —$(C_{1-6}$ alkylenyl)-$N(R^8)(R^9)$, —$(C_{1-6}$ alkylenyl)-$N(R^8)C(O)R^7$, —$(C_{1-6}$ alkylenyl)-$N(R^8)C(O)OR^7$, —$(C_{1-6}$ alkylenyl)-$N(R^8)S(O)_2R^7$, —$(C_{1-6}$ alkylenyl)-$N(R^8)C(O)N(R^8)(R^9)$, —$(C_{1-6}$ alkylenyl)-$N(R^8)S(O)_2N(R^8)(R^9)$, —$(C_{1-6}$ alkylenyl)-$C(O)R^6$, —$(C_{1-6}$ alkylenyl)-$C(O)OR^6$, and —$(C_{1-6}$ alkylenyl)-$C(O)N(R^8)(R^9)$,
two substituents on the vicinal carbon atoms of $Ar^1$, together with the carbon atoms to which they are attached, optionally form a monocyclic 5- or 6-membered heterocycle containing one or two heteroatoms selected from N(H), O, S, S(O), or $S(O)_2$, wherein each of the monocyclic heterocycle is optionally substituted with 1, 2, 3, or 4 alkyl groups;
each occurrence of $R^6$ and $R^9$ are each independently hydrogen, alkyl, haloalkyl, —$(C_{1-6}$ alkylenyl)-CN, —$(C_{1-6}$ alkylenyl)-OH, —$(C_{1-6}$ alkylenyl)-C(O)OH, $G^3$, or —$(C_{1-6}$ alkylenyl)-$G^3$;
each occurrence of $R^7$ is independently alkyl, haloalkyl, —$(C_{1-6}$ alkylenyl)-CN, —$(C_{1-6}$ alkylenyl)-OH, $G^3$, or —$(C_{1-6}$ alkylenyl)-$G^3$;
each occurrence of $R^8$ is independently hydrogen, alkyl, or haloalkyl;
each occurrence of $G^2$ is independently aryl, heteroaryl, heterocycle, cycloalkyl, or cycloalkenyl, each of which is independently unsubstituted or substituted with 1, 2, 3, 4, or 5 substituents selected from the group consisting of $G^3$, —$(C_{1-6}$ alkylenyl)-$G^3$, and $R^{10}$, each occurrence of $G^3$ is independently aryl, heteroaryl, heterocycle, cycloalkyl, or cycloalkenyl, each of which is independently unsubstituted or substituted with 1, 2, 3, 4, or 5 $R^{10}$ groups;
$Ar^2$ is aryl or heteroaryl, each of which is independently unsubstituted or substituted with 1, 2, 3, 4, or 5 $R^{10}$ groups;
each occurrence of $R^{10}$ is independently alkyl, alkenyl, alkynyl, halogen, haloalkyl, oxo, CN, $NO_2$, —$OR^{Z1}$, —$OC(O)R^{Z2}$, —$SR^{Z1}$, —$S(O)R^{Z2}$, —$S(O)_2R^{Z2}$, —$S(O)_2N(R^{Z3})(R^{Z4})$, —$N(R^{Z3})(R^{Z4})$, —$N(R^{Z3})C(O)R^{Z2}$, —$N(R^{Z3})C(O)OR^{Z2}$, —$N(R^{Z3})S(O)_2R^{Z2}$, —$N(R^{Z3})C(O)N(R^{Z3})(R^{Z4})$, —$N(R^{Z3})S(O)_2N(R^{Z3})(R^{Z4})$, —$C(O)R^{Z1}$, —$C(O)OR^{Z1}$, —$C(O)N(R^{Z3})(R^{Z4})$, —$(C_{1-6}$ alkylenyl)-$OR^{Z1}$, —$(C_{1-6}$ alkylenyl)-$OC(O)R^{Z2}$, —$(C_{1-6}$ alkylenyl)-$SR^{Z1}$, —$(C_{1-6}$ alkylenyl)-$S(O)R^{Z2}$, —$(C_{1-6}$ alkylenyl)-$S(O)_2R^{Z2}$, —$(C_{1-6}$ alkylenyl)-$S(O)_2N(R^{Z3})(R^{Z4})$, —$(C_{1-6}$ alkylenyl)-$N(R^{Z3})(R^{Z4})$, —$(C_{1-6}$ alkylenyl)-$N(R^{Z3})C(O)R^{Z2}$, —$(C_{1-6}$ alkylenyl)-$N(R^{Z3})C(O)OR^{Z2}$, —$(C_{1-6}$ alkylenyl)-$N(R^{Z3})S(O)_2R^{Z2}$, —$(C_{1-6}$ alkylenyl)-$N(R^{Z3})C(O)N(R^{Z3})(R^{Z4})$, —$(C_{1-6}$ alkylenyl)-$N(R^{Z3})S(O)_2N(R^{Z3})(R^{Z4})$, —$(C_{1-6}$ alkylenyl)-$C(O)R^{Z1}$, —$(C_{1-6}$ alkylenyl)-$C(O)OR^{Z1}$, or —$(C_{1-6}$ alkylenyl)-$C(O)N(R^{Z3})(R^{Z4})$;
each occurrence of $R^{Z1}$, $R^{Z3}$, and $R^{Z4}$, are each independently hydrogen, alkyl, or haloalkyl; and
each occurrence of $R^{Z2}$ is independently alkyl or haloalkyl.

2. The compound according to claim 1 having formula (I) or a pharmaceutically acceptable salt or solvate thereof, wherein $Ar^2$ is optionally substituted phenyl.

3. The compound according to claim 1 or a pharmaceutically acceptable salt or solvate thereof having formula (I) or a pharmaceutically acceptable salt or solvate thereof, wherein
$Ar^2$ is optionally substituted phenyl; and
$Ar^1$ is phenyl or monocyclic heteroaryl; each of which is optionally substituted.

4. The compound according to claim 1 having formula (I-i) or a pharmaceutically acceptable salt or solvate thereof

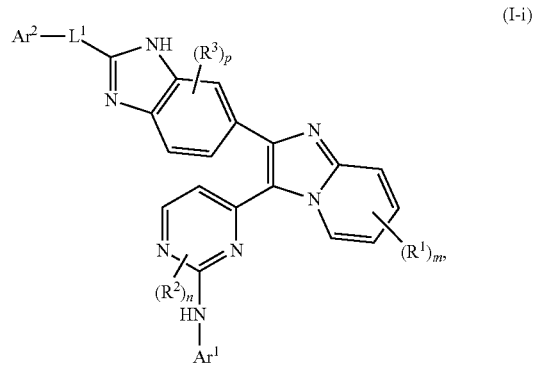
(I-i)

wherein $R^1$, $R^2$, $R^3$, m, n, p, $L^1$, $Ar^1$, and $Ar^2$ are as set forth in claim 1.

5. The compound according to claim 4 having formula (I-i), or a pharmaceutically acceptable salt or solvate thereof, wherein $Ar^2$ is optionally substituted phenyl.

6. The compound according to claim 4 having formula (I-i), or a pharmaceutically acceptable salt or solvate thereof, wherein
$L^1$ is a bond, and
$Ar^2$ is optionally substituted phenyl.

7. The compound according to claim 4 having formula (I-i), or a pharmaceutically acceptable salt or solvate thereof, wherein
L¹ is N(H), and
Ar² is optionally substituted phenyl.

8. The compound according to claim 4 having formula (I-i), or a pharmaceutically acceptable salt or solvate thereof, wherein
L¹ is $(CR^3R^4)_q$, and
Ar² is optionally substituted phenyl.

9. The compound according to claim 1 having formula (I-ii) or a pharmaceutically acceptable salt or solvate thereof

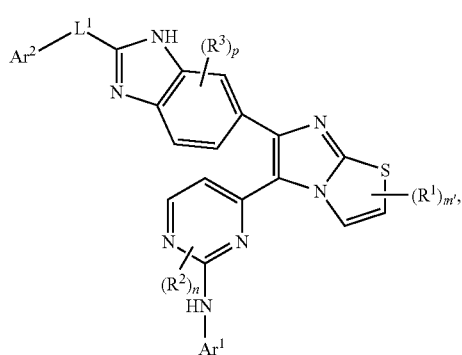

(I-ii)

wherein R¹, R², R³, m', n, p, L¹, Ar¹, and Ar² are as set forth in claim 1.

10. The compound according to claim 9 having formula (I-ii), or a pharmaceutically acceptable salt or solvate thereof, wherein Ar² is optionally substituted phenyl.

11. The compound according to claim 9 having formula (I-ii), or a pharmaceutically acceptable salt or solvate thereof, wherein
L¹ is $(CR^4R^5)_q$; and
Ar² is optionally substituted phenyl.

12. The compound according to claim 1 having formula (I-iii) or a pharmaceutically acceptable salt or solvate thereof

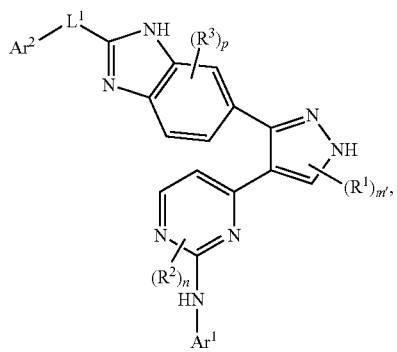

(I-iii)

wherein R¹, R², R³, m', n, p, L¹, Ar¹, and Ar² are as set forth in claim 1.

13. The compound according to claim 12 having formula (I-iii), or a pharmaceutically acceptable salt or solvate thereof, wherein Ar² is optionally substituted phenyl.

14. The compound according to claim 12 having formula (I-iii), or a pharmaceutically acceptable salt or solvate thereof, wherein L¹ is a bond; and
Ar² is optionally substituted phenyl.

15. The compound according to claim 12 having formula (I-iii), or a pharmaceutically acceptable salt or solvate thereof, wherein
L¹ is N(H); and
Ar² is optionally substituted phenyl.

16. The compound according to claim 12 having formula (I-iii), or a pharmaceutically acceptable salt or solvate thereof, wherein
L¹ is $(CR^4R^5)_q$; and
Ar² is optionally substituted phenyl.

17. The compound according to claim 1 having formula (I-iv) or a pharmaceutically acceptable salt or solvate thereof

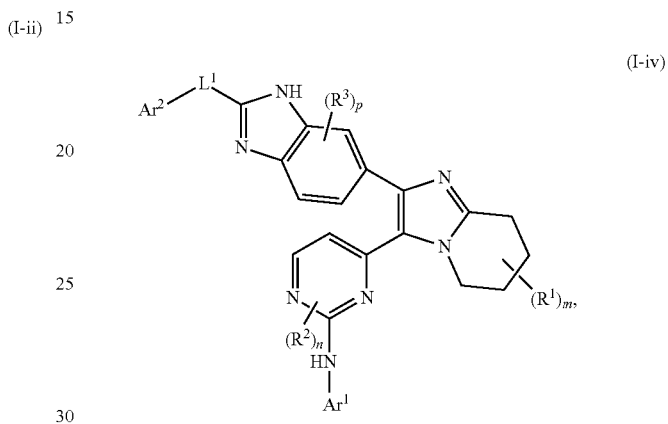

(I-iv)

wherein R¹, R², R³, m, n, p, L¹, Ar¹, and Ar² are as set forth in claim 1.

18. The compound according to claim 17 having formula (I-iv), or a pharmaceutically acceptable salt or solvate thereof, wherein Ar² is optionally substituted phenyl.

19. The compound according to claim 17 having formula (I-iv), or a pharmaceutically acceptable salt or solvate thereof, wherein
L¹ is $(CR^4R^5)_q$, and
Ar² and Ar¹ are optionally substituted phenyl.

20. The compound according to claim 1 or a pharmaceutically acceptable salt or solvate thereof, selected from the group consisting of
1-[3-({4-[2-(2-benzyl-1H-benzimidazol-5-yl)imidazo[1,2-a]pyridin-3-yl]pyrimidin-2-yl}amino)phenyl]pyrrolidin-2-one;
4-[2-(2-benzyl-1H-benzimidazol-6-yl)imidazo[1,2-a]pyridin-3-yl]-N-{3-[2-(dimethylamino)ethyl]phenyl}pyrimidin-2-amine;
N-{3-[2-(dimethylamino)ethyl]phenyl}-4-{2-[2-(2-methoxybenzyl)-1H-benzimidazol-5-yl]imidazo[1,2-a]pyridin-3-yl}pyrimidin-2-amine;
4-[2-(2-benzyl-1H-benzimidazol-5-yl)imidazo[1,2-a]pyridin-3-yl]-N-phenylpyrimidin-2-amine;
4-{2-[2-(2-chlorobenzyl)-1H-benzimidazol-5-yl]imidazo[1,2-a]pyridin-3-yl}-N-{3-[2-(dimethylamino)ethyl]phenyl}pyrimidin-2-amine;
N-{3-[2-(dimethylamino)ethyl]phenyl}-4-(2-{2-[2-(trifluoromethyl)benzyl]-1H-benzimidazol-5-yl}imidazo[1,2-a]pyridin-3-yl)pyrimidin-2-amine;
4-[6-(2-benzyl-1H-benzimidazol-6-yl)imidazo[2,1-b][1,3]thiazol-5-yl]-N-{3-[2-(dimethylamino)ethyl]phenyl}pyrimidin-2-amine;
N-{3-[2-(dimethylamino)ethyl]phenyl}-4-{6-[2-(2-methoxybenzyl)-1H-benzimidazol-6-yl]imidazo[2,1-b][1,3]thiazol-5-yl}pyrimidin-2-amine;

4-{6-[2-(2-chlorobenzyl)-1H-benzimidazol-6-yl]imidazo[2,1-b][1,3]thiazol-5-yl}-N-{3-[2-(dimethylamino)ethyl]phenyl}pyrimidin-2-amine;

N-{3-[2-(dimethylamino)ethyl]phenyl}-4-{2-[2-(2-phenylethyl)-1H-benzimidazol-6-yl]imidazo[1,2-a]pyridin-3-yl}pyrimidin-2-amine;

N-phenyl-4-[2-(2-phenyl-1H-benzimidazol-6-yl)imidazo[1,2-a]pyridin-3-yl]pyrimidin-2-amine;

6-{3-[2-({3-[2-(dimethylamino)ethyl]phenyl}amino)pyrimidin-4-yl]imidazo[1,2-a]pyridin-2-yl}-N-phenyl-1H-benzimidazol-2-amine;

N-{3-[2-(dimethylamino)ethyl]phenyl}-4-[2-(2-phenyl-1H-benzimidazol-6-yl)imidazo[1,2-a]pyridin-3-yl]pyrimidin-2-amine;

4-[2-(2-benzyl-1H-benzimidazol-6-yl)imidazo[1,2-a]pyridin-3-yl]-N-(2-methoxy-4-morpholin-4-ylphenyl)pyrimidin-2-amine;

4-[2-(2-benzyl-1H-benzimidazol-6-yl)imidazo[1,2-a]pyridin-3-yl]-N-(2-methoxyphenyl)pyrimidin-2-amine;

4-[2-(2-benzyl-1H-benzimidazol-6-yl)imidazo[1,2-a]pyridin-3-yl]-N-[3-(methylsulfonyl)phenyl]pyrimidin-2-amine;

3-({4-[2-(2-benzyl-1H-benzimidazol-6-yl)imidazo[1,2-a]pyridin-3-yl]pyrimidin-2-yl}amino)-N,N-dimethylbenzenesulfonamide;

4-[2-(2-benzyl-1H-benzimidazol-6-yl)imidazo[1,2-a]pyridin-3-yl]-N-[4-(methylsulfonyl)phenyl]pyrimidin-2-amine;

6-[3-(2-anilinopyrimidin-4-yl)imidazo[1,2-a]pyridin-2-yl]-N-phenyl-1H-benzimidazol-2-amine;

4-{2-[2-(2-methoxybenzyl)-1H-benzimidazol-6-yl]imidazo[1,2-a]pyridin-3-yl}-N-(2-methoxy-4-morpholin-4-ylphenyl)pyrimidin-2-amine;

4-{2-[2-(2,6-difluorobenzyl)-1H-benzimidazol-6-yl]imidazo[1,2-a]pyridin-3-yl}-N-(2-methoxy-4-morpholin-4-ylphenyl)pyrimidin-2-amine;

4-[2-(2-benzyl-1H-benzimidazol-5-yl)imidazo[1,2-a]pyridin-3-yl]-N-{2-methoxy-4-[4-(4-methylpiperazin-1-yl)piperidin-1-yl]phenyl}pyrimidin-2-amine;

4-[6-(2-benzyl-1H-benzimidazol-6-yl)imidazo[2,1-b][1,3]thiazol-5-yl]-N-phenylpyrimidin-2-amine;

4-[6-(2-benzyl-1H-benzimidazol-6-yl)imidazo[2,1-b][1,3]thiazol-5-yl]-N-(2-methoxyphenyl)pyrimidin-2-amine;

4-[2-(2-benzyl-1H-benzimidazol-6-yl)imidazo[1,2-a]pyridin-3-yl]-N-(5-methyl-1H-pyrazol-3-yl)pyrimidin-2-amine;

4-[2-(2-benzyl-1H-benzimidazol-6-yl)imidazo[1,2-a]pyridin-3-yl]-N-(3-cyclopropyl-1H-pyrazol-5-yl)pyrimidin-2-amine;

N-(2-methoxy-4-morpholin-4-ylphenyl)-4-[2-(2-phenyl-1H-benzimidazol-6-yl)imidazo[1,2-a]pyridin-3-yl]pyrimidin-2-amine;

4-[2-(2-benzyl-1H-benzimidazol-5-yl)-5,6,7,8-tetrahydroimidazo[1,2-a]pyridin-3-yl]-N-phenylpyrimidin-2-amine;

3-({4-[2-(2-benzyl-1H-benzimidazol-5-yl)imidazo[1,2-a]pyridin-3-yl]pyrimidin-2-yl}amino)pyridin-2(1H)-one;

4-[6-(2-benzyl-1H-benzimidazol-6-yl)imidazo[2,1-b][1,3]thiazol-5-yl]-N-{-4-[4-(dimethylamino)piperidin-1-yl]-2-methoxyphenyl}pyrimidin-2-amine;

$N^1$-{4-[6-(2-benzyl-1H-benzimidazol-6-yl)imidazo[2,1-b][1,3]thiazol-5-yl]pyrimidin-2-yl}-2-methoxy-$N^4$,$N^4$-dimethylbenzene-1,4-diamine;

4-[2-(2-benzyl-1H-benzimidazol-6-yl)imidazo[1,2-a]pyridin-3-yl]-N-(4-chloro-2-methoxyphenyl)pyrimidin-2-amine;

$N^1$-(4-{6-[2-(2-chlorobenzyl)-1H-benzimidazol-6-yl]imidazo[2,1-b][1,3]thiazol-5-yl}pyrimidin-2-yl)-2-methoxy-$N^4$,$N^4$-dimethylbenzene-1,4-diamine;

2-methoxy-$N^1$-(4-{6-[2-(2-methoxybenzyl)-1H-benzimidazol-6-yl]imidazo[2,1-b][1,3]thiazol-5-yl}pyrimidin-2-yl)-$N^4$,$N^4$-dimethylbenzene-1,4-diamine;

4-[2-(2-benzyl-1H-benzimidazol-5-yl)imidazo[1,2-a]pyridin-3-yl]-N-(1-methyl-1H-pyrazol-4-yl)pyrimidin-2-amine;

2-[4-({4-[2-(2-phenyl-1H-benzimidazol-5-yl)imidazo[1,2-a]pyridin-3-yl]pyrimidin-2-yl}amino)-1H-pyrazol-1-yl]ethanol;

2-[4-({4-[2-(2-benzyl-1H-benzimidazol-5-yl)imidazo[1,2-a]pyridin-3-yl]pyrimidin-2-yl}amino)-1H-pyrazol-1-yl]ethanol;

N-(4-fluorophenyl)-4-[2-(2-phenyl-1H-benzimidazol-6-yl)imidazo[1,2-a]pyridin-3-yl]pyrimidin-2-amine;

4-[2-(2-benzyl-1H-benzimidazol-5-yl)imidazo[1,2-a]pyridin-3-yl]-N-(4-fluorophenyl)pyrimidin-2-amine;

N-(2,4-difluorophenyl)-4-[2-(2-phenyl-1H-benzimidazol-6-yl)imidazo[1,2-a]pyridin-3-yl]pyrimidin-2-amine;

4-[2-(2-benzyl-1H-benzimidazol-5-yl)imidazo[1,2-a]pyridin-3-yl]-N-(2,4-difluorophenyl)pyrimidin-2-amine;

N-[2-(pyrrolidin-1-ylmethyl)phenyl]-4-(6-{2-[2-(trifluoromethyl)benzyl]-1H-benzimidazol-6-yl}imidazo[2,1-b][1,3]thiazol-5-yl)pyrimidin-2-amine;

4-[2-(2-benzyl-1H-benzimidazol-6-yl)imidazo[1,2-a]pyridin-3-yl]-N-[2-methoxy-5-(methylsulfonyl)phenyl]pyrimidin-2-amine;

N-(1-methyl-1H-pyrazol-4-yl)-4-[2-(2-phenyl-1H-benzimidazol-5-yl)imidazo[1,2-a]pyridin-3-yl]pyrimidin-2-amine;

4-[2-(2-benzyl-1H-benzimidazol-6-yl)imidazo[1,2-a]pyridin-3-yl]-N-[2-methoxy-5-(trifluoromethyl)phenyl]pyrimidin-2-amine;

N-{4-[(dimethylamino)methyl]phenyl}-4-(6-{2-[2-(trifluoromethyl)benzyl]-1H-benzimidazol-6-yl}imidazo[2,1-b][1,3]thiazol-5-yl)pyrimidin-2-amine;

1-{[4-({4-[2-(2-benzyl-1H-benzimidazol-5-yl)imidazo[1,2-a]pyridin-3-yl]pyrimidin-2-yl}amino)-3-methoxyphenyl]amino}-2-methylpropan-2-ol;

2-[[4-({4-[2-(2-benzyl-1H-benzimidazol-6-yl)imidazo[1,2-a]pyridin-3-yl]pyrimidin-2-yl}amino)-3-methoxyphenyl](methyl)amino]ethanol;

N-[4-({4-[2-(2-benzyl-1H-benzimidazol-5-yl)imidazo[1,2-a]pyridin-3-yl]pyrimidin-2-yl}amino)-3-methoxyphenyl]glycine;

2-[[3-({4-[2-(2-benzyl-1H-benzimidazol-6-yl)imidazo[1,2-a]pyridin-3-yl]pyrimidin-2-yl}amino)-4-methoxybenzyl](methyl)amino]ethanol;

$N^1$-[3-({4-[2-(2-benzyl-1H-benzimidazol-6-yl)imidazo[1,2-a]pyridin-3-yl]pyrimidin-2-yl}amino)phenyl]-$N^2$,$N^2$-dimethylglycinamide;

N-{4-[4-(dimethylamino)piperidin-1-yl]-2-methoxyphenyl}-4-(6-{2-[2-(trifluoromethyl)benzyl]-1H-benzimidazol-6-yl}imidazo[2,1-b][1,3]thiazol-5-yl)pyrimidin-2-amine;

$N^1$-[3-({4-[2-(2-benzyl-1H-benzimidazol-6-yl)imidazo[1,2-a]pyridin-3-yl]pyrimidin-2-yl}amino)-4-methoxyphenyl]-$N^2$,$N^2$-dimethylglycinamide;

4-{6-[2-(2-chlorobenzyl)-1H-benzimidazol-6-yl]imidazo[2,1-b][1,3]thiazol-5-yl}-N-{4-[4-(dimethylamino)piperidin-1-yl]-2-methoxyphenyl}pyrimidin-2-amine;

N-{4-[4-(dimethylamino)piperidin-1-yl]-2-methoxyphenyl}-4-{6-[2-(2-methoxybenzyl)-1H-benzimidazol-6-yl]imidazo[2,1-b][1,3]thiazol-5-yl}pyrimidin-2-amine;

N-{4-[4-(dimethylamino)piperidin-1-yl]-2-methoxyphenyl}-4-{6-[2-(2-methylbenzyl)-1H-benzimidazol-6-yl]imidazo[2,1-b][1,3]thiazol-5-yl}pyrimidin-2-amine;

4-[6-(2-benzyl-1H-benzimidazol-6-yl)imidazo[2,1-b][1,3]thiazol-5-yl]-N-{4-[(dimethylamino)methyl]phenyl}pyrimidin-2-amine;

4-[6-(2-benzyl-1H-benzimidazol-6-yl)imidazo[2,1-b][1,3]thiazol-5-yl]-N-{2-[(dimethylamino)methyl]phenyl}pyrimidin-2-amine;

1-{3-[(4-{3-[2-(2-chlorobenzyl)-1H-benzimidazol-5-yl]-1H-pyrazol-4-yl}pyrimidin-2-yl)amino]phenyl}pyrrolidin-2-one;

N-{3-[(dimethylamino)methyl]phenyl}-4-{1-ethyl-3-[2-(2-methoxybenzyl)-1H-benzimidazol-5-yl]-1H-pyrazol-4-yl}pyrimidin-2-amine;

4-{3-[2-(2-chlorobenzyl)-1H-benzimidazol-5-yl]-1-ethyl-1H-pyrazol-4-yl}-N-{3-[(dimethylamino)methyl]phenyl}pyrimidin-2-amine;

5-{4-[2-({3-[(dimethylamino)methyl]phenyl}amino)pyrimidin-4-yl]-1-ethyl-1H-pyrazol-3-yl}-N-phenyl-1H-benzimidazol-2-amine;

4-[3-(2-benzyl-1H-benzimidazol-5-yl)-1-ethyl-1H-pyrazol-4-yl]-N-{3-[(dimethylamino)methyl]phenyl}pyrimidin-2-amine;

4-[3-(2-benzyl-1H-benzimidazol-5-yl)-1-ethyl-1H-pyrazol-4-yl]-N-(2-methoxyphenyl)pyrimidin-2-amine;

4-{1-ethyl-3-[2-(2-methoxybenzyl)-1H-benzimidazol-5-yl]-1H-pyrazol-4-yl}-N-(2-methoxyphenyl)pyrimidin-2-amine;

4-[3-(2-benzyl-1H-benzimidazol-5-yl)-1-ethyl-1H-pyrazol-4-yl]-N-{4-[4-(dimethylamino)piperidin-1-yl]-2-methoxyphenyl}pyrimidin-2-amine;

4-{3-[2-(2-chlorobenzyl)-1H-benzimidazol-5-yl]-1-ethyl-1H-pyrazol-4-yl}-N-{4-[4-(dimethylamino)piperidin-1-yl]-2-methoxyphenyl}pyrimidin-2-amine;

N-{4-[4-(dimethylamino)piperidin-1-yl]-2-methoxyphenyl}-4-{1-ethyl-3-[2-(2-methoxybenzyl)-1H-benzimidazol-5-yl]-1H-pyrazol-4-yl}pyrimidin-2-amine; and N-{4-[4-(dimethylamino)piperidin-1-yl]-2-methoxyphenyl}-4-[1-ethyl-3-(2-phenyl-1H-benzimidazol-5-yl)-1H-pyrazol-4-yl]pyrimidin-2-amine.

21. A pharmaceutical composition comprising a compound of claim 1 or pharmaceutically acceptable salt or solvate thereof, and one or more pharmaceutically acceptable carrier.

22. A method for treating cancer in a mammal comprising administering thereto a therapeutically effective amount of a compound of claim 1 or pharmaceutically acceptable salt or solvate thereof.

23. A method for decreasing tumor volume in a mammal comprising administering thereto a therapeutically effective amount of a compound of claim 1 or pharmaceutically acceptable salt or solvate thereof.

24. The method of claim 22, wherein the cancer is bladder cancer, breast cancer, cervical cancer, colon cancer, endometrial cancer, esophageal cancer, lung cancer, ovarian cancer, pancreatic cancer, prostate cancer, rectal cancer, skin cancer, stomach cancer or thyroid cancer.

25. A method for treating cancer in a mammal comprising administering thereto a therapeutically effective amount of a compound of claim 1 or pharmaceutically acceptable salt or solvate thereof, in combination with radiotherapy.

* * * * *